(12) United States Patent
Satyam

(10) Patent No.: US 9,844,599 B2
(45) Date of Patent: Dec. 19, 2017

(54) NITRIC OXIDE RELEASING PRODUGS OF THERAPEUTIC AGENTS

(71) Applicant: Apparao Satyam, Mumbai (IN)

(72) Inventor: Apparao Satyam, Mumbai (IN)

( * ) Notice: Subject to any disclaimer, the term of this patent is extended or adjusted under 35 U.S.C. 154(b) by 0 days.

(21) Appl. No.: 14/761,887

(22) PCT Filed: Jan. 17, 2014

(86) PCT No.: PCT/IN2014/000033
§ 371 (c)(1),
(2) Date: Jul. 17, 2015

(87) PCT Pub. No.: WO2014/111957
PCT Pub. Date: Jul. 24, 2014

(65) Prior Publication Data
US 2015/0328323 A1 Nov. 19, 2015

(30) Foreign Application Priority Data

Jan. 21, 2013 (IN) .......................... 181/MUM/2013

(51) Int. Cl.
| | | |
|---|---|---|
| *A61K 31/21* | (2006.01) | |
| *A61K 31/60* | (2006.01) | |
| *C07D 201/04* | (2006.01) | |
| *A61K 47/48* | (2006.01) | |
| *C07C 229/42* | (2006.01) | |
| *C07C 201/04* | (2006.01) | |
| *C07C 227/18* | (2006.01) | |
| *A61K 31/216* | (2006.01) | |

(Continued)

(52) U.S. Cl.
CPC ............ *A61K 47/481* (2013.01); *A61K 31/21* (2013.01); *A61K 31/216* (2013.01); *A61K 31/60* (2013.01); *A61K 31/621* (2013.01); *C07C 201/04* (2013.01); *C07C 203/04* (2013.01); *C07C 227/18* (2013.01); *C07C 229/42* (2013.01)

(58) Field of Classification Search
CPC ... C07C 201/00; C07C 203/00; C07C 201/04; A61K 31/21; A61K 4/4817; A61K 31/60
USPC ......................... 514/161, 162, 165, 166, 509
See application file for complete search history.

(56) References Cited

U.S. PATENT DOCUMENTS

| | | | |
|---|---|---|---|
| 6,610,676 B1 | 8/2003 | Del Soldato | |
| 6,613,784 B1 | 9/2003 | Benedini et al. | |

(Continued)

FOREIGN PATENT DOCUMENTS

| | | |
|---|---|---|
| CN | 1966484 A | 5/2007 |
| CN | 101053662 A | 10/2007 |

(Continued)

OTHER PUBLICATIONS

International Search Report for PCT Application No. PCT/IN2014/000033, dated Jun. 5, 2014, 3 pages.

(Continued)

*Primary Examiner* — Janet L Coppins
(74) *Attorney, Agent, or Firm* — Sreenivasarao Vepachedu

(57) ABSTRACT

The present invention relates to nitric oxide releasing pro-drugs of known drugs or therapeutic agents wherein the drug or therapeutic agents contain at least one carboxylic acid group. The invention also relates to processes for the preparation of these nitric oxide releasing prodrugs, to pharmaceutical compositions containing them and to methods of using these produgs.

6 Claims, 12 Drawing Sheets

Oral absorption profile of aspirin and its prodrugs I-D1-R1 (i.e., P7097), I-D1-R2 (i.e., P7244) and I-D1-R3 (i.e., P7245) in SD Rats; A) Line graph; B) Bar graph.

(51) Int. Cl.
  A61K 31/621  (2006.01)
  C07C 203/04  (2006.01)

(56) References Cited

U.S. PATENT DOCUMENTS

| | | | |
|---|---|---|---|
| 7,199,154 B2 * | 4/2007 | Berthelette | C07C 317/46 514/509 |
| 7,220,749 B2 | 5/2007 | Letts et al. | |
| 7,524,836 B2 | 4/2009 | Del Soldato | |
| 2006/0058363 A1 | 3/2006 | Wang et al. | |
| 2008/0293781 A1 | 11/2008 | Gasco et al. | |
| 2011/0263526 A1 * | 10/2011 | Satyam | C07C 203/04 514/50 |

FOREIGN PATENT DOCUMENTS

| | | |
|---|---|---|
| EP | 0722434 B1 | 7/1996 |
| EP | 1219306 A1 | 7/2002 |
| WO | 9530641 A1 | 11/1995 |
| WO | 9716405 A1 | 5/1997 |
| WO | 9809948 A2 | 3/1998 |
| WO | 9821193 A1 | 5/1998 |
| WO | 9858910 A1 | 12/1998 |
| WO | 2001010814 A1 | 2/2001 |
| WO | 2003084550 A1 | 10/2003 |
| WO | 2003094923 A1 | 11/2003 |
| WO | 2004004648 A2 | 1/2004 |
| WO | 2004020384 A1 | 3/2004 |
| WO | 2004035042 A1 | 4/2004 |
| WO | 2004105754 A1 | 12/2004 |
| WO | 2005011646 A2 | 2/2005 |
| WO | 2005030224 A1 | 4/2005 |
| WO | 2005070868 A1 | 8/2005 |
| WO | 2007054451 A1 | 5/2007 |
| WO | 2007088123 A2 | 8/2007 |
| WO | 2007099548 A1 | 9/2007 |
| WO | 2008095809 A1 | 8/2008 |
| WO | 2009000592 A1 | 12/2008 |

OTHER PUBLICATIONS

Hyo-Kyung Han and Gordon L. Amidon, Targeted Prodrug Design to Optimize Drug Delivery, AAPS PharmSci 2000, 2(1), Mar. 21, 2000.

Symposium on "New Anti-inflammatory agents: NO-NSAIDs and COX-2 inhibitors" part of the 11th international conference on "Advances in prostaglandin and leukotrine research: Basic science and new clinical applications" held in Florence (Italy), Jun. 4-8, 2000.

Menlo Bolla et al., Therapeutic Potential of Nitrate Esters of Commonly Used Drugs, Curr. Topics Med. Chem. 2005; 5: 707-720. (Abstract only).

Kubes, Paul & Wallace, John L., Nitric Oxide as a Mediator of Gastrointestinal Mucosal Injury?—Say it ain't so; Mediators of Inflammation, 1995;4: 397-405.

Kulkarni, S.K., Jain, N.K., Singh, A., Nitric Oxidxe-releasing NSAIDs: A new dimension in nonsteroidal antiinflammatory drugs; Drugs of the Future 2001; 26(5): 485. (Abstract only).

J.E. Keeble and P.K. Moore, Pharmacology and potential therapeutic applications of nitric oxide-releasing non-steroidal anti-inflammatory and related nitric oxide-donating drugs. British Journal of Pharmacology, 2002; 137(3): 295-310. (Article first published online: Feb. 2, 2009) (Abstract only).

Muscara M.N.; Wallace J.L.; Nitric Oxide, V. Therapeutic potential of nitric oxide donors and inhibitors, American Journal of Physiology, Gastrointestinal and liver physiology, 1999; 39: G1313-1316.

Berguad et al., Nitric Oxide-Releasing Drugs—A Novel Class of Effective and Safe Therapeutic Agents, Ann. N. Y. Acad. Sci., 962: 360-371, 2002. (Abstract only).

S Fiorucci, P Del Soldato, NO-aspirin: mechanism of action and gastrointestinal safety, Dig Liver Dis 2003; 35 (suppl. 2), 9-19. (Abstract only).

Lirk, P., Hoffmann, G., and Rieder, J., Inducible nitric oxide synthase—time for reappraisal, Curr. Drug Targets Inflamm. Allergy, 2002; 1:89-108. (Abstract only).

Ian L Megson, David J Webb, Nitric oxide donor drugs: current status and future trends, Expert Opin. Investing. Drugs, 2002; 11(5): 587-601. (Abstract only).

Press reports on naproxcinod and NCX4016, www.nicox.com; 2014.

Nemmani, Kumar V.S. et al., NO-NSAIDs: Gastric-sparing nitric oxide releasable prodrugs of non-steroidal anti-inflammatory drugs, Bioorganic & Medicinal Chemistry Letters 19 (2009), 5297-5301.

Pathan, A. R., et al., Oral bioavailability, efficacy and gastric tolerability of P2026, a novel nitric oxide-releasing diclofenac in rat, Inflammopharmacology, 2010, 18(4), 157-168. (Abstract only).

O.A. al-Swayeh et al., A comparison of the anti-inflammatory and anti-nociceptive activity of nitroaspirin and aspirin, British Journal of Pharmacology (2000) 129, 343-350.

Lanas, Angel, Role of nitric oxide in the gastrointestinal tract, Arthritis Research & Therapy 2008, 10(Suppl 2): S4, Oct. 17, 2008.

Dermot Cox et al, Effect of enteric coating on antiplatet activity of low-dose aspirin in healthy volunteers, Stroke 2006; 37(8): 2153-8.

Patrignani, Paola et al., Selective Cumulative Inhibition of Platelet Thromboxane Production by Low-dose Aspirin in Healthy Subjects, American Society for Clinical Investigations 69, Jun. 1982, 1366-1372.

Esser, Ronald et al., Preclinical pharmacology of lumiracoxib: a novel selective inhibitor of cyclooxygenase-2, Br. J. Pharmacol. 2006, 144, 538-550. (Abstract only).

Gund, Machindra et al., Gastric-sparing nitric oxide releasable 'true' prodrugs of aspirin and naproxen, Bioorganic & Medicinal Chemistry Letters 24 (2014), 5587-5592.

* cited by examiner

1A)
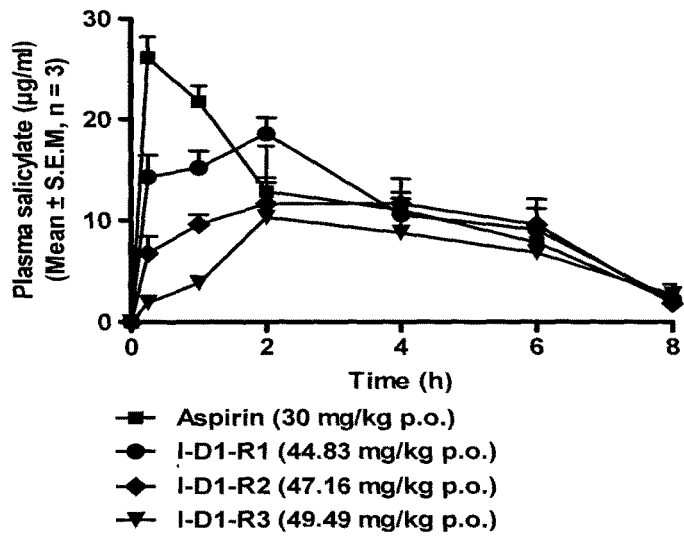
1B)
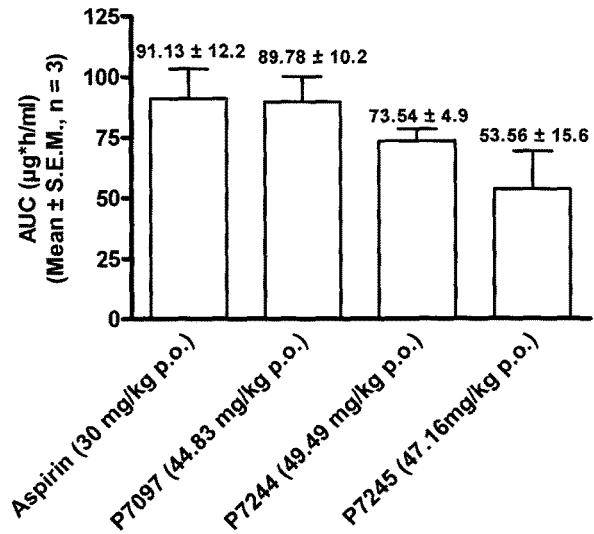
Figure 1. Oral absorption profile of aspirin and its prodrugs I-D1-R1 (i.e., P7097), I-D1-R2 (i.e., P7244) and I-D1-R3 (i.e., P7245) in SD Rats; A) Line graph; B) Bar graph.

2A)
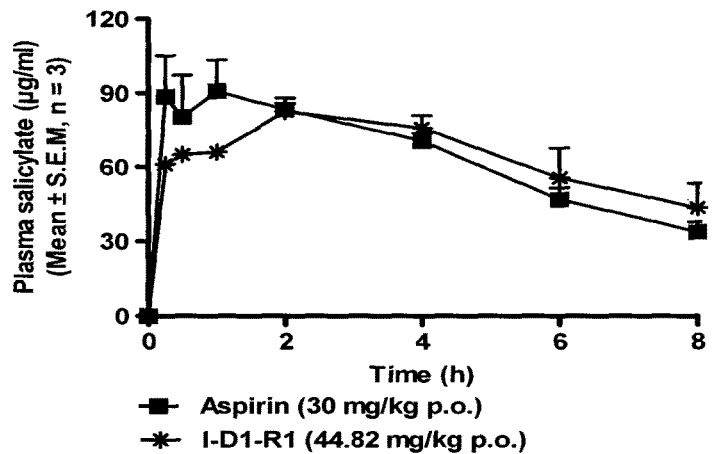
2B)
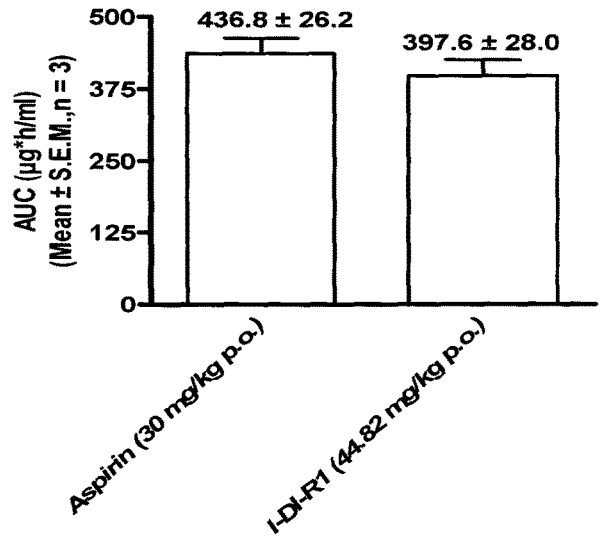
Figure 2. Oral Absorption profile of aspirin and its prodrug I-D1-R1 in Wistar Rats; A) Line graph; B) Bar graph.

3A)
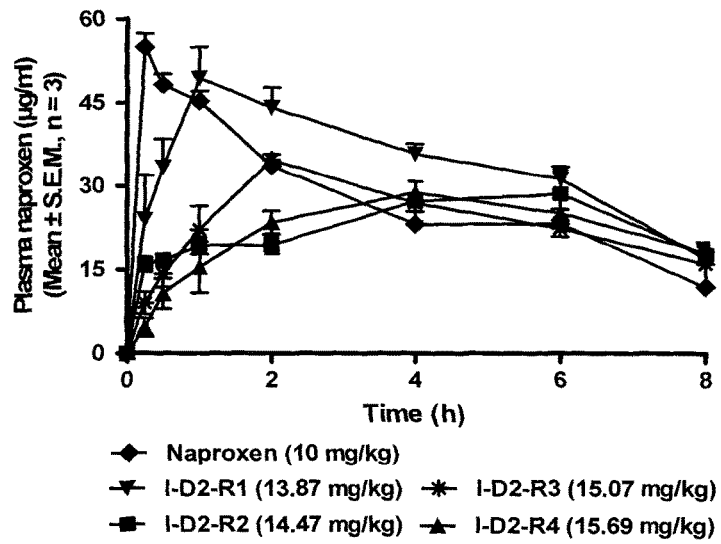
3B)
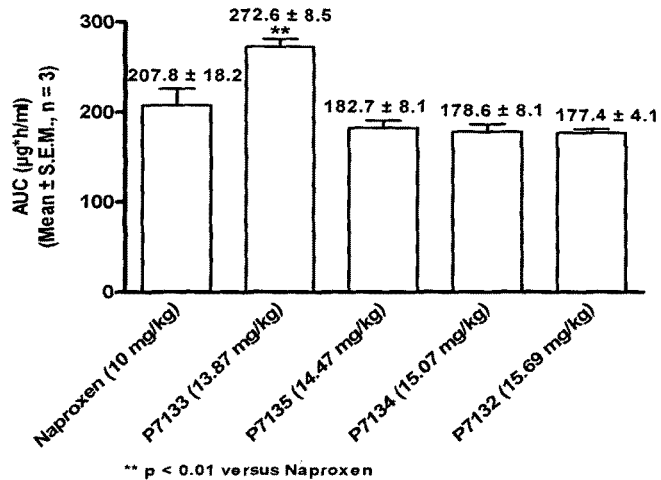
Figure 3. Oral absorption profile of naproxen and its prodrugs I-D2-R1 (i.e., P7133), I-D2-R2 (i.e., P7135), I-D2-R3 (i.e., P7134) and I-D2-R4 (i.e., P7132) in SD Rats; A) Line graph; B) Bar graph.

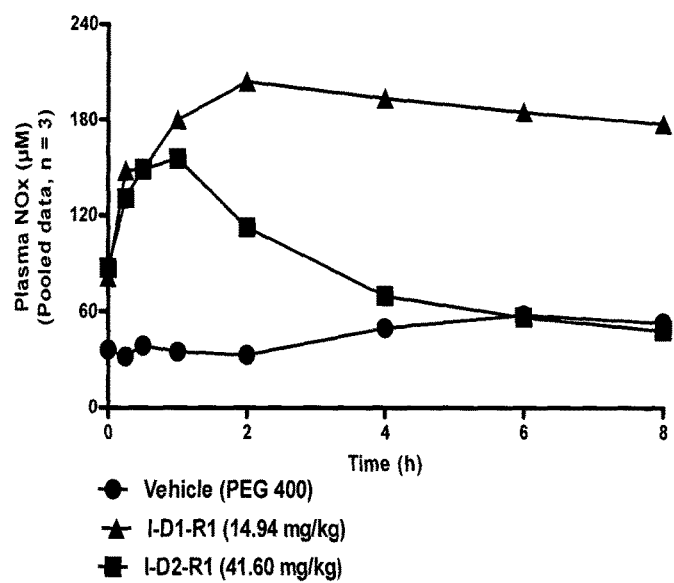
Figure 4. Plasma NOx (nitrate/nitrite) levels following oral administration of prodrugs I-D1-R1 and I-D2-R1 in rats.

5A)

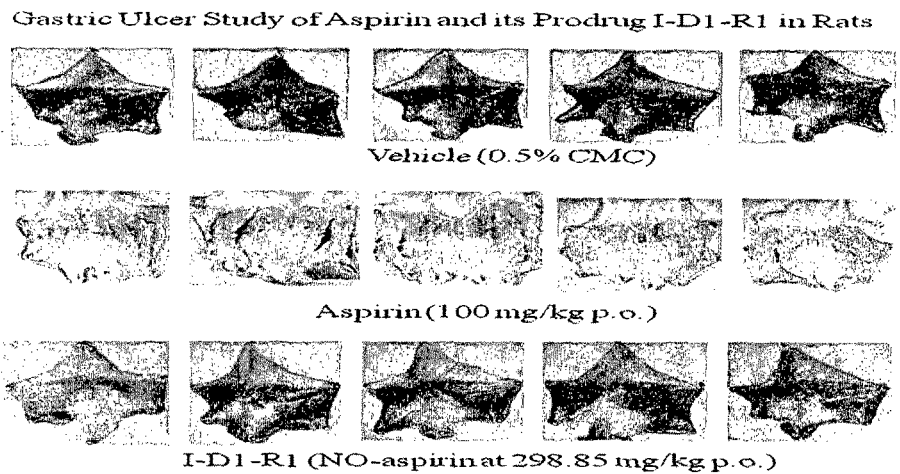

5B)

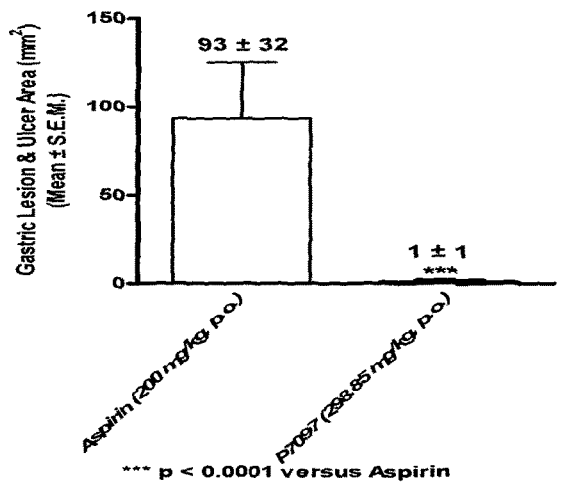

Figure 5. A) Images of rat stomachs showing gastric lesion and ulcer induction/sparing following acute oral administration of aspirin (100 mg/kg) and its promising prodrug I-D1-R1 (i.e., P7097 or NO-aspirin) at 298.85 mg/kg, which is a dose equimolar to 200 mg/kg of aspirin; B) Gastric lesion & ulcer area ($mm^2$) of rat stomachs after acute oral dosing of rats with aspirin (100 mg/kg) and its prodrug I-D1-R1 (298.85 mg/kg, which is a dose equimolar to 200 mg/kg of aspirin).

6A)

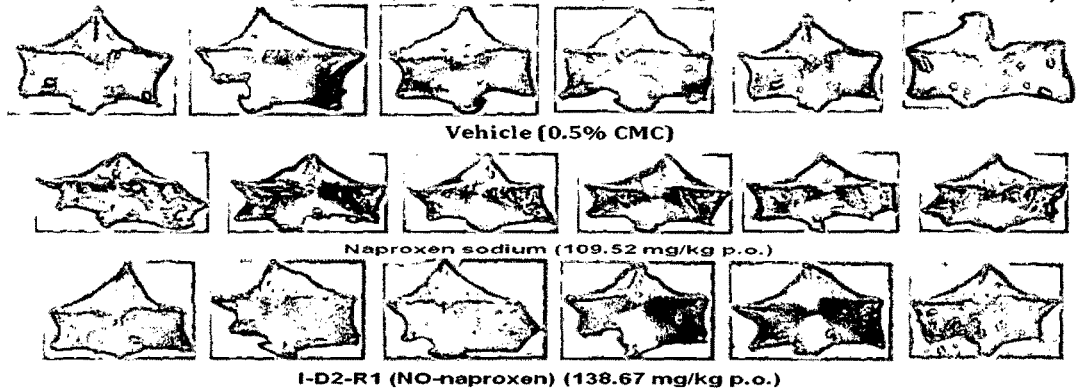

6B)

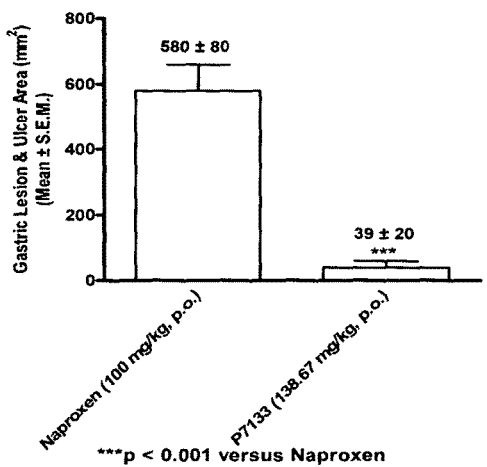

Figure 6. A) Images of rat stomachs showing gastric lesion and ulcer induction/sparing following acute oral administration of naproxen sodium (109.52 mg/kg, which is equimolar to 100 mg/kg dose of naproxen) and its promising prodrug I-D2-R1 (i.e., P7133 or NO-naproxen) at 138.67 mg/kg, which is a dose equimolar to 100 mg/kg dose of naproxen in rats; B) Gastric lesion area ($mm^2$) of rat stomachs after acute oral dosing of rats with naproxen sodium (138.67 mg/kg, which is a dose equimolar to 100 mg/kg dose of naproxen) and its prodrug I-D1-R1 (138.67 mg/kg, which is a dose equimolar to 100 mg/kg of naproxen).

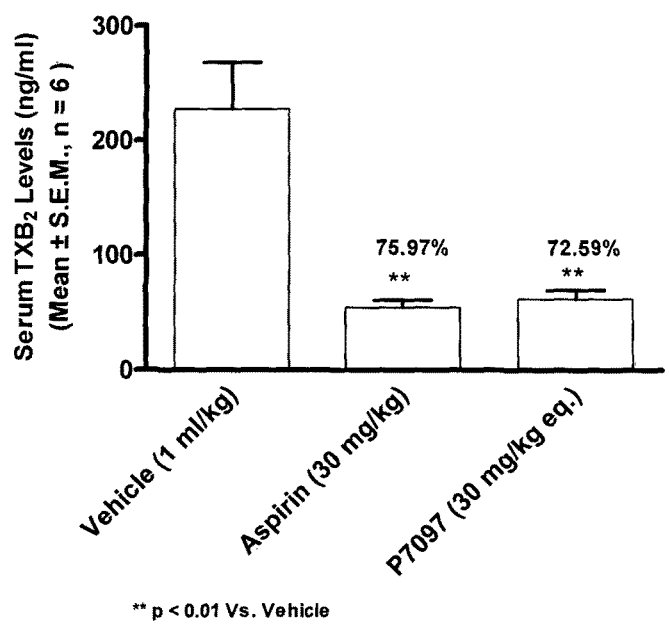
Figure 7. *In vivo* inhibition of TXB$_2$ (i.e., indicated by the reduction in serum TXB2 levels) after oral dosing of rats with aspirin (30 mg/kg) and its promising prodrug I-D1-R1 (i.e., P7097 or NO-aspirin, 44.82 mg/kg, which is equimolar to 30 mg/kg dose of aspirin).

8A)
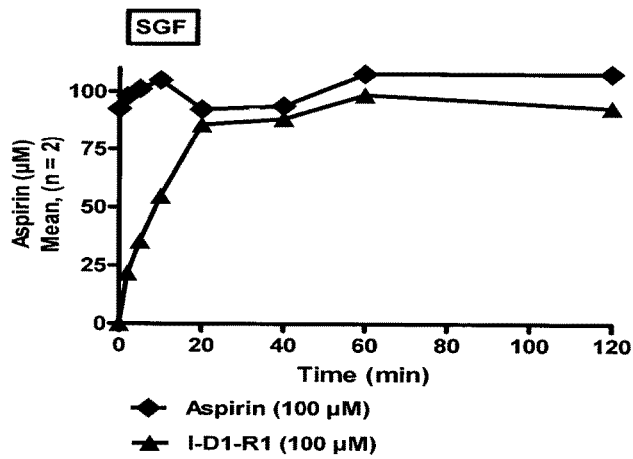
8B)
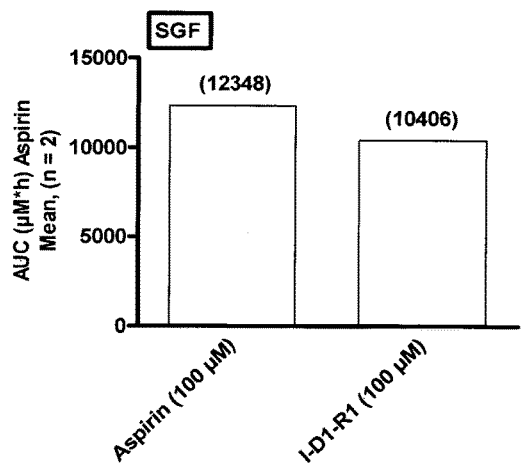
Figure 8. Release of aspirin from prodrug I-D1-R1 in Simulated Gastric Fluid (SGF); Pooled data (n = 2); A) Line graph; B) Bar graph.

9A)
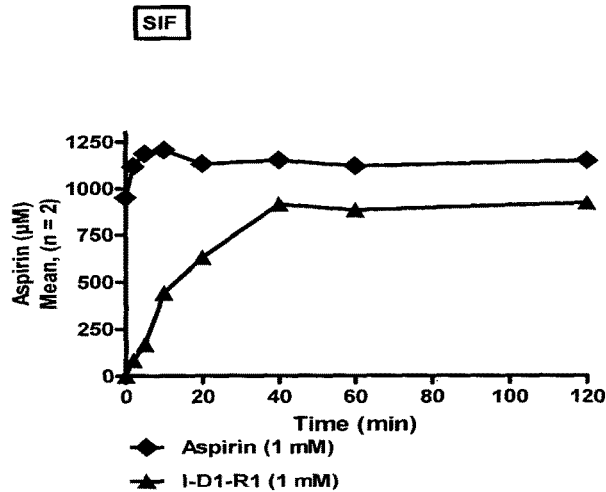
9B)
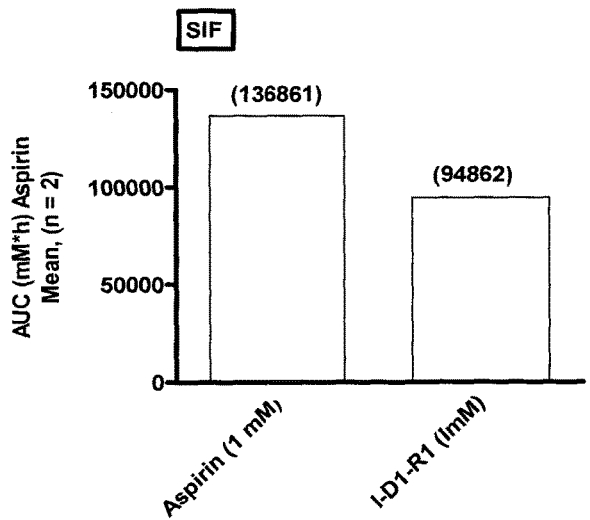
Figure 9. Stability of aspirin (1 mM)/ Release of aspirin from I-D1-R1 (1 mM) in Simulated Intestinal Fluid (SIF); Pooled data (n = 2); A) Line graph; B) Bar graph.

10A)
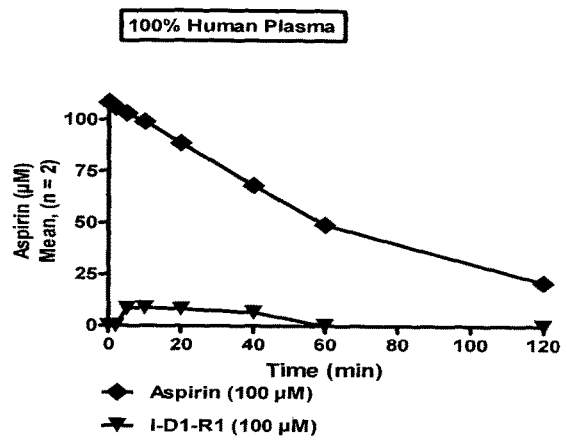
10B)
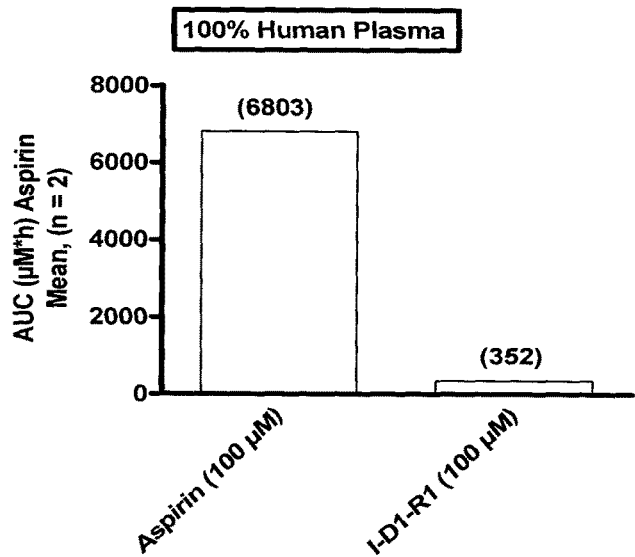
Figure 10. Degradation of aspirin (100 μM) and release of aspirin from aspirin prodrug I-D1-R1 (NO-aspirin, 100 μM) in human plasma; Pooled data (n = 2); A) Line graph; B) Bar graph.

11A)
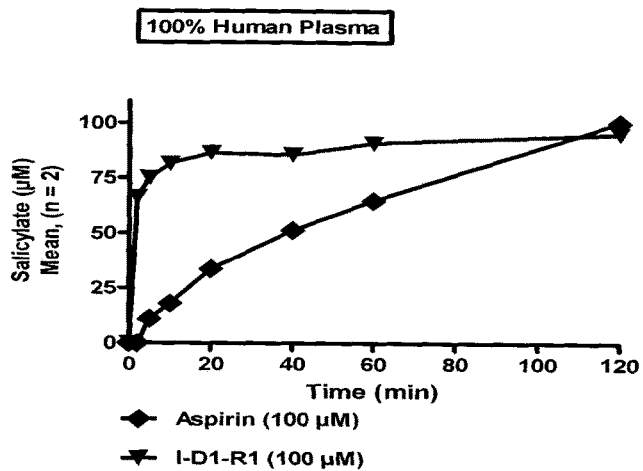
11B)
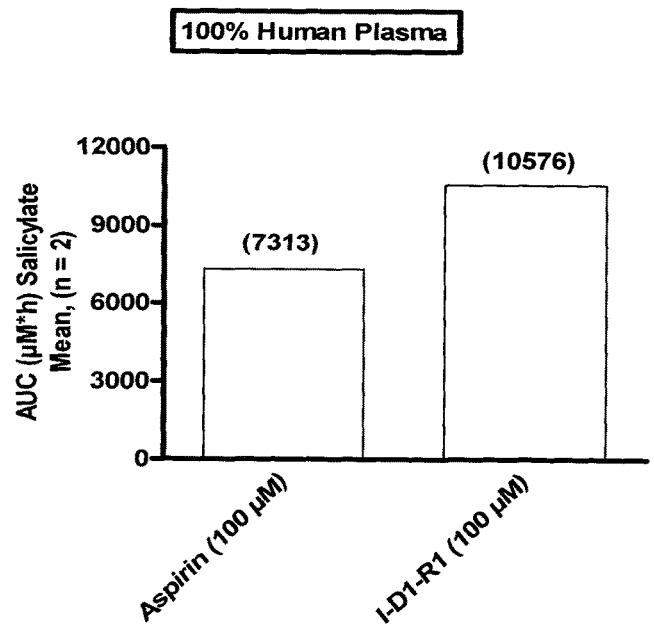
Figure 11. Release of salicylic acid from aspirin (100 μM) and its prodrug I-D1-R1 (100 μM) in human plasma; Pooled data (n = 2); A) Line graph; B) Bar graph.

12A)
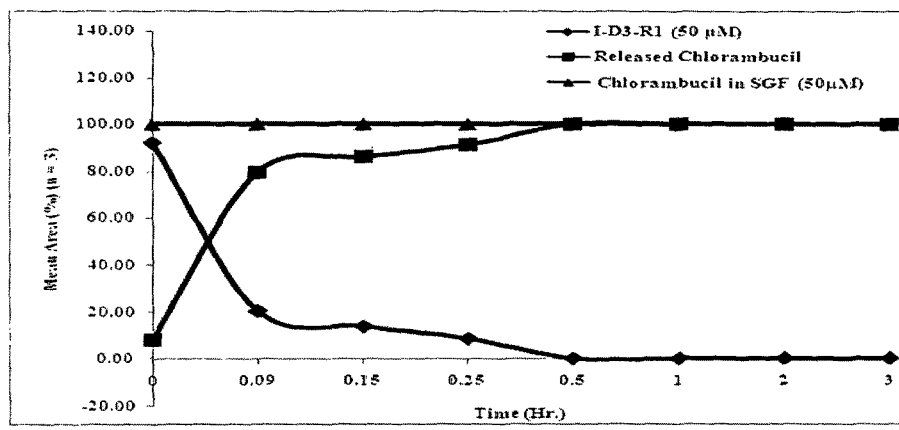
12B)
| Time (mins) | I-D3-R1 | | Chlorambucil | |
|---|---|---|---|---|
| | I-D3-R1 Remaining (%) | Chlorambucil Released (%) | Chlorambucil Remaining (%) | Other metabolite (%) |
| 0 | 92.12 | 7.88 | 100.00 | 0.00 |
| 5 | 20.49 | 79.51 | 100.00 | 0.00 |
| 10 | 13.84 | 86.16 | 100.00 | 0.00 |
| 15 | 8.59 | 91.41 | 100.00 | 0.00 |
| 30 | 0.00 | 100.00 | 100.00 | 0.00 |
| 60 | 0.00 | 100.00 | 100.00 | 0.00 |
| 120 | 0.00 | 100.00 | 100.00 | 0.00 |
| 180 | 0.00 | 100.00 | 100.00 | 0.00 |
Figure 12. Stability of chlorambucil (50 µM)/ Release of chlorambucil from I-D3-R1 (50 µM) in Simulated Gastric Fluid (SGF); Pooled data (n = 3); A) Line graph; B) Table.

NITRIC OXIDE RELEASING PRODUGS OF THERAPEUTIC AGENTS

RELATED APPLICATIONS

This application claims priority to PCT Application No. PCT/IN2014/000033, filed Jan. 17, 2014 and published on Jul. 24, 2014 as International Publication No. WO 2014/111957, which itself claims priority to Indian Patent Application No. 181/MUM/2013, filed Jan. 21, 2013, the disclosures and teachings of which are incorporated herein by reference.

FIELD OF THE INVENTION

The present invention relates to nitric oxide releasing prodrugs of known drugs or therapeutic agents which are represented herein as compounds of formula (I) wherein the drugs or therapeutic agents contain at least one carboxylic acid group. The invention also relates to processes for the preparation of the nitric oxide releasing prodrugs (the compounds of formula (I)), pharmaceutical compositions containing them and methods of using the prodrugs.

BACKGROUND OF THE INVENTION

Many drugs (therapeutic agents) have undesirable properties, for instance, low oral drug absorption, toxicity, poor patient compliance etc., that may become pharmacological, pharmaceutical, or pharmacokinetic barriers in clinical drug application. Among the various approaches to minimize the undesirable drug properties, while retaining the desirable therapeutic activity, the chemical approach using drug derivatisation offers perhaps the highest flexibility and has been demonstrated as an important means of improving drug efficacy (Hyo-Kyung Han and Gordon L. Amidon AAPS PharmSci. 2000; 2 (1)).

The conventional approach that is adopted to minimize the toxic side effects associated with the therapeutic agents has been to derivatise one or more functional groups present in the drug molecule. The derivatives are then assessed for their therapeutic efficacy as well as toxicity. The carboxylic acid group is often present as an active functional group for derivatisation in several therapeutic agents. Non-steroidal anti-inflammatory drugs (NSAIDs) represent one of the best class of drugs containing a carboxylic acid group as an active functional group. NSAIDs are also the most commonly used drugs to relieve pain, symptoms of arthritis and soft tissue inflammation. Most patients with rheumatoid arthritis receive NSAIDs as a first-line treatment which is continued for prolonged periods. Although, NSAIDs provide anti-inflammatory and analgesic effects, they also have adverse effects on the upper gastrointestinal (GI) tract. The occurrence of GI toxicity appears to be strictly correlated to the mechanism of action of these drugs, namely the inhibition of the enzyme cyclooxygenase. In fact, inhibition of platelet cyclooxygenase, which causes prolonged bleeding time, and inhibition of cyclooxygenase in gastrointestinal mucosa, which results in a decreased synthesis of cytoprotective gastric prostaglandins, represent the major cause of serious gastrointestinal toxicity (Symposium on "New Anti-inflammatory agents: NO-NSAIDs and COX-2 inhibitors" part of the 11$^{th}$ international conference on "Advances in prostaglandin and leukotrine research: Basic science and new clinical applications" held in Florence (Italy), Jun. 4-8, 2000). This problem has been solved by derivatisation of carboxylic acid group of NSAIDs into its ester and amide derivatives.

Another common approach to minimize adverse effects of the known drugs or therapeutic agents consists of attaching a carrier group to the therapeutic agents to alter their physicochemical properties and then subsequent enzymatic or non-enzymatic cleavage to release the active drug molecule (therapeutic agent). The therapeutic agent is linked through a covalent linkage to specialized non-toxic protective groups or carriers or promoieties in a transient manner to alter or eliminate undesirable properties associated with the parent drug to produce a carrier-linked prodrug.

Indeed, a more recent strategy for devising a gastric-sparing NSAID involves chemically coupling a nitric oxide (NO) releasing moiety to the parent NSAID. The approach and possibility of combining a few classes of drugs bearing different functional groups susceptible of derivatisation with NO-donating moieties has been described by Menlo Bolla et al., in Curr. Topics Med. Chem. 2005; 5: 707-720.

Nitric oxide is one of the most important mediators of mucosal defense, influencing factors such as mucus secretion, mucosal blood flow, ulcer repair and the activity of a variety of mucosal immunocytes (Med Inflammation, 1995; 4: 397-405). It has been reported to play a critical role in maintaining the integrity of the gastroduodenal mucosa and exerts many of the same effects as endogenous prostaglandins (Drugs Fut 2001; 26(5): 485). Several mechanisms are considered to underlie its protective effect in the stomach including vasodilation of local mucosal blood vessels, inhibition of leukocyte adhesion and inhibition of caspase enzyme activity. The inactivation of caspase(s) appears to be an important factor in the GI tolerance of nitric oxide releasing NSAIDs (NO-NSAIDs) (J. E. Keeble and P. K. Moore, British Journal of Pharmacology, 2002; 137: 295-310). Nitric oxide can thus be used to devise a gastric-sparing NSAID. Compounds that release nitric oxide in small amounts over a prolonged period of time may be very useful for the prevention of gastrointestinal injury associated with shock and with the use of drugs that have ulcerogenic effects (Muscara M. N.; Wallace J. L. American Journal of Physiology, Gastrointestinal and liver physiology, 1999; 39: G1313-1316).

In recent years, several NO-releasing non-steroidal anti-inflammatory drugs (NO-NSAIDs) have been synthesized by an ester linkage formed through coupling of a NO-releasing chemical spacer group to the carboxylic acid moiety of a conventional NSAID. The use of various aliphatic, aromatic or heterocyclic chemical spacers makes it possible to alter various physicochemical properties and kinetics of nitric oxide release (Berguad et al., Ann. N.Y. Acad. Sci. 1962: 360-371 (2002)). The first NO-asprin drug NCX 4016, which was synthesized relatively recently, consists of an aspirin molecule linked by an ester bond to a molecular spacer, which in turn, is linked to a nitro-oxy ester group (Dig Liver Dis 2003; 35 (suppl. 2):9-19). A number of NO-NSAID hybrid compounds, namely NO-naproxen (Naproxcinod), NO-flurbiprofen (HCT 1026), NO-ibuprofen, NO-diclofenac and NO-indomethacin have been disclosed in the patent numbers EP 722434B1, U.S. Pat. No. 6,613,784 B1 and U.S. Pat. No. 7,220,749 B2, respectively. European Patent EP 722434B1 discloses nitrate esters of the derivatives of propionic acid, 1-(p-chlorobenzoyl)-5-methoxy-2-methyl-3-indolylacetic acid and 5-benzoyl-1,2-dihydro-3H-pyrrolo[1,2-a]pyrrole-1-carboxylic acid having anti-inflammatory and/or analgesic activity. U.S. Pat. No. 6,613,784 B1 discloses nitro derivatives of NSAIDs, for instance, flurbiprofen, indomethacin, aspirin, naproxen and diclofenac. U.S. Pat. No. 7,220,749 B2 discloses novel nitrosated and/or nitrosylated derivatives of COX-2 selective inhibitors. U.S. Patent Application Publication no. 20080293781A1 describes O-acyl salicylic acid derivatives bearing a NO donor moiety. U.S. Pat. No. 7,199,154 B2 discloses nitrosated or nitrosylated prodrugs for COX-2 selective inhibitors that are useful for treating COX-2 mediated diseases or conditions and which can be administered alone or in combination with low-dose aspirin. The compounds are effective in treating chronic COX-2 mediated diseases or conditions, reducing the risk of thrombotic cardiovascular events and possibly renal side effects and at the same time reduce the risk of GI ulceration and bleeding. US Patent Application Publication no. 20060058363 A1 discloses nitric-oxide releasing prodrugs of celebrex and valdecoxib which are useful in the treatment of COX-2 mediated diseases. The compounds may be used as a combination therapy with low-dose aspirin to treat COX-2 mediated diseases or conditions while simultaneously reducing the risk of thrombotic cardiovascular events.

Nitric oxide (NO) also plays an important role in numerous other physiological and pathophysiological conditions, e.g. blood pressure regulation, inflammation, infection and the onset and progression of malignant and cardiovascular diseases (Lirk, P., Hoffmann, G., and Rieder, J. Curr. Drug Targets Inflamm. Allergy 2002; 1:89-108). Though delivery of supplementary NO in the form of NO-donor drugs has long been an attractive therapeutic strategy (Ian L Megson, David J Webb, Expert Opin. Investing. Drugs, 2002; 11(5): 587-601), in recent years, with the advent of NO-NSAID approach and because of the beneficial biochemical and pharmacological properties of nitric oxide, the strategy of linking NO-releasing moieties has been extended to a wide array of therapeutic agents selected from cardiovascular drugs, for instance, Angiotensin converting enzyme (ACE) inhibitors, calcium antagonists and beta-blockers, antitumor agents, antihistamines, glucocorticoids, etc. The aim of this strategy is to synthesize prodrugs that retain the pharmacological activity of the parent drug molecule coupled with the benefits of the biological actions of NO in reducing the adverse effects of the parent drug molecule.

U.S. Pat. Nos. 6,610,676 and 7,524,836 B2 disclose nitrate esters and nitrooxy derivatives of steroidal compounds having anti-inflammatory, immunodepressive and angiostatic activity or gastrointestinal activity.

PCT Application Publication WO2007099548A1 discloses 11β-hydroxyandrosta-4-3-one compounds which possess useful anti-inflammatory activity whilst having insignificant or no noteworthy side-effects at efficacious doses. PCT Application Publication. WO2008095809A1 discloses derivatives of known corticosteroids, containing a NO-releasing moiety which are useful in the treatment of illnesses wherein the known corticosteroid, parent or precursor steroid, is generally applied, with increased benefit in terms of pharmacological profile and fewer or milder side effects than those of the parent corticosteroids.

The NO-releasing derivatives and prodrugs of various therapeutic agents known in the art are in different phases of clinical development and there are reports suggesting that a few of them have been suspended because of some problems (see press reports on naproxcinod and NCX4016 at www.nicox.com). Therefore, there is a clear unmet medical need for new, alternative and better NO-releasing nitrate ester prodrug compounds which can exhibit improved therapeutic properties.

One such class of compounds can be represented by the following generic or Markush structure (IA):

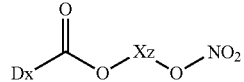

(IA)

Wherein,

Dx represents a part of a drug or therapeutic agent containing at least one carboxylic acid group which forms a bio-cleavable ester bond with the specified linker and such drug or therapeutic agent is selected from the group consisting of non-steroidal anti-inflammatory, analgesic and antipyretic drugs such as aspirin, diclofenac, naproxen and the like, COX-2 inhibitors, angiotensin-II receptor blockers such as sartans (i.e., losartan, valsatan, candesartan, telmisartan, eprosartan and olmesartan), ACE inhibitors such as captopril, enalapril and the like, beta (β)-blockers such as timolol, atenolol and the like, HMG-CoA reductase inhibitors (cholesterol-reducing agents) such as statins (i.e., fluvastatin, pravastatin, cerivastatin, atorvastatin and rosuvastatin), antiulcerative agents such as misoprostol acid and so on among others;

Xz independently represents at each occurrence a linear or branched alkylene $C_1$-$C_{20}$ preferably alkylene $C_1$-$C_{10}$, yet preferably alkylene $C_1$-$C_6$, yet preferably alkylene $C_2$-$C_{10}$, substituted alkylene $C_1$-$C_{20}$, substituted alkylene $C_1$-$C_{10}$, cycloalkylene $C_3$-$C_7$, cycloalkylene $C_5$-$C_7$, optionally substituted cycloalkylene $C_3$-$C_7$ or $C_5$-$C_7$, or $[C(R^a)(R^b)]_m$, Wherein, m=1-20, preferably 1-10, yet preferably 1-6 or 2-10 or 2-5;

$R^a$ and $R^b$ at each occurrence are independently a hydrogen, substituted or unsubstituted straight or branched alkyl $C_1$-$C_{20}$, preferably alkyl $C_1$-$C_{10}$, or yet preferably alkyl $C_1$-$C_6$ or $R^a$ and $R^b$ taken together with the carbon atom to which they are attached form a cycloalkyl group, and so on among others;

The above Markush formula (IA) is deduced from the following 20 relevant patent applications.
1. WO2007054451 (Nicox S. A., Fr.).
2. CN101053662 (Jiangsu Wuzhong Suyao Drugs Development Co., Ltd., Peop. Rep. China).
3. WO2005070868 (Merck Frosst Canada & Co., Can.).
4. WO2005030224 (Nicox S. A., Fr.).
5. WO2005011646; Family: AU2004260830 (Nicox S. A., Fr.).
6. WO2004035042, Family: AU2003269774 (Astrazeneca UK Limited, UK).
7. WO2004004648, Family: CA2491127 (Nitromed, Inc., USA).
8. WO2003094923, Family: AU2003236636 (Scaramuzzino, Giovanni), WO2003084550, Family: AU2003224002 (Nicox S. A., Fr.).
9. EP1219306, Family: AU2002219225 (Nicox S. A., Fr.).
10. WO9821193, Family: CA2272063 (Nicox S. A., Fr.; Del Soldato, Piero).
11. WO9809948, Family: EP931065 (Nicox S. A., Fr.).
12. WO9716405, Family: EP871606 (Nicox S. A., Fr.).
13. WO9530641, Family: EP759899 (Nicox Ltd., Ire.).
14. WO2007088123, Family: AU2007211508 (Nicox S. A., Fr.).

15. CN1966484 (Beijing Meibeita Pharmaceutical Research Co., Ltd., Peop. Rep. China).
16. WO2004020384, Family: EP1532098 (Nicox S. A., Fr.).
17. WO2001010814, Family: EP1200386 (Nicox S. A., Fr.).
18. WO2009000592, Family: EP2164484 (Nicox S. A., Fr.).
19. WO2004105754, Family: US7166638 (Nicox S. A., Fr.).
20. WO9858910, Family: EP989972 (Nicox S. A., Fr.).

We now report a small set of compounds of formula (I) which possesses surprising and unexpected properties when compared with compounds of formula (IA).

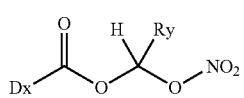
(I)

Wherein,

Dx is a part of a drug/therapeutic agent containing at least one carboxylic acid group [i.e., $DxCO_2H$] which is covalently bonded to the specified linker "C(H)(Ry)" via a bio-cleavable ester linkage;

Ry is an alkyl $C_1$-$C_6$ or cycloalkyl $C_3$-$C_7$; preferably alkyl $C_1$-$C_4$; yet preferably alkyl $C_1$-$C_2$; yet most preferably Ry is methyl (i.e., $CH_3$);

$ONO_2$ (a nitrooxy) group is covalently bonded to the other side of the linker;

and all its geometrical and stereoisomeric forms and pharmaceutically acceptable salts thereof.

The compounds of the present invention represented by formula (I) are generically covered within the scope of some of the patents or patent applications listed above.

Obviously, the Markush formula (IA), with so many variables, would encompass several thousand or even millions of possible compounds including the compounds of formula (I) of this invention. However, none of the above mentioned prior art documents specifically disclosed or claimed any of the possible compounds of this invention that are represented specifically by the formula (I).

A characteristic and unique structural feature of the specific set of compounds of formula (I) of the invention (i.e., representing a species) when compared to those of the compounds of formula IA (i.e., representing a genus) is the presence of a unique "acyl-acetal" type linkage represented by "—C(=O)—O—C(H)(Ry)-O—" group, which is a "hybrid" form of an ester and an acetal group. This characteristic and unique structural feature possibly imparts hitherto undisclosed properties to the compounds containing this "acyl-acetal" type linkage which are essentially the compounds of this invention specifically represented by the formula (I).

Some of the characteristic properties exhibited by these unique set of compounds include:
1. The compounds of formula (I) are the only kind of nitric oxide releasing ester prodrugs of carboxyl-containing drugs that encompass the unique "acyl-acetal" type structural feature.
2. Upon incubation in simulated gastric and/or intestinal fluid/s, the compounds of formula (I) readily released significant amounts of parent drugs (including aspirin!). It is well known to the people skilled in the art that it has been a very difficult task to design a true ester prodrug of aspirin due to the presence of a very labile acetyl group which undergoes preferential hydrolysis by plasma esterases.

Consequently, a vast majority of ester prodrugs of aspirin turn out be prodrugs of salicylic acid. However, in case of aspirin, the promising NO-aspirin prodrug I-D1-R1 (i.e. Dx=D1=aspirin; Ry=R1=$CH_3$) of the present invention was seen to act as a true prodrug of aspirin, when tested for its capability to release aspirin in Simulated Gastric Fluid (SGF) (FIG. 8) and Simulated Intestinal Fluid (SIF) (FIG. 9). The prodrug I-D1-R1 was evaluated at a concentration of either 100 μM or 1 mM in SGF (aspirin was co-evaluated as a positive control under the same experimental conditions, at equimolar doses) and has shown dose dependent decrease/increase in the amount of aspirin released. In SIF also, the prodrug I-D1-R1 released significant amount of aspirin at 1 mM concentration. However, although the aspirin release increased in a dose-dependent manner, it was significantly less than that of aspirin standard at equimolar doses. In SIF, with its pH in the range of ~6-7, a certain percentage of the prodrug preferentially underwent de-acetylation to give salicylic acid intermediate which further degraded to salicylic acid.

Interestingly, the behaviour of NO-aspirin (i.e. Dx=D1=aspirin) prodrugs of formula (I) was seen to be significantly different from the analogous compounds of formula (IA) [(i.e., with the same molecular formula and molecular weight but with different structural features; i.e., structures I-D1-R1 and II-D1-X2, respectively). When these two compounds were incubated simultaneously in SGF, it was observed that only the compound of formula (I), i.e., I-D1-R1, of the present invention, released quantitative amounts of the parent drug aspirin whereas the compound of formula (IA) i.e., II-D1-X2, quickly decomposed into an unknown metabolite, without releasing even traces of aspirin. Additionally, another analogous NO-aspirin compound NCX-4016 of formula (IA) that had reached phase II clinical trials (structure shown below) remained intact (no release of parent drug, aspirin) when incubated in SGF under identical conditions (Table 1).

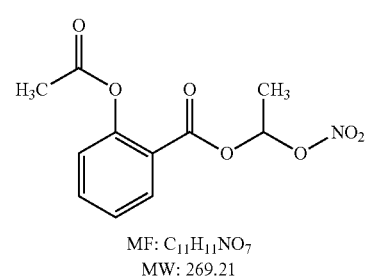

I-D1-R1

MF: $C_{11}H_{11}NO_7$
MW: 269.21

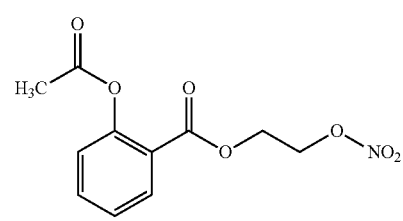

II-D1-X2

[Xz = X2 = $CH_2CH_2$]
MF: $C_{11}H_{11}NO_7$
MW: 269.21

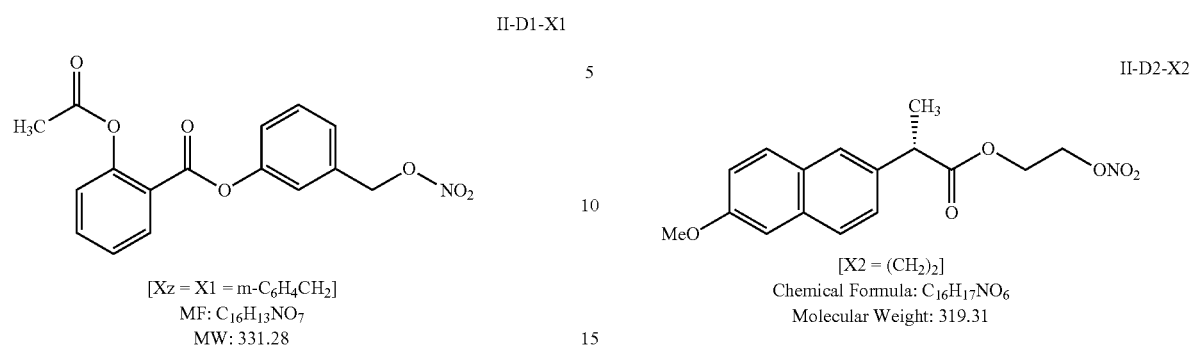

II-D1-X1

[Xz = X1 = m-C₆H₄CH₂]
MF: C₁₆H₁₃NO₇
MW: 331.28

II-D2-X2

[X2 = (CH₂)₂]
Chemical Formula: C₁₆H₁₇NO₆
Molecular Weight: 319.31

TABLE 1

Stability study of NO-aspirin prodrugs in SGF

| Time Point (min) | I-D1-R1 (Ry = R1 = CH₃) | | II-D1-X2 [Xz = X2 = CH₂CH₂] | | II-D1-X1 [NCX-4016] [Xz = X1 = m-C₆H₄CH₂] | |
|---|---|---|---|---|---|---|
| | % of Prodrug remaining (μM) | % of Aspirin Released (μM) | % of Prodrug remaining (μM) | % of Aspirin Released (μM) | % of Prodrug remaining (μM) | % of Aspirin Released (μM) |
| 0 | 91 | 0 | The prodrug underwent quick decomposition into an unknown metabolite | Aspirin release was not observed | 100.00 | Aspirin release was not observed |
| 5 | 82 | 18 | | | 100.00 | |
| 10 | 56 | 44 | | | 100.00 | |
| 30 | 3 | 97 | | | 100.00 | |
| 60 | 0 | 100 | | | 100.00 | |
| 120 | 0 | 100 | | | 100.00 | |
| $t_{1/2}$ | <15 min | | ~1.5 min | | — | |

In case of naproxen series also, the behaviour of NO-naproxen (i.e. Dx=D2=naproxen) prodrugs of formula (I) was seen to be significantly different from the analogous compounds of formula (IA) (i.e., with the same molecular formula and molecular weight but with different structural features; See structures I-D2-R1 and II-D2-X2, shown below); when incubated simultaneously in SGF, it was observed that only the compound of formula (I) of the present invention i.e., I-D2-R1 released quantitative amounts of the parent drug, naproxen whereas the compound of formula (IA) i.e., II-D2-X2 remained intact (no release of parent drug naproxen) under identical conditions (Table 2).

I-D2-R1

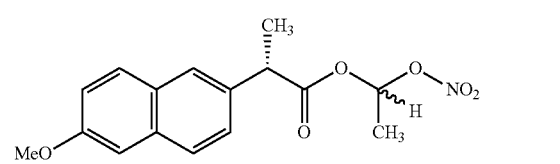

Chemical Formula: C₁₆H₁₇NO₆
Molecular Weight: 319.31

TABLE 2

Stability of prodrugs I-D2-R1 and II-D2-X2 in SGF

| | I-D2-R1 (Ry = R1 = CH₃) | | II-D2-X2 [Xz = X2 = (CH₂)₂] | |
|---|---|---|---|---|
| Time (mins) | I-D2-R1 Remaining (%) | Naproxen Released (%) | II-D2-X2 Remaining (%) | Naproxen Released (%) |
| 0 | 100.00 | 0.00 | 100.00 | 0.00 |
| 5 | 84.68 | 15.32 | 99.68 | 0.32 |
| 10 | 74.58 | 25.42 | 99.79 | 0.21 |
| 15 | 64.58 | 35.42 | 99.68 | 0.32 |
| 30 | 32.79 | 67.21 | 99.75 | 0.25 |
| 60 | 0.00 | 100.00 | 99.67 | 0.33 |
| 120 | 0.00 | 100.00 | 99.39 | 0.61 |
| 180 | 0.00 | 100.00 | 99.19 | 0.81 |
| $t_{1/2}$ | 20-25 min | | NA | |

Even the higher homologue pairs of naproxen prodrugs of formula (I) and formula (IA) i.e., I-D2-R2 vs II-D2-X3 and I-D2-R3 vs II-D2-X4 behaved in a similar fashion, when incubated simultaneously in SGF. Thus only compounds of formula (I) i.e., I-D2-R2 and I-D2-R3 released naproxen (Tables 3 and 4, respectively).

I-D2-R2

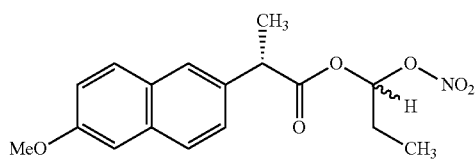

Chemical Formula: $C_{17}H_{19}NO_6$
Molecular Weight: 333.34

II-D2-X3

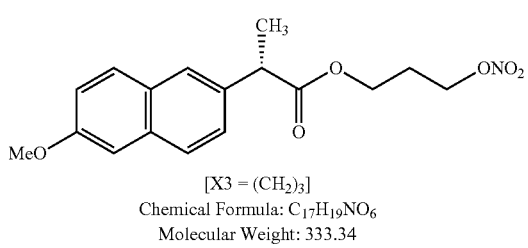

$[X3 = (CH_2)_3]$
Chemical Formula: $C_{17}H_{19}NO_6$
Molecular Weight: 333.34

TABLE 3

Stability of prodrugs I-D2-R2 and II-D2-X3 in SGF

| | I-D2-R1 (Ry = R2 = CH$_3$CH$_2$) | | II-D2-X3 [Xz = X3 = (CH$_2$)$_3$] | |
|---|---|---|---|---|
| Time (mins) | I-D2-R2 Remaining (%) | Naproxen Released (%) | II-D2-X3 Remaining (%) | Naproxen Released (%) |
| 0 | 100 | 0.00 | 100.00 | 0.00 |
| 5 | 94.33 | 5.67 | 100.00 | 0.00 |
| 10 | 90.43 | 9.57 | 100.00 | 0.00 |
| 15 | 74.27 | 25.73 | 100.00 | 0.00 |
| 30 | 62.15 | 37.85 | 100.00 | 0.00 |
| 60 | 51.01 | 48.99 | 100.00 | 0.00 |
| 120 | 39.08 | 60.92 | 100.00 | 0.00 |
| 180 | 6.77 | 93.23 | 100.00 | 0.00 |
| $t_{1/2}$ | ~1 h | | NA | |

I-D2-R3

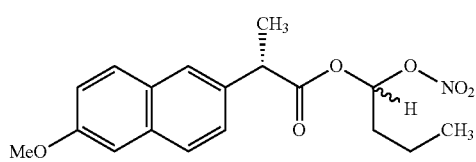

Chemical Formula: $C_{18}H_{21}NO_6$
Molecular Weight: 347.36

II-D2-X4

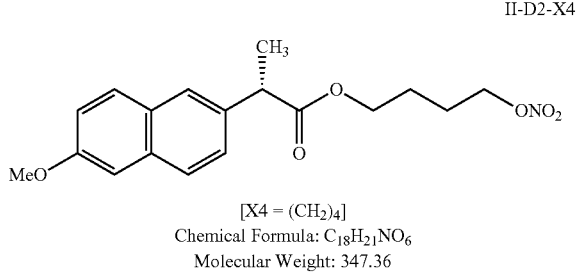

$[X4 = (CH_2)_4]$
Chemical Formula: $C_{18}H_{21}NO_6$
Molecular Weight: 347.36

TABLE 4

Stability of prodrugs I-D2-R3 and II-D2-X4 in SGF

| | I-D2-R3 (Ry = R3 = CH$_3$CH$_2$CH$_2$) | | II-D2-X4 [Xz = X4 = (CH$_2$)$_4$] | |
|---|---|---|---|---|
| Time (mins) | I-D2-R3 Remaining (%) | Naproxen Remaining (%) | II-D2-X4 Remaining (%) | Naproxen Remaining (%) |
| 0 | 100 | 0.00 | 100.00 | 0.00 |
| 5 | 96.35 | 3.65 | 100.00 | 0.00 |
| 10 | 93.61 | 6.39 | 100.00 | 0.00 |
| 15 | 83.21 | 16.79 | 100.00 | 0.00 |
| 30 | 82.73 | 17.27 | 100.00 | 0.00 |
| 60 | 75.48 | 24.52 | 100.00 | 0.00 |
| 120 | 57.55 | 42.45 | 100.00 | 0.00 |
| 180 | 39.00 | 61.00 | 100.00 | 0.00 |
| $t_{1/2}$ | ~2.5 h | | NA | |

A still higher homologue of naproxen prodrug of formula (I), i.e., I-D2-R4, also released appreciable amounts of the parent drug naproxen when incubated in SGF, as shown below (Table 5).

I-D2-R4

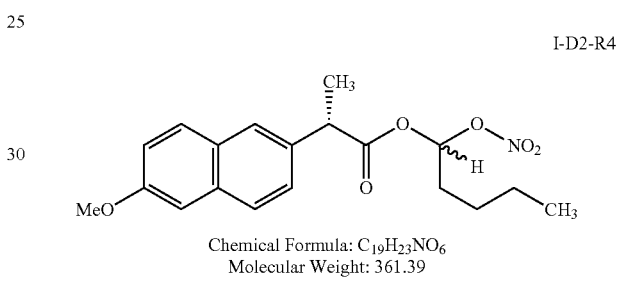

Chemical Formula: $C_{19}H_{23}NO_6$
Molecular Weight: 361.39

TABLE 5

Stability of prodrug I-D2-R4 in SGF

| | I-D2-R4 (Ry = R4 = CH$_3$CH$_2$CH$_2$CH$_2$) | |
|---|---|---|
| Time (mins) | I-D2-R4 Remaining (%) | Naproxen Released (%) |
| 0 | 100 | 0.00 |
| 5 | 97.74 | 2.26 |
| 10 | 96.18 | 3.82 |
| 15 | 87.41 | 12.59 |
| 30 | 90.53 | 9.47 |
| 60 | 88.87 | 11.13 |
| 120 | 79.97 | 20.03 |
| 180 | 71.04 | 28.96 |
| $t_{1/2}$ | >3 h | |

From the above data, it is obvious that the compounds (prodrugs of naproxen) of formula (I) release decreasing amounts of parent drug naproxen with increasing alkyl chain length of Ry (probably due to solubility issues associated with increased hydrophobicity of longer alkyl chains). Thus, the half-lives ($t_{1/2}$) of prodrugs of naproxen of formula (I) follow the pattern: I-D2-R1 ($t_{1/2}$=~20-25 min)<I-D2-R2 ($t_{1/2}$=~1 h)<I-D2-R3 ($t_{1/2}$=~2.5 h)<I-D2-R4 ($t_{1/2}$=>3 h).

Similarly, I-D3-R1, which is the nitric oxide releasing prodrug of chlorambucil of formula (I) (i.e., Dx=D3=chlorambucil, Ry=R1=CH$_3$) also released its parent drug chlorambucil quantitatively when incubated in SGF as shown below (See Table 6 and FIG. 12).

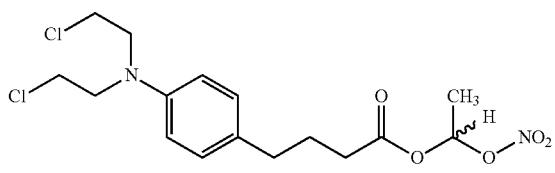

I-D3-R1

TABLE 6

Stability of prodrug I-D3-R1 in SGF

| | I-D3-R1 (Ry = R1 = CH₃) | |
|---|---|---|
| Time (mins) | I-D3-R1 Remaining (%) | Chlorambucil Released (%) |
| 0 | 92.12 | 7.88 |
| 5 | 20.49 | 79.51 |
| 10 | 13.84 | 86.16 |
| 15 | 8.59 | 91.41 |
| 30 | 0.00 | 100.00 |
| 60 | 0.00 | 100.00 |
| 120 | 0.00 | 100.00 |
| 180 | 0.00 | 100.00 |
| $t_{1/2}$ | <5 min | |

Interestingly, the chlorambucil prodrug I-D3-R1, which is the lowest carbon homologue among the chlorambucil prodrugs of formula (I), decomposed in SGF to give 100% of the parent drug chlorambucil, with a half-life of less than 5 minutes (Table 6).

3. The compounds of formula (I) exhibited nearly similar or superior oral bioavailability and efficacy as compared to those of respective parent drugs in rats (See FIGS. 1, 2, 3 and Table 7).
4. Although the compounds of formula (I) at equimolar doses exhibited nearly similar or superior oral bioavailability and efficacy as compared to those of their respective parent drugs, they did not cause any significant drug-induced gastric lesions and/or bleeding. However, their respective parent drugs at equimolar doses caused significant drug-induced gastric lesions and/or bleeding (See FIGS. 5 and 6).
5. The process for making the compounds of formula (I) differs significantly when compared to the reported processes for making the compounds of formula (IA).

For example, the most frequently used process for making the compounds of formula (IA) involves the steps, as shown in the Chart 1A:

Chart 1A: The most usual process for the synthesis of compounds of formula (IA)

Step 1:

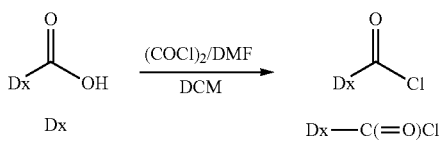

Step 2:

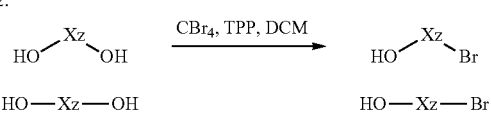

-continued

Step 3:

$$HO{\diagup}^{Xz}{\diagdown}Br \xrightarrow{AgNO_3}{ACN} HO{\diagup}^{Xz}{\diagdown}O{\diagdown}^{NO_2}$$

$$HO-Xz-Br \quad\quad HO-Xz-ONO_2$$

Step 4:

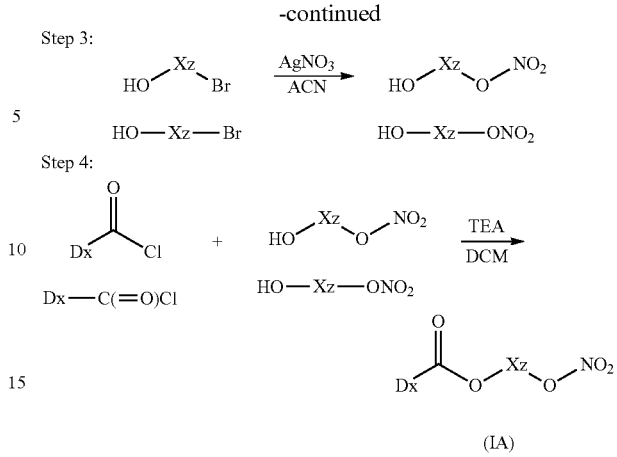

Step 1: Conversion of the drug or therapeutic agent containing carboxylic acid group (Dx-CO₂H) to its active acid chloride Dx-C(=O)Cl by reacting with thionyl chloride or oxalyl chloride in presence of catalytic amount of DMF;

Step 2: Conversion of diol HO-Xz-OH for example 1,2-Ethanediol or 1,3-Propanediol or 1,4-Butanediol (wherein Xz is as defined above), into its mono bromide derivative HO-Xz-Br, by known methods for example by treating with carbon tetrabromide and triphenylphosphine in a solvent such as DCM;

Step 3: Conversion of monobromide HO-Xz-Br from Step 3 into the corresponding mononitrate HO-Xz-ONO₂ by treating with silver nitrate in acetonitrile;

Step 4: Reaction of acid chloride from Step 1 with the mononitrate from Step 3 in the presence of a suitable base such as triethylamine in a suitable solvent such as DCM to yield the compound of formula (IA).

In contrary, the process for making the compounds of formula (I) involves significantly different steps as shown in Schemes 1 and 2.

For clarity, a plausible mechanism for the formation of the compounds of formula (I) is shown below:

Chart 1B. A Plausible mechanism for the formation of composition of the compounds of formula (I)

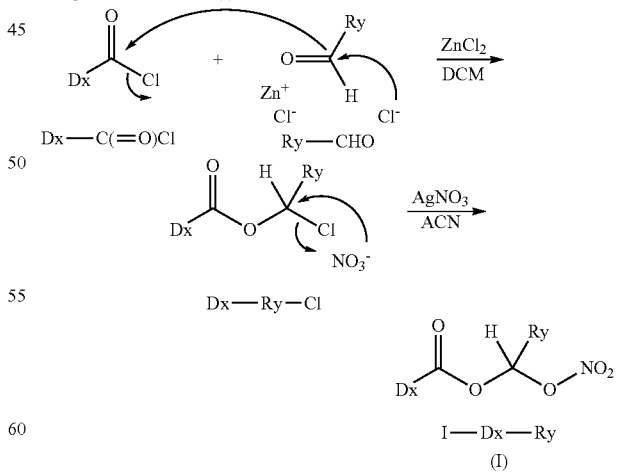

Wherein,
Dx = drug or part of the drug containing at least one carboxylic acid group;
Dx—C(=O)Cl can be freshly prepared from Dx—CO₂H by using a known method; and
Ry—Alkyl C₁-C₆.

It would be understood by a person skilled in the art that in the compounds of formula (I), the "CO" group adjacent to Dx is derived from the carboxyl group of the drug (i.e., Dx-CO$_2$H) as shown in chart 1B.

The above mentioned characteristic properties of the unique compounds of the present invention represented specifically by the formula (I) [i.e., representing a specific species comprising the compounds of formula (I)] are neither disclosed specifically in the prior art [i.e., representing the whole genus comprising the compounds of formula (IA)] nor obvious to those skilled in the art to which this invention relates. The unique structural features and characteristic properties of the compounds of formula (I) therefore constitute or impart both "novelty and inventive features" to these potentially useful compounds.

BRIEF DESCRIPTION OF DRAWINGS

FIG. 1. Oral absorption profile of aspirin and its prodrugs I-D1-R1 (i.e., P7097), I-D1-R2 (i.e., P7244) and I-D1-R3 (i.e., P7245) in SD Rats; A) Line graph; B) Bar graph.

FIG. 2. Oral Absorption profile of aspirin and its prodrug I-D1-R1 in Wistar Rats; A) Line graph; B) Bar graph.

FIG. 3. Oral absorption profile of naproxen and its prodrugs I-D2-R1 (i.e., P7133), I-D2-R2 (i.e., P7135), I-D2-R3 (i.e., P7134) and I-D2-R4 (i.e., P7132) in SD Rats; A) Line graph; B) Bar graph.

FIG. 4. Plasma NOx (nitrate/nitrite) levels following oral administration of prodrugs I-D1-R1 and I-D2-R1 in rats.

FIG. 5. A) Images of rat stomachs showing gastric lesion and ulcer induction/sparing following acute oral administration of aspirin (100 mg/kg) and its promising prodrug I-D1-R1 (i.e., P7097 or NO-aspirin) at 298.85 mg/kg, which is a dose equimolar to 200 mg/kg of aspirin; B) Gastric lesion & ulcer area (mm$^2$) of rat stomachs after acute oral dosing of rats with aspirin (100 mg/kg) and its prodrug I-D1-R1 (298.85 mg/kg, which is a dose equimolar to 200 mg/kg of aspirin).

FIG. 6. A) Images of rat stomachs showing gastric lesion and ulcer induction/sparing following acute oral administration of naproxen sodium (109.52 mg/kg, which is equimolar to 100 mg/kg dose of naproxen) and its promising prodrug I-D2-R1 (i.e., P7133 or NO-naproxen) at 138.67 mg/kg, which is a dose equimolar to 100 mg/kg dose of naproxen in rats; B) Gastric lesion area (mm$^2$) of rat stomachs after acute oral dosing of rats with naproxen sodium (138.67 mg/kg, which is a dose equimolar to 100 mg/kg dose of naproxen) and its prodrug I-D1-R1 (138.67 mg/kg, which is a dose equimolar to 100 mg/kg of naproxen).

FIG. 7. In vivo inhibition of TXB$_2$ (i.e., indicated by the reduction in serum TXB2 levels) after oral dosing of rats with aspirin (30 mg/kg) and its promising prodrug I-D1-R1 (i.e., P7097 or NO-aspirin, 44.82 mg/kg, which is equimolar to 30 mg/kg dose of aspirin).

FIG. 8. Release of aspirin from prodrug I-D1-R1 in Simulated Gastric Fluid (SGF); Pooled data (n=2); A) Line graph; B) Bar graph.

FIG. 9. Stability of aspirin (1 mM)/Release of aspirin from I-D1-R1 (1 mM) in Simulated Intestinal Fluid (SIF); Pooled data (n=2); A) Line graph; B) Bar graph.

FIG. 10. Degradation of aspirin (100 µM) and release of aspirin from aspirin prodrug I-D1-R1 (NO-aspirin, 100 µM) in human plasma; Pooled data (n=2); A) Line graph; B) Bar graph.

FIG. 11. Release of salicylic acid from aspirin (100 µM) and its prodrug I-D1-R1 (100 µM) in human plasma; Pooled data (n=2); A) Line graph; B) Bar graph.

FIG. 12. Stability of chlorambucil (50 µM)/Release of chlorambucil from I-D3-R1 (50 µM) in Simulated Gastric Fluid (SGF); Pooled data (n=3); A) Line graph; B) Table.

DETAILED DESCRIPTION OF THE INVENTION

The present invention encompasses compounds of formula (I), as described herein, which are nitric oxide releasing prodrugs of known carboxyl-containing drugs or therapeutic agents useful in the treatment of diseases or disorders that are characteristic of the drugs from which the prodrugs of the present invention are derived.

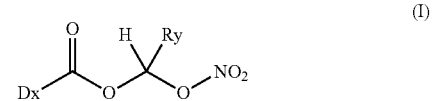

In general, the present invention provides prodrugs of known drugs or therapeutic agents represented herein by the compounds of formula (I) which primarily constitutes the following elements:

(a) a drug or a therapeutic agent containing at least one carboxylic acid group [i.e., DxCO$_2$H] that is covalently bonded to one side of the linker;

(b) a linker [i.e., C(H)(Ry)]; and (c) a nitrooxy (ONO$_2$) group covalently bonded to the other side of the linker;

The strategy for providing the prodrugs represented herein by the compounds of formula (I) is applicable to any drug or therapeutic agent which possesses a carboxylic acid functional group capable of forming a covalent ester bond to a specified linker. The linker is a bi-functional moiety having the desired covalent binding properties.

The prodrugs, i.e., the compounds of formula (I) of the present invention, would undergo either chemical or enzymatic cleavage in a manner such that the parent drugs and effective amounts of nitric oxide are released in vivo. Also, the prodrugs of the present invention [i.e. the compounds of formula (I)] are expected to be safe to administer and seem to have the potential to exhibit comparable or superior oral bioavailability to that of the parent drug molecule.

Although the compounds of formula (I) of the present invention are derived from the drugs or therapeutic agents containing at least one carboxylic acid group, many such drugs or therapeutic agents may contain other reactive functional groups such as an amino, additional carboxyl, hydroxyl (including phenolic), sulfhydryl, phosphate, aldehyde and keto (in the form of their derivatives such as oxime, hydrazone, semicarbazone and the like) groups or a mixture of one or more types of these functional groups. As a result, the compounds of formula (I) could also be represented by the following alternative formula I-a:

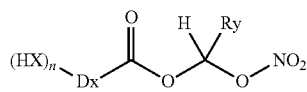

(I-a)

Wherein, (HX)$_n$-Dx-C(=O)O represents a drug or therapeutic agent containing at least one carboxylic acid group, which is covalently bonded to the specified linker "C(H)(Ry)" via a bio-cleavable ester linkage; where X independently at each occurrence represents O (i.e., corresponds to a primary, secondary, tertiary or phenolic hydroxyl group), S (i.e., corresponds to a primary, secondary, tertiary or thiophenolic sulfhydryl group), carboxylate (i.e., $CO_2^-$), amino group (i.e., NH or N, which represent primary or secondary amino groups, respectively), a phosphate [i.e., P(=O)(O$^-$)$_2$], a carbonyl group (i.e., an aldehyde or keto group in the form of their bio-cleavable derivatives such as an oxime, hydrazone, semicarbazone and the like) or a mix of one or more types of these functional groups;

n represents 0 (zero) or 1-20, preferably 0 (zero) or 1-10, yet preferably 0 (zero) or 1-5, yet most preferably 0 (zero) or 1-2;

Ry is an alkyl $C_1$-$C_6$ or cycloalkyl $C_3$-$C_7$; preferably alkyl $C_1$-$C_4$; yet preferably alkyl $C_1$-$C_2$; yet most preferably alkyl $C_1$ (i.e., $CH_3$);

$ONO_2$ (i.e., nitrooxy) group is covalently bonded to the other side of the linker;

and in all its geometrical and stereoisomeric forms and also pharmaceutically acceptable salts thereof;

Also encompassed within the scope of the invention represented by the formula (I) are the compounds of the invention, wherein, the drug or therapeutic agent contains, in addition to the required one carboxylic acid functional group, one or more other reactive functional groups such as an amino, a hydroxyl (including phenolic and hydroxyl group of oxime derivative of a carbonyl group of an aldehyde or keto group), a sulfhydryl, a phosphate or additional carboxyl group(s), or a mixture of one or more types of the said functional groups and these additional functional groups have to be specifically protected, if necessary, by appropriate bio-cleavable protecting groups ($^z$PGs); Consequently, the compounds of formula (I) could also be represented by the following alternative formula I-b:

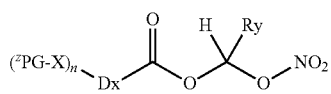

(I-b)

Wherein,

X-$^z$PG represents O-$^h$PG, S-$^s$PG, C(=O)O-$^c$PG, NH-$^a$PG, N-$^a$PG or [P(=O)(O-$^p$PG)$_2$], where $^h$PG represents a bio-cleavable hydroxyl protecting group such as acetyl group and the like;

$^s$PG represents a bio-cleavable sulfhydryl protecting group such as acetyl group, disulfide bond and the like;

$^c$PG represents a bio-cleavable carboxyl protecting group such as lower (alkyl $C_1$-$C_6$) alkyl esters and the like;

$^a$PG represents a bio-cleavable amino protecting group such as acetyl, ethoxycarbonyl, 2-acetylthioethoxycarbonyl or 2-(2-aminoethyl)dithioethoxy-carbonyl group and the like;

$^p$PG represents a bio-cleavable phosphate protecting group such as 2-(S-acetylthio)ethyl (SATE), 3-pivaloyloxy-1,3-dihydroxypropyl derivative, dithiodiethanol derivative, 4-acyloxybenzyl phosphate mono or diester derivatives and the like;

and the remaining elements of the formula (I) (or I-a or I-b) are same as defined above;

A good example of one such drug is aspirin, i.e., o-acetyl salicylic acid, wherein the anti-inflammatory drug salicylic acid has, in addition to the required one carboxylic acid group, one additional reactive phenolic hydroxyl group, which is protected by the bio-cleavable acetyl group.

Unless otherwise indicated, the following definitions are set forth to illustrate and define the meaning and scope of various terms used to describe the invention herein and the claims. These definitions should not be interpreted in the literal sense as they are not general definitions and are relevant only for this application.

As used herein, the term "prodrug or prodrugs" refers/refer to a compound/compounds which upon administration to a subject in need thereof undergoes cleavage in vivo either by enzymatic or chemical processes to release the parent drug from which the prodrug is derived.

As used herein, the terms "drug" or "drugs" 'or "therapeutic agents" or "drug molecules" or "parent drug" or "parent drug molecules", which are represented by the symbols "Dx" or "Dx-C(=O)O" or "(HX)$_n$-Dx-C(=O)O" or "(HX)$_n$-Dx-C(=O)O" or "($^z$PG-X)$_n$-Dx-C(=O)O" [where $^z$PG represent an appropriate bio-cleavable protecting group for an amino ($^a$PG) or a hydroxyl ($^h$PG) or a sulfhydryl ($^s$PG) or a carboxyl ($^c$PG) or a phosphate ($^p$PG) group] are used interchangeably when n represents 0 (zero). The term "drug" or "therapeutic agent" as used herein refers to any compound, substance, medicament or active ingredient having a therapeutic or pharmacological effect, and which is suitable for administration to a mammal, e.g., a human, more particularly, in the context of the present invention, all the known drugs or therapeutic agents containing at least one carboxylic acid functional group that is capable of forming a covalent biocleavable ester linkage with a specified linker. The term "drug" or "therapeutic agent" as used herein also encompasses within its scope the "investigational drug(s)" or "investigational agent(s)" which refer to any new drug or agent currently under clinical investigation, particularly those investigational drugs or agents that contain at least one carboxylic acid group that is capable of forming a covalent biocleavable ester linkage with a linker, which may later be established as therapeutically active agent by the regulatory bodies of different countries. As stated above, such drugs or therapeutic agents may also contain, in addition to the required one carboxylic acid group, other reactive functional groups such as an amino, additional carboxyl, hydroxyl (including phenolic), sulfhydryl, phosphate, aldehyde and keto (or their derivatives such oxime, hydrazone, semicarbazone and the like) groups. It is of common understanding that such additional reactive functional groups need to be protected, if it is necessary, with appropriate protecting groups and again those protecting groups may need to be removed at appropriate stages of the processes for the synthesis of compounds of formula (I). However, it is preferable to use such protecting groups that can be cleaved under physiological conditions so that we can avoid the process of removal of those protecting groups from the compounds of the invention represented by the formula (I). Thus, the compounds for formula (I) containing additional reactive functional groups, which are protected by appropriate bio-cleavable protecting groups, are within the scope of this invention.

As used herein, the term "linker" or "linkers" or "bio-cleavable linkers" or "spacer" or spacers" refers/refer to a chemical moiety/moieties, which forms/form a covalent ester linkage with the reactive carboxylate group of the drug or therapeutic agent to obtain a prodrug of the drug. This linker may be cleaved from the prodrug by chemical means, by enzymatic means, or by both the means. The linker may be pharmacologically inert or may itself provide added beneficial pharmacological activity.

As used herein, the term "alkyl" means a branched or straight-chain monovalent alkyl radical, having one to six carbon atoms such that the alkyl group is designated as alkyl $C_1$-$C_6$ or $C_1$-$C_6$ alkyl or alkyl $C_{1-6}$. This term is further exemplified by such radicals as methyl, ethyl, n-propyl, isopropyl, n-butyl, s-butyl, t-butyl, isobutyl, amyl, n-pentyl, neopentyl, valeryl and the like.

As used herein, the term "amino" functional group of drugs or therapeutic agents refer to the drugs containing, in addition to the required presence of one carboxylic acid group, other reactive primary and secondary amines (both acyclic and cyclic) which also include drugs containing derivatizable NH-containing functional groups such as amide-NH, sulfonamide-NH, carbamate-NH, sulfamate-NH, hydrazide-NH, hydrazone-NH, semicarbazone-NH, thiosemicarbazone-NH, urea-NH, and also encompass drug molecules with derivatizable NH-containing heterocyclic sub-structures such as aziridine, azitidine, dihydropyridine, indole, imidazole, benzimidazole, thiazole, benzothiazole, oxazole, benzoxazole, pyrrole, pyrrazole, benzopyrrozole, pyrrolidine, piperidine, triazole, benzotriazoles, tetrazole, and benzotetrazole.

As used herein, the term "hydroxyl" or "hydroxy" functional group of drugs or therapeutic agents refer to the drugs containing, in addition to the required presence of one carboxylic acid group, other reactive hydroxyl (OH) groups (i.e., these hydroxyl groups can be primary, secondary, tertiary or phenolic in nature) including hydroxyl groups of hydroxamic acids, aldoxime, ketoximes of carbonyl-containing (i.e., aldehyde or keto groups) drug molecules.

As used herein, the term "sulfhydryl" functional group of drugs or therapeutic agents refer to the drugs containing, in addition to the required presence of one carboxylic acid group, other reactive free sulfhydryl (SH) groups and these can be primary, secondary, tertiary and thiophenolic in nature.

As used herein, the term "halogen" refers to fluorine, bromine, chlorine or iodine.

As used herein, the term "halide" refers to fluoride, chloride, bromide, and iodide.

As used herein, the term "cycloalkyl" refers to a saturated mono-, bi- or polycyclic ring system containing a specified number of carbon atoms.

Unless otherwise stated, cycloalkyl rings containing 3 to 7 carbon atoms are preferred. Representative cycloalkyl groups include cyclopropyl, cyclobutyl, cyclopentyl, cyclohexyl, cycloheptyl and the like.

As used herein, the term "bio-cleavable amino protecting group" is intended to refer to a group that can be selectively attached to the nitrogen atom by chemical modification of an amino group so as to selectively inhibit participation of the amino group in chemical reactions. However, these amino protecting groups can be cleaved in vivo either chemically (pH dependent) or enzymatically. Exemplary bio-cleavable amino-protecting groups include carbamates (urethanes) such as methyl, ethyl and t-butyl (i.e., BOC or tert-butoxycarbonyl) and amides such as acetyl, methoxyacetyl, etc. The procedures for the formation of the above mentioned bio-cleavable amino protecting groups are based on the known methods and their relevant references as cited in T. W. Greene, "Protective Groups in Organic Synthesis", Third Edition, 1999, John Wiley and Sons, New York, are incorporated herein as a reference. Additional examples of bio-cleavable amino protecting groups are shown in Chart 2.

As used herein, the term "bio-cleavable hydroxyl protecting group" or "bio-cleavable hydroxy protecting group" is intended to refer to a group that can be selectively attached to the oxygen atom by chemical modification of the hydroxyl group so as to selectively inhibit the participation of the hydroxyl group in chemical reactions. Examples of such bio-cleavable hydroxyl and phenolic-protecting groups include the ester groups selected from acetate ester, methoxyacetate ester, benzoate ester, phenylacetate ester, pivalate ester, phenoxyacetate ester, monosuccinate, nitrate, ethyl carbonate and methoxymethyl carbonate. The procedures for the formation of the above mentioned bio-cleavable hydroxyl protecting groups are based on the known methods and their relevant references as cited in T. W. Greene, "Protective Groups in Organic Synthesis", Third Edition, 1999, John Wiley and Sons, New York, are incorporated herein as a reference.

As used herein, the term "bio-cleavable carboxyl protecting group" or "bio-cleavable carboxylic acid protecting group" is intended to refer to a group that selectively blocks the oxygen functionality within a carboxylic acid group so as to inhibit participation of the carboxylic acid group in chemical reactions. Examples of such carboxylic acid protecting groups include for example unsubstituted and substituted alkyl esters such as methyl and ethyl. The procedures for the formation of the above mentioned carboxyl protecting groups are based on the known methods and their relevant references as cited in T. W. Greene, "Protective Groups in Organic Synthesis", Third Edition, 1999, John Wiley and Sons, New York, are incorporated herein as a reference.

As used herein, the term "bio-cleavable sulfhydryl protecting group" or "bio-cleavable thiol protecting group" is intended to refer to a group that selectively blocks the thiol (SH) functionality so as to inhibit participation of the thiol group in chemical reactions. Examples of such thiol protecting groups include thioesters such as S-acetyl and S-benzoyl and unsymmetrical disulfides such as S-ethyl disulfide and S-t-butyl disulfide. The procedures for the formation of the above mentioned bio-cleavable sulfhydryl protecting groups are based on the known methods and their relevant references as cited in T. W. Greene, "Protective Groups in Organic Synthesis", Third Edition, 1999, John Wiley and Sons, New York, are incorporated herein as a reference.

As used herein, the term "bio-cleavable phosphate protecting group" is intended to refer to a group that selectively blocks the phosphate [$P(=O)(OH)_2$] functionality so as to inhibit participation of the free phosphate group in chemical reactions. Examples of such bio-cleavable phosphate protecting groups include 2-(S-acetylthio)ethyl (SATE), 3-pivaloyloxy-1,3-dihydroxypropyl derivative, dithiodiethanol derivative, 4-acyloxybenzyl phosphate mono or diester derivatives. The procedures for the formation of the above mentioned bio-cleavable phosphate protecting groups are based on the known methods and their relevant references as cited in T. W. Greene, "Protective Groups in Organic Synthesis", Third Edition, 1999, John Wiley and Sons, New York, are incorporated herein as a reference.

The term "pharmaceutically acceptable salts" refers to the salts of the compound of formula (I) of the invention which are toxicologically acceptable and pharmaceutically utilisable salts.

The compounds of formula (I), which contains a basic functionality, can be used according to the invention in the form of their addition salts of organic or inorganic acids. The pharmaceutically acceptable acid addition salts of the prodrug compound of formula (I) include salts which retain the biological effectiveness and properties of the free bases and which are not biologically or otherwise undesirable.

Examples of suitable inorganic acids include hydrochloric acid, hydrobromic acid, sulphuric acid, nitric acid, phosphoric acid, perchloric acid, boric acid, and other inorganic acids known in the art. Examples of organic acids include: acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfanilic acid, 2-acetoxy benzoic acid, toluenesulphonic acid, methane sulphonic acid, ethane disulphonic acid, isethionic acid, ketoglutaric acid, benzenesulphonic acid and other organic acids known in the art.

The compound of formula (I), which contains additional acidic group(s), can be used according to the invention as base addition salts. Examples of pharmaceutically acceptable base addition salts include those salts derived from inorganic bases such as alkali earth metal salts like sodium, potassium, lithium, alkaline earth metal salts like calcium, magnesium, aluminium salts or salts of organic bases such as lysine, arginine, triethylamine, dibenzylamine, piperidine or salts with ammonia. Particularly preferred are the ammonium salts of the prodrugs of the present invention i.e. the compounds of formula (I).

The pharmaceutically acceptable salts of the present invention can be synthesized from the subject compound which contains a basic or acidic moiety, by conventional chemical methods. Generally the salts are prepared by contacting the free base or acid with stoichiometric amounts or with an excess of the desired salt-forming inorganic or organic acid or base in a suitable solvent or dispersant or by anion exchange or cation exchange with other salts. Suitable solvents are, for example, ethyl acetate, ether, alcohols, acetone, tetrahydrofuran (THF), dioxane or mixtures of these solvents.

In a first embodiment, the invention relates to compounds of the formula (I), which are prodrugs of known drugs or therapeutic agents;

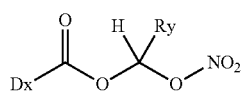

(I)

Wherein,

Dx-C(=O)O a drug or therapeutic agent containing at least one carboxylic acid group, which is covalently bonded to the specified linker "C(H)(Ry)" via a bio-cleavable ester linkage;

Optionally, Dx-C(=O)O may contain, in addition to the requisite one carboxylate group, additional reactive functional group(s) [$(X)_n$], which may be protected by appropriate bio-cleavable protecting groups ($^?$PGs). As a result, Dx-C(=O)O can be represented alternatively as $(X)_n$-Dx-C(=O)O. Thus, the compound of formula (I) could also be represented by the following alternative formula:

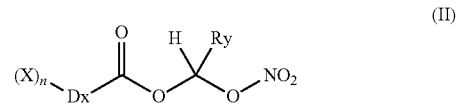

(II)

Wherein,

X independently at each occurrence represents OH (i.e., a primary, secondary, tertiary or phenolic hydroxyl group), O-$^h$PG, SH (i.e., a primary, secondary, tertiary or thiophenolic sulfhydryl group), S-$^s$PG, CO$_2$H or C(=O)O-$^c$PG, amino group (i.e., NH$_2$ or NH or N, which represent primary or secondary or tertiary amino groups, respectively), HN-$^a$PG, N-$^a$PG, a phosphate group [i.e., P(=O)(OH)$_2$], a protected phosphate group [i.e., P(=O)(O-$^p$PG)$_2$], a carbonyl group (i.e., an aldehyde or keto group in the form of their bio-cleavable derivatives such as an acetal, oxime, hydrazone, semicarbazone and the like) or a mixture of one or more types of these functional groups, where $^h$PG represents a bio-cleavable hydroxyl protecting group such as acetyl group and the like;

$^s$PG represents a bio-cleavable sulfhydryl protecting group such as acetyl group, disulfide bond and the like;

$^c$PG represents a bio-cleavable carboxyl protecting group such as lower (alkyl $C_1$-$C_6$) alkyl esters and the like;

$^a$PG represents a bio-cleavable amino protecting group such as acetyl, ethoxycarbonyl, 2-acetylthioethoxycarbonyl or 2-(2-aminoethyl)dithioethoxy-carbonyl group and the like;

$^p$PG represents a bio-cleavable phosphate protecting group such as 2-(S-acetylthio)ethyl (SATE), 3-pivaloyloxy-1,3-dihydroxypropyl derivative, dithiodiethanol derivative, 4-acyloxybenzyl phosphate mono or diester derivatives and the like;

n represents 0 (zero) or 1-20, preferably 0 (zero) or 1-10, yet preferably 0 (zero) or 1-5, yet preferably 0 (zero) or 1-2;

Ry is an alkyl $C_1$-$C_6$ or cycloalkyl $C_3$-$C_7$; preferably alkyl $C_1$-$C_4$; yet preferably alkyl $C_1$-$C_2$; yet most preferably alkyl $C_1$ (i.e., CH$_3$);

ONO$_2$ (i.e., nitrooxy) group is covalently bonded to the other side of the linker;

and in all its geometrical and stereoisomeric forms and also pharmaceutically acceptable salts thereof.

In a second embodiment, the invention encompasses a compound of formula (I), wherein:

Dx is as defined in the first embodiment herein above;

Ry is alkyl $C_1$-$C_6$;

and in all its geometric and stereoisomeric forms and pharmaceutically acceptable salts thereof.

In a third embodiment, the invention encompasses a compound of formula (I), wherein:

Dx is as defined in the first embodiment herein above;

Ry is alkyl $C_1$-$C_4$; yet preferably Ry is ethyl (CH$_2$CH$_3$); yet most preferably Ry is methyl (CH$_3$);

and in all its geometric and stereoisomeric forms and pharmaceutically acceptable salts thereof.

In a fourth embodiment, the invention encompasses a compound of formula (I), wherein: Dx, the drug or therapeutic agent containing a carboxylic acid group capable of forming a covalent bio-cleavable ester linkage with a linker, referred to in the first, second, and third embodiments, is selected from the group comprising of an anti-inflammatory and analgesic agent, a cardiovascular agent, an anti-allergic agent, an anti-cancer agent, an anti-depressant, an anti-convulsant agent, an anti-bacterial agent, an anti-fungal agent, an agent, an anti-malarial agent, an anti-lipidemic agent, an anti-diabetic agent, an anti-ulcer agent, a vitamin and an anti-oxidant.

In this embodiment, other variables of Ry in the compounds of formula (I) are as defined hereinabove;

in all its geometrical and stereoisomeric forms and pharmaceutically acceptable salts thereof.

In a fifth embodiment, in the compound of formula (I), the anti-inflammatory and analgesic agent referred to in the fourth embodiment hereinabove is selected from the group comprising of aceclofenac, acemetacin, acetamidocaproic acid, acetylsalicylsalicylic acid, actarit, alclofenac, 3-alminoprofen, amfenac, 3-amino-4-hydroxybutyric acid, aspirin (acetylsalycilic acid), balsalazide, bendazac, benoxaprofen, bromprofen, bromfenac, 5-bromosalicylic acid acetate, bucloxic acid, bumadizone, butibufen, carprofen, cinchophen, cinmetacin, clidanac, clometacin, clonixin, clopirac, diacerein, diclofenac, diflunisal, dipyrocetyl, enfenamic acid, enoxolone, etodolac, felbinac, fenbufen, fenclozic acid, fendosal, fenoprofen, fentiazac, flufenamic acid, flunoxaprofen, fluocortolone-21-acid, flurbiprofen, fosfosal, gentisic acid, ibufenac, ibuprofen, indomethacin, indoprofen, isofezolac, isoxepac, ketoprofen, ketorolac, lonazolac, loxoprofen, meclofenamic acid, mefenamic acid, mesalamine, metiazinic acid, mofezolac, naproxen, niflumic acid, olsalazine, oxaceprol, oxaprozin, pirazolac, pirprofen, pranoprofen, protizinic acid, salicysulfuric acid, salicylamide o-acetic acid, salsalate, sulfasalazine, sulindac, suprofen, suxibuzone, tiaprofenic acid, tolfenamic acid, tolmetin, tropesin, ximoprofen, zaltoprofen and zomepirac.

A representative example of an anti-inflammatory and analgesic agent is a NSAID that is selected from the group comprising of aspirin, diclofenac, diflunisal, etodolac, fenoprofen, flurbiprofen, ibuprofen, indomethacin, ketoprofen, ketorolac, naproxen, sulindac and tolmetin.

Further in the sixth embodiment, the invention encompasses a compound of formula (I); wherein the cardiovascular agent referred to in the fourth embodiment hereinabove is generically selected from the group comprising of antihypertensive agents such as angiotensin converting enzyme (ACE) inhibitors, beta-blockers, sartans (angiotensin II blockers), anti-thrombotic and vasoactive agents, anti-hyperlipidemic drugs (including HMG-CoA-reductase inhibitors (statins)), fibrates, anti-anginal agents, anti-arrhythmic agents, anticoagulants, anti-hypotensive agents, diuretics, vasodilators and vasoprotectants and is specifically selected from the group comprising of acifran, acipimox, acetylsalicylic acid, alacepril, gama-aminobutyric acid, angiotensin, argatroban, atorvastatin, benazepril, benfurodil hemisuccinate, beraprost, bezafibrate, bumetanide, candesartan, capobenic acid, captopril, carmoxirole, caronapril, cerivastatin, chromocarb, cilazapril, ciprofibrate, clinofibrate, clofibric acid, dalteparin, daltroban, delapril, dextrothyroxine, eicosapentaenoic acid, eledoisin, enalapril, enalaprilat, enoxaparin, eprosartan, ethacrynic acid, fluvastatin, fosinopril, furosemide, gemfibrozil, iloprost, imidapril, indobufen, isbogrel, heparin, lamifiban, lifibrol, limaprost, lisinopril, losartan acid (EXP-3174), lotrafiban, meglutol, melagatran, mercamphamide, mercaptomerin sodium, mercumallylic acid, mersalyl, methyldopa, moexipril, moveltipril, nadroparin, omapatrilat, ozagrel, oxiniacic acid, perindopril, piretanide, pitavastatin, pravastatin sodium, prostaglandin $E_1$, quinapril, ramipril, reviparin sodium salt, ridogrel, rosuvastatin, sampatrilat, saralasin, satigrel, spirapril, taprostene, telmisartan, temocapril, thyropropic acid, ticrynafen, tinzaparin, tirofiban, trandolapril, triflusal, valsartan, xanthinol niacinate, xenbucin and zofenopril.

A representative example of the cardiovascular agent is an ACE-inhibitor that is selected from the group comprising of benazepril, enalapril, enalaprilat, lisinopril, perindopril, quinapril, ramipril, ramiprilate, trandolapril, alacepril, captopril, ceronapril, cilazapril, delapril, fosinopril, imidapril, lisinopril, moexipril, moveltipril, omapatrilat, sampatrilat, spirapril, temocapril and zofenopril.

Another representative example of the cardiovascular agent is a sartan that is selected from the group comprising of candesartan, olmesartan, losartan acid (EXP-3174), telmisartan, and valsartan.

Yet another representative example of the cardiovascular agent is an anti-thrombotic, anticoagulant or vasodilator agent that is selected from the group comprising of acetylsalicylic acid (aspirin), argatroban, beraprost, dalteparin, daltroban, enoxaparin, iloprost, indobufen, isbogrel, heparin, lamifiban, lotrafiban, melagatran, nadroparin, ozagrel, reviparin sodium salt, ridogrel, satigrel, taprostene, tinzaparin, tirofiban and triflusal.

Yet another representative example of the cardiovascular agent is an anti-hyperlipidemic agent (statin and fibrate) that is selected from the group comprising of atorvastatin, bezafibrate, cerivastatin, ciprofibrate, clinofibrate, clofibric acid, clopidogrel free acid, fluvastatin, gemfibrozil, pitavastatin, pravastatin and rosuvastatin.

Yet another representative example of the cardiovascular agent is an anti-anginal agent such as limaprost.

Yet another representative example of the cardiovascular agent is an anti-arrhythmic agent such as capobenic acid.

Yet another representative example of the cardiovascular agent is an anti-hypotensive agent such as angiotensin II.

Yet another representative example of the cardiovascular agent is a diuretic that is selected from the group comprising of bumetanide, ethacrynic acid, furosemide, mercamphamide, mercaptomerin sodium, mercumallylic acid, mersalyl, piretanide and ticrynafen.

Yet another representative example of the cardiovascular agent is a vasodilator that is selected from the group comprising of benfurodil hemisuccinate, beraprost, eledoisin, iloprost, prostaglandin $E_1$ and xanthinol niacinate.

Yet another representative example of the cardiovascular agent is a vasoprotectant such as chromocarb.

Still further, in the seventh embodiment, the invention encompasses a compound of formula (I); wherein the anti-allergic agent referred to in the fourth embodiment hereinabove is generically selected from the group comprising of a steroidal bronchodilator, a mast cell stabilizer and an anti-histamine and is specifically selected from the group comprising of acrivastine, amlexanox, bepotastine, cetirizine, fexofenadine, levocetirizine, lodoxamide, montelukast sodium, nedocromil, olopatadine, pentigetide and tranilast.

A representative example of the anti-allergic agent is an anti-histamine that is selected from the group comprising of acrivastine, bepotastine, cetirizine, fexofenadine, levocabastine, levocetirizine and montelukast sodium.

Still further, in the eighth embodiment, the invention encompasses a compound of formula (I); wherein the anti-cancer agent referred to in the fourth embodiment hereinabove is selected from the group comprising of acitretin (etretin), aminolevulinic acid, amsilarotene, butyric acid, chlorambucil, eflornithine hydrochloride, melphalan, methotrexate, minodronate (minodronic acid), retinoic acids (including 13-cis retinoic and all trans-retinoic acids), sulindac, tamibarotene, and valproic acid.

Still further, in the ninth embodiment, the invention encompasses a compound of formula (I); wherein the anti-depressant referred to in the fourth embodiment hereinabove is generically selected from antimaniacs and antipsychotic agents and is specifically selected from the group comprising of amineptine, gabapentin, 5-hydroxytryptophan (oxitriptan), pregabalin, tianeptine, valproic acid and vigabatrin.

Still further, in the tenth embodiment, the invention encompasses a compound of formula (I); wherein the anticonvulsant referred to in the fourth embodiment hereinabove is selected from the group comprising of gabapentin, pregabalin, tiagabine, valproic acid and vigabatrin.

Still further, in the eleventh embodiment, the invention encompasses a compound of formula (I); wherein the antibacterial agent referred to in the fourth embodiment hereinabove is selected from the group comprising of acediasulfone, amdinocillin, p-aminosalicylic acid, amoxicillin, amphomycin, ampicillin, apalcillin, apicycline, aspoxicillin, azidocillin, aziocillin, aztreonam, bacitracin, balofloxacin, benzoylpas, benzylpenicillin, betamipron, biapenem, carbenicillin, carindacillin, carumonam, cefaclor, cefadroxil, cefalexin, cefamandole, cefatiam, cefatrizine, cefazedone, cefazolin, cefbuperazone, cefclidin, cefdinir, cefditoren, cefepime, cefetamet, cefixime, cefmenoxime, cefmetazole, cefminox, cefodizime, cefonicid, cefoperazone, ceforanide, cefoselis, cefotaxime, cefotetan, cefotiam, cefoxitin, cefozopran, cefpimizole, cefpiramide, cefpirome, cefroxadine, cefsulodin, ceftazidime, cefteram, ceftezole, ceftibuten, ceftizoxime, ceftriaxone, cefprozil, cefuroxime, cefuzonam, cephacetrile sodium, cephalexin, cephaloglycin, cephaloridine, cephalosporin C, cephalothin, cephapirin sodium, cephradine, cilastatin, cinoxacin, ciproflaxacin, clavulinic acid, clavulanate, clinafloxacin, clometocillin, cyclacillin, dicloxacillin, difloxacin, enoxacin, epicillin, ertapenem, fenbenicillin, fleroxacin, flomoxef, floxacillin, flumequine, fosfomycin, fropenem, fusidic acid, garenoxacin, gatifloxacin, gemifloxacin, grepafloxacin, hetacillin, hydnocarpic acid, imipenem, lomefloxacin, loracarbef, lymecycline, merbromin, meropenem, metampicillin, methicillin, mezlocillin, miloxacin, moxalactam, moxifloxacin, nadifloxacin, nafcillin, nalidixic acid, negamycin, noprysulfamide, norfloxacin, ofloxacin, opiniazide, oxacillin, oxolinic acid, panipenem, pazufloxacin, pefloxacin, penicillin(s), penimepicycline, phenethicillin, phthalylsulfacetamide, phthalylsulfathiazole, pipemidic acid, piperacillin, piromidic acid, propicillin, prulifloxacin, quinacillin, ritipenem, rosoxacin, rufloxacin, salazosulfadimidine, salbactam, sitafloxacin, sparfloxacin, succinylsulfathiazole, succisulfone, sulbenicillin, sulfachrysoidine, sulfaloxic acid, 4-sulfanilamidosalicylic acid, sulfanilic acid, tazobactam, teicoplanin, temocillin, ticarcillin, tigemonam, tosufloxacin, trovafloxacin, tyrocidine and vancomycin.

A representative example of the antibacterial agent is selected from the group comprising of amoxicillin, ampicillin, cefadroxil, cefalexin, cefixime, cefotaxime, cefuroxime, cephalexin, ciprofloxacin, gatifloxacin, nadifloxacin, nalidixic acid, norfloxacin, ofloxacin, oxacillin, panipenem, salbactam and vancomycin.

Still further, in the twelfth embodiment, the invention encompasses a compound of formula (I); wherein the antifungal agent referred to in the fourth embodiment hereinabove is selected from the group comprising of amphotericin B, azaserine, benzoic acid, candicidin, lucensomycin, natamycin, nystatin, propionic acid, salicylic acid and undecylenic acid (10-undecenoic acid).

Still further, in the thirteenth embodiment, the invention encompasses a compound of formula (I); wherein the antiviral agent referred to in the fourth embodiment hereinabove is selected from foscarnet sodium, Oseltamivir (Tamiflu) carboxylate (i.e., the parent drug of Tamiflu, which contains a free carboxylic acid group) and zanamivir.

Still further, in the fourteenth embodiment, the invention encompasses a compound of formula (I); wherein the antimalarial agent referred to in the fourth embodiment hereinabove is artesunate.

Still further, in the fifteenth embodiment, the invention encompasses a compound of formula (I); wherein the antidiabetic agent referred to in the fourth embodiment hereinabove is selected from the group comprising of mitiglinide, nateglinide, and repaglinide.

Still further, in the sixteenth embodiment, the invention encompasses a compound of formula (I); wherein the anti-ulcer agent (including proton pump inhibitors) referred to in the fourth embodiment hereinabove is selected from the group comprising of acetoxolone, arbaprostil, carbenoxolone, cetraxate, ecabet, S-methylmethionine, proglumide, rebamipide, rosaprostol, rotraxate, sofalcone and trimoprostil.

Still further, in the seventeenth embodiment, the invention encompasses a compound of formula (I); wherein the vitamin referred to in the fourth embodiment hereinabove is selected from the group comprising of biotin (vitamin H or coenzyme R), folic acid (vitamin M), menadoxime, nicotinic acid (niacin), pantothenic acid or vitamin $B_5$ (a member of the B complex vitamins).

Still further, in the eighteenth embodiment, the invention encompasses a compound of formula (I); wherein the antioxidant (including free radical scavengers) referred to in fourth, embodiment hereinabove is selected from the group comprising of α-lipoic acid, L-Carnitine, N-acetyl L-cysteine, N-acetyl carnosine, raxofelast, tetomilast, and SCMC-Lys (S-carboxymethyl-L-cysteine Lysine salt. $H_2O$).

For the purpose of this invention, the eighteenth embodiment also encompasses a compound of formula (I); wherein the drug containing carboxylic acid group is generically selected from the drugs that fall under several other therapeutic areas (including those drugs that are classified on the basis of their mechanism of action) and is specifically selected from the group comprising of an abortifacient/interceptive such as prostaglandin $E_2$; an anesthetic selected from the group comprising of ecgonidine, ecgonine, hydroxydione sodium and gamma-hydroxybutyrate (gamma-hydroxybutyric acid); an anthelmintic selected from a group comprising of antimony sodium thioglycollate, kainic acid and stibocaptate; an anti-acne agent selected from the group comprising of adapalene, isotretinoin and all-trans retinoic acid; an anti-amoebic agent selected from thiocarbamizine, and thiocarbarsone; an anti-arthritic or anti-rheumatic agent selected from the group comprising of actarit, bucillamine, diacerein, gold sodium thiomalate, lobenzarit, allocupreide sodium, clobuzarit and penicillamine; an anti-asthmatic agent selected from the group comprising of amlexanox, cilomilast (ariflo), cromolyn, domitroban, montelukast, nedocromil, ramatroban and seratrodast; an anti-gout/uricosuric agent selected from the group comprising of carprofen, probenecid, orotic acid, oxycinchophen and ticrynafen; an anti-diuretic agent such as oxycinchophen; an anti-glaucoma agent such as unoprostone; an anti-hypothyroid agent selected from tiratricol and thyroxine; an anti-prostatic hypertrophy agent such as episteride; an anti-protozoal agent selected from eflornithine or fumagillin; an anti-psoriatic agent such acitretin; an antiseptic agent such as mandelic acid; an anxiolytic agent selected from calcium n-carbamoylaspartate or clorazepic acid (i.e., clorazepate); an astringent such as bismuth subgallate; a cathartic/laxative such as sennoside; choleretic agent selected from the group comprising of cholic acid, cicrotoic acid, clanobutin, cyclobutyrol, cynarin(e), dehydrocholic acid, deoxycholic acid, dimecrotic acid, exiproben, fencibutirol, florantyrone, menbutone, 3-(o-methoxyphenyl)-2-phenylacrylic acid, sincalide, tocamphyl and trepibutone; an enzyme cofactor such as pantothenic acid; an estrogen such as methallenestril; a gastroprokinetic agent selected from alvimopan or loxiglumide; a hemostatic agent selected from ε-aminocaproic acid or tranexamic acid; a hepatoprotectant selected from the group comprising of S-adenosyl methionine, betaine, orazamide, timonacic (thioproline), methionine, protoporphyrin IX, thioctic acid and tiopronin; an immunomodulator selected from the group comprising of bucillamine, ubenimex, pidotimod, procodazole, romurtide and thymopentin; immunosuppressant selected from brequinar or mycophenolic acid; a mucolytic selected from the group comprising of acetylcysteine, carbocysteine, erdosteine, letosteine and stepronin; a muscle relaxant such as baclofen; a nootropic/cognitive enhancer selected from the group comprising of acetylcarnitine, hexacyclonate sodium and leteprinim; a prostaglandin analog selected from the group comprising of beraprost, carboprost, limaprost, prostacyclin, prostaglandin $E_1$, prostaglandin $E_2$, prostaglandin $F_{2\alpha}$, rosaprostol, sulprostone, trimoprostil and unoprostone; a sedative/hypnotic chloral selected from betainem or calcium 2-ethylbutanoate; a dopamine receptor agonist such as carmoxirole; a 5α-Reductase inhibitor such as epristeride; a reverse transcriptase inhibitor such as foscarnet sodium; thromboxane $A_2$-receptor antagonist selected from the group comprising of altroban, domitroban, ramatroban, ridogrel and seratrodast and a thromboxane $A_2$-synthase inhibitor selected from the group comprising of isbogrel, ozagrel and ridogrel.

Still further, in the nineteenth embodiment, is provided a pharmaceutical composition comprising a therapeutically effective amount of a compound of formula (I) and a therapeutically effective amount of an anti-ulcer agent such as a proton-pump inhibitor (PPI) or a H2 receptor antagonist (especially for chronic NSAID use), and a pharmaceutically acceptable carrier.

It is well known that long-term NSAID users are at increased risk of stomach ulcers, which is often a deterrent to long-term treatment. Acid control can reduce this risk and concomitant use of an anti-ulcer agent such as a proton pump inhibitor or a H2 receptor antagonist can thus be beneficial in reducing the incidence of ulcers associated with chronic NSAID use.

Thus, in the above embodiment, is provided a pharmaceutical composition comprising a therapeutically effective amount of a compound of formula (I) that are derived from known anti-inflammatory agents such as aspirin, naproxen, diclofenac, indomethacin, ibuprofen and the like and a therapeutically effective amounts of an anti-ulcer agent such as a proton-pump inhibitor (PPI) or a H2 receptor antagonist (especially for chronic NSAID use), and a pharmaceutically acceptable carrier.

A representative example of the proton-pump inhibitor (PPI) is selected from the group comprising of omeprazole, esomeprazole, lansoprazole, rabeprazole, pantoprazole, tenatoprazole and ilaprazole. Included within these examples are salts, isomers, racemic compounds, crystals, polymorphs, amorphous forms and cocrystals of these examples.

A representative example of the H2 receptor antagonist is selected from the group comprising of cimetidine, famotidine, nizatidine and ranitidine. Included within these examples are salts, isomers, racemic compounds, crystals, polymorphs, amorphous forms and cocrystals of these examples.

It is understandable to those skilled in the art to whom this invention relates that the only requirement for a drug or therapeutic agent to qualify itself as a suitable candidate for conversion to a compound of the invention, irrespective of its structural complexity or therapeutic use or mechanism of action, is the presence of at least one carboxylic acid functional group in its structure. Thus, in an embodiment, the following prophetic examples are provided to amply illustrate the scope of the invention covering/encompassing the compounds of formula (I), wherein, the groups Ry, $^h$PG, $^s$PG, $^c$PG, $^a$PG and $^p$PG are same as defined in the forgoing embodiments:

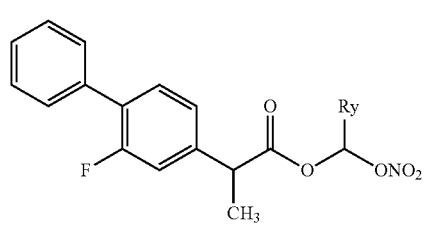

(NO-Flurbiprofen-An NSAID)

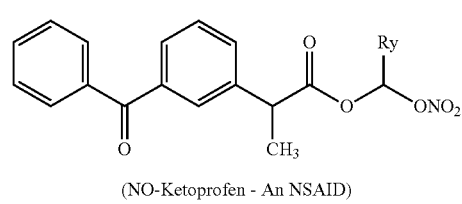

(NO-Ketoprofen - An NSAID)

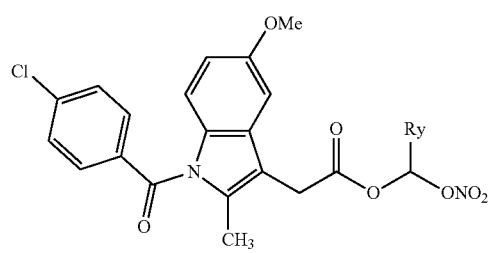

(NO-Indomethacin - An NSAID)

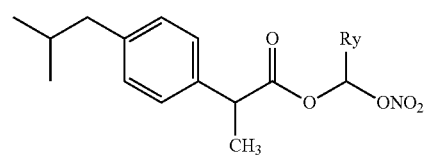

(NO-Ibuprofene - An NSAID)

-continued

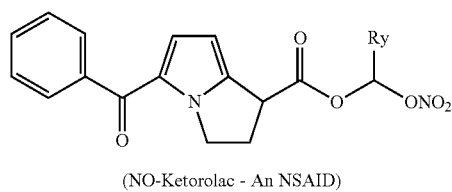
(NO-Ketorolac - An NSAID)

I-D8-Ry

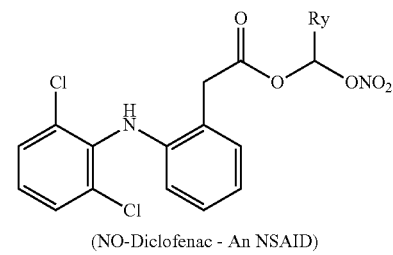
(NO-Diclofenac - An NSAID)

I-D9-Ry

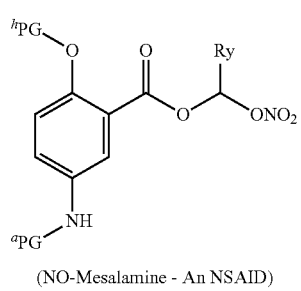
(NO-Mesalamine - An NSAID)

I-D10-R1

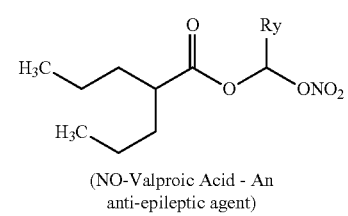
(NO-Valproic Acid - An anti-epileptic agent)

I-D11-Ry

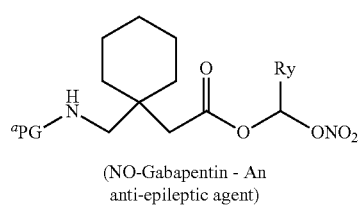
(NO-Gabapentin - An anti-epileptic agent)

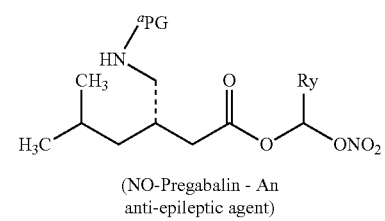
(NO-Pregabalin - An anti-epileptic agent)

I-D12-Ry

I-D13-Ry

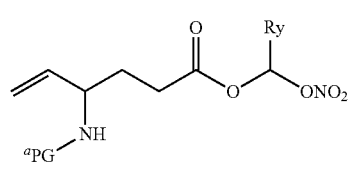
(NO-Vigabatrin - An anti-epileptic agent)

I-D14-Ry

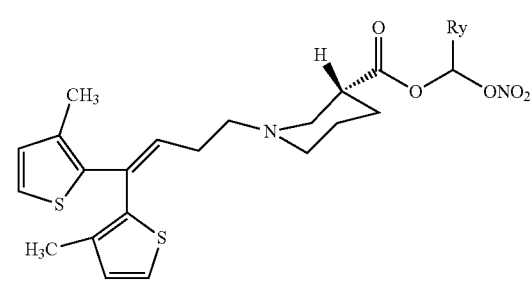
(NO-Tiagabine - An anti-epileptic agent)

I-D15-Ry

I-D16-Ry

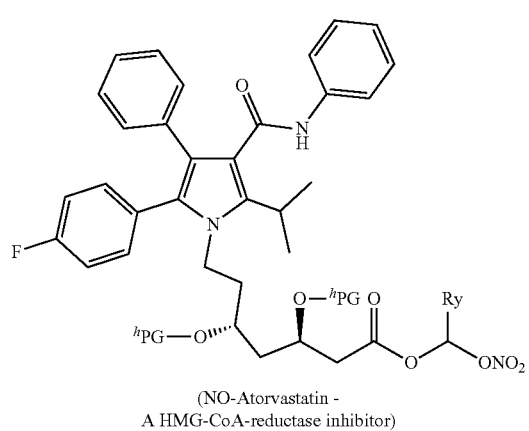
(NO-Atorvastatin - A HMG-CoA-reductase inhibitor)

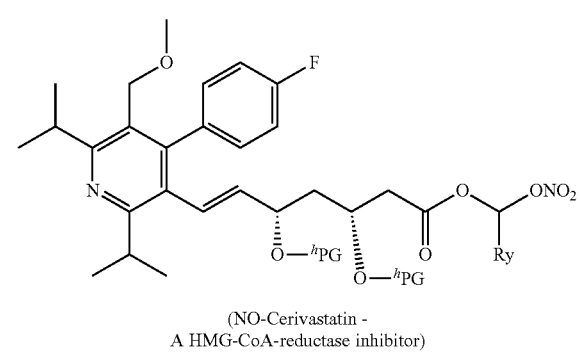
(NO-Cerivastatin - A HMG-CoA-reductase inhibitor)

I-D17-Ry

-continued

I-D18-Ry
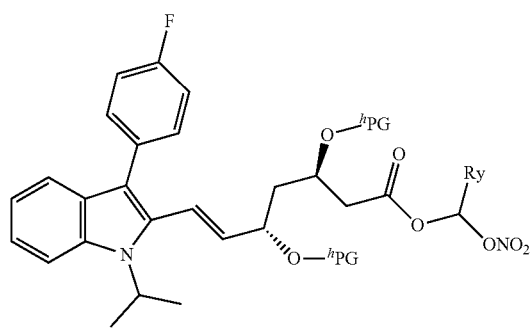
(NO-Fluvastatin -
A HMG-CoA-reductase inhibitor)

I-D19-Ry
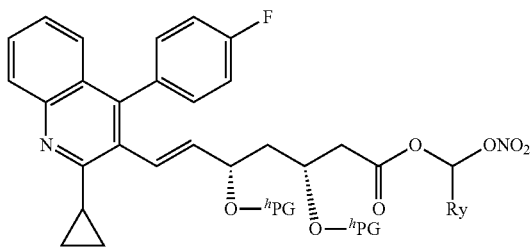
(NO-Pitavastatin -
A HMG-CoA-reductase inhibitor)

I-D20-Ry
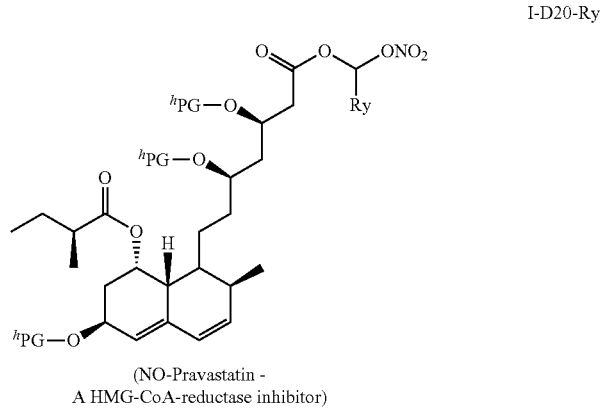
(NO-Pravastatin -
A HMG-CoA-reductase inhibitor)

I-D21-Ry
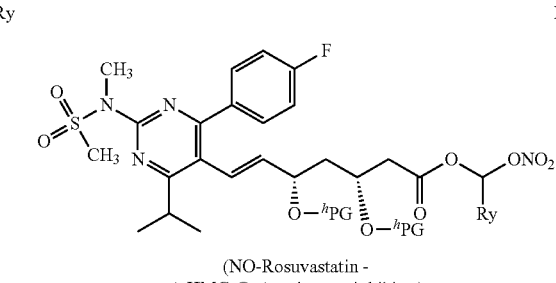
(NO-Rosuvastatin -
A HMG-CoA-reductase inhibitor)

I-D22-Ry
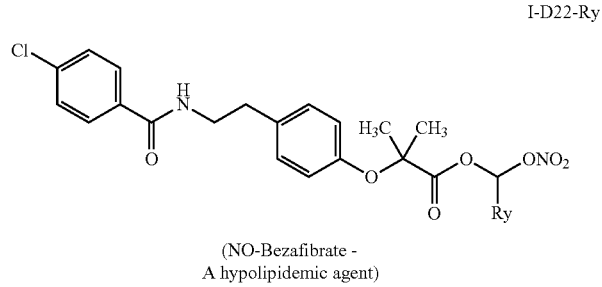
(NO-Bezafibrate -
A hypolipidemic agent)

I-D23-Ry
(NO-Ciprofibrate -
A hypolipidemic agent)

I-D24-Ry
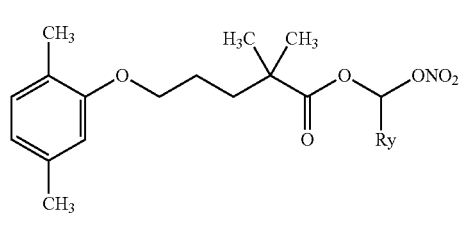
(NO-Gemfibrozil - A hypolipidemic agent)

I-D25-Ry
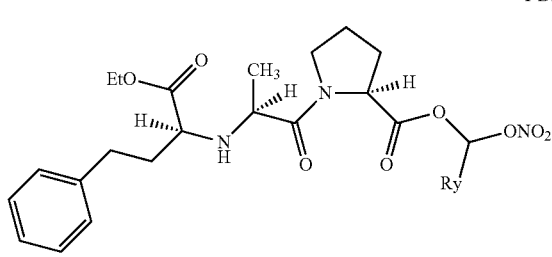
(NO-Enalapril - An ACE inhibitor)

-continued

I-D26-Ry

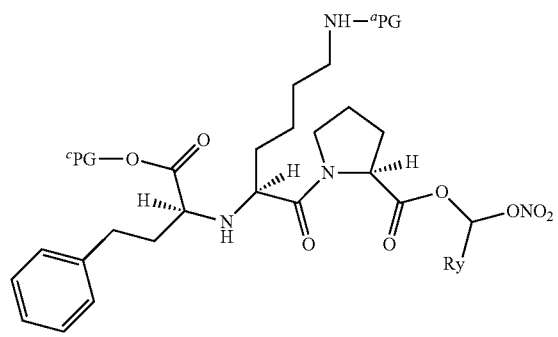

(NO-Lisinopril - An ACE inhibitor)

I-D27-Ry

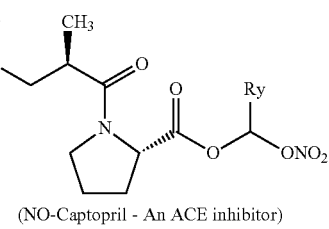

(NO-Captopril - An ACE inhibitor)

I-D28-Ry

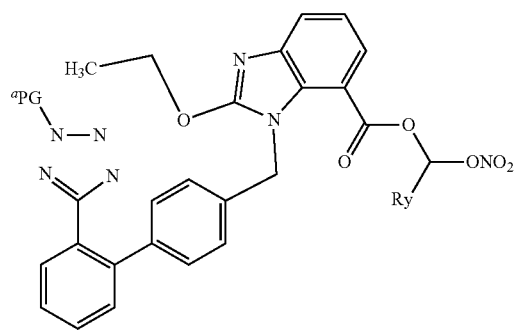

(NO-Candesartan - An angiotensin II receptor antagonist)

I-D29-Ry

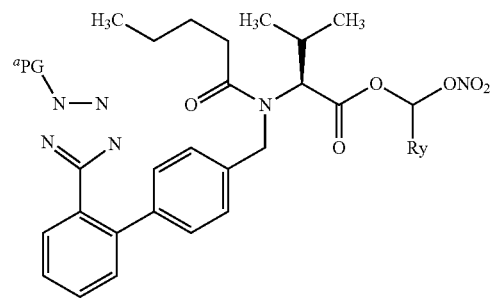

(NO-Valsartan - An angiotensin II receptor antagonist)

I-D30-Ry

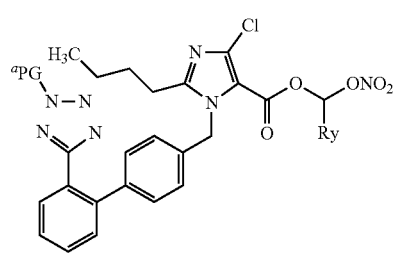

[NO-Losartan acid (EXP-3174) - An angiotensin II receptor antagonist]

I-D31-Ry

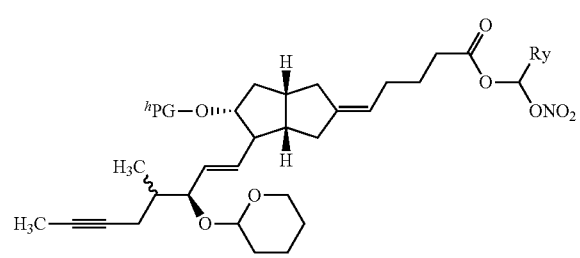

(NO-Iloprost - A vasodilator)

I-D32-Ry

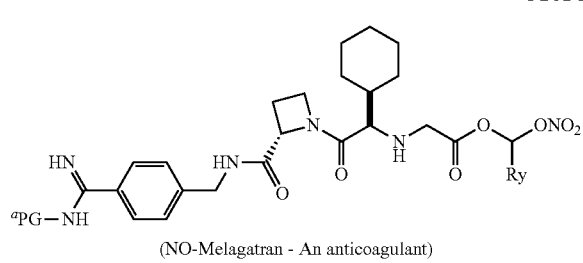

(NO-Melagatran - An anticoagulant)

I-D33-Ry

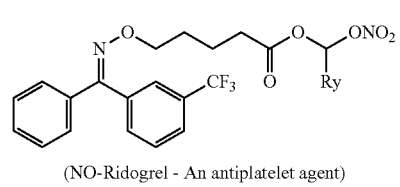

(NO-Ridogrel - An antiplatelet agent)

I-D34-Ry

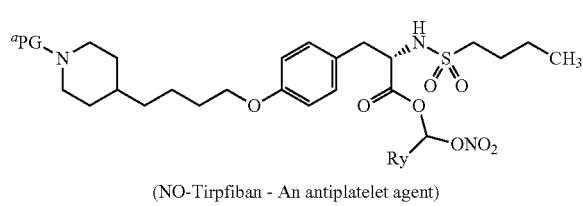

(NO-Tirpfiban - An antiplatelet agent)

I-D35-Ry

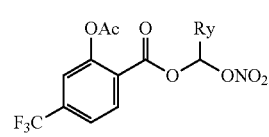

(NO-Triflusal - An antiplatelet agent)

-continued

I-D36-Ry
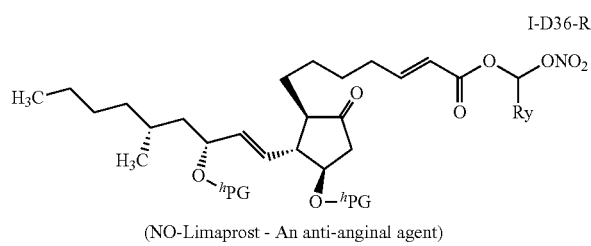
(NO-Limaprost - An anti-anginal agent)

I-D37-Ry
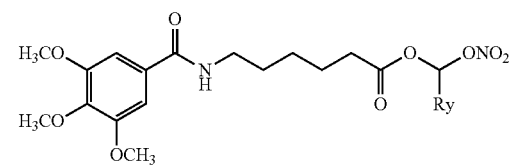
(NO-Capobenic acid - An anti-arrhythmic agent)

I-D38-Ry
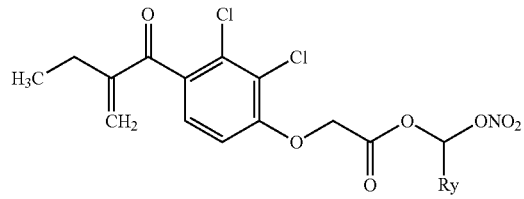
(NO-Etacrynic acid - A diuretic agent)

I-D39-Ry
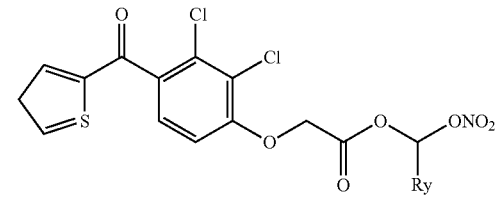
(NO-Ticrynafen - A diuretic agent)

I-D40-Ry
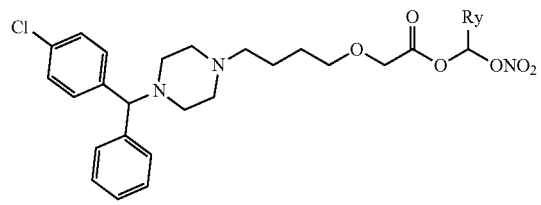
(NO-Cetirizine - An anti-histamine)

I-D41-Ry
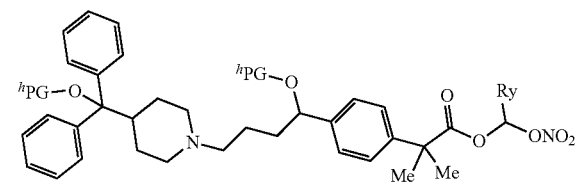
(NO-Fexofenadine - An anti-histamine)

I-D42-Ry
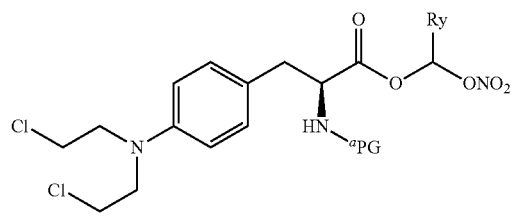
(NO-Mephalan - An anticancer agent)

I-D43-Ry
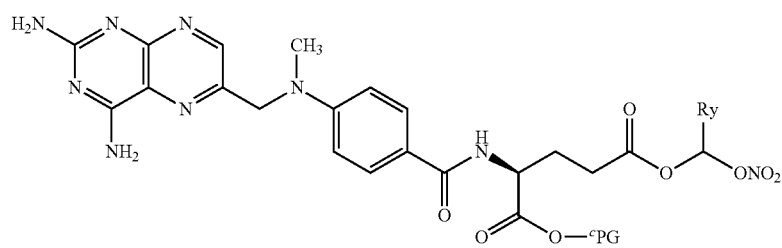
(NO-Methotrexate - An anticancer agent)

I-D44-Ry
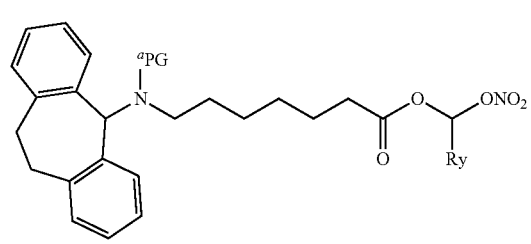
(NO-Amineptine - An antidepressnat)

I-D45-Ry
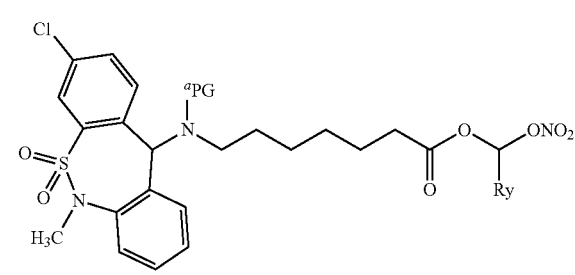
(NO-Tianeptine - An antidepressnat)

-continued
I-D46-Ry
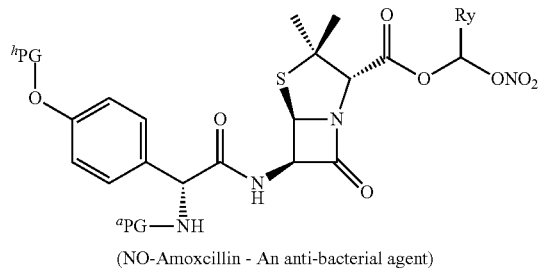
(NO-Amoxcillin - An anti-bacterial agent)
I-D47-Ry
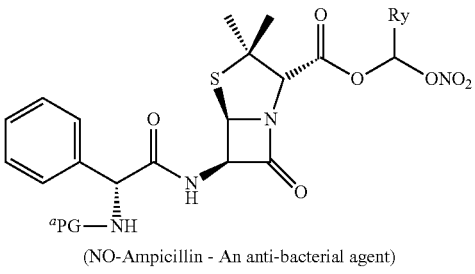
(NO-Ampicillin - An anti-bacterial agent)
I-D48-Ry
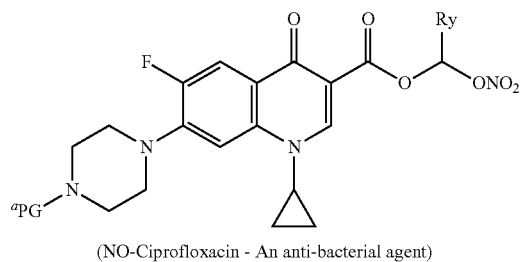
(NO-Ciprofloxacin - An anti-bacterial agent)
I-D49-Ry
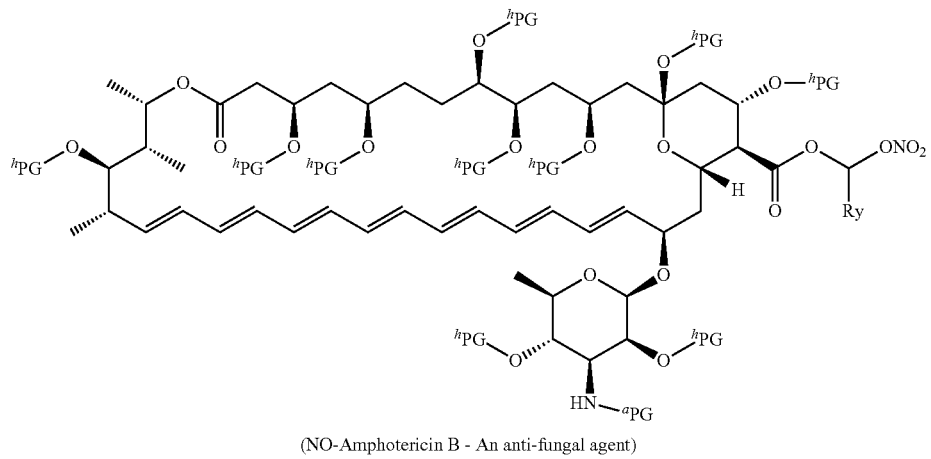
(NO-Amphotericin B - An anti-fungal agent)
I-D50-Ry
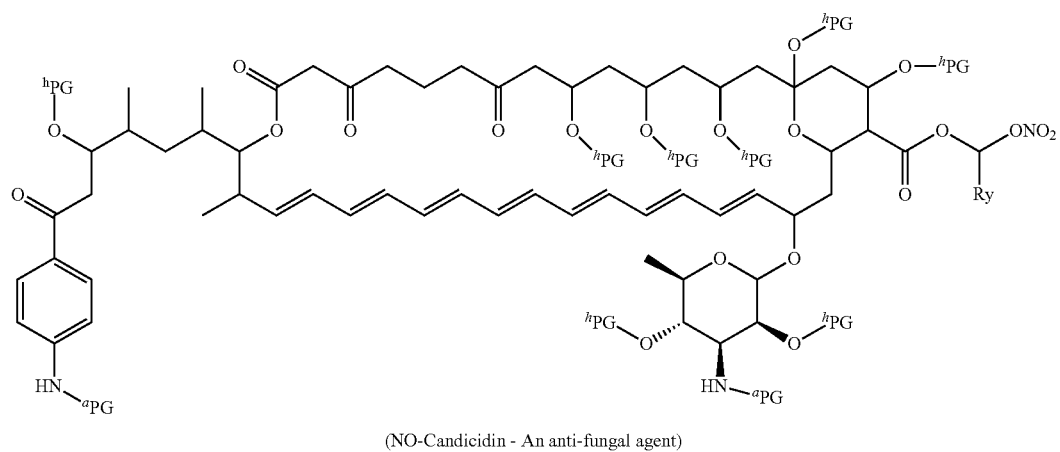
(NO-Candicidin - An anti-fungal agent)

-continued

I-D51-Ry
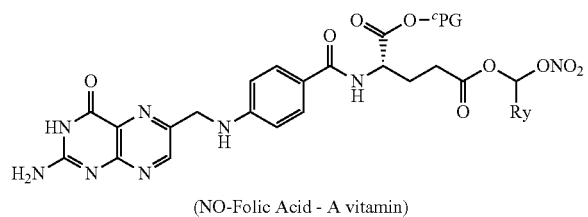
(NO-Folic Acid - A vitamin)

I-D52-Ry
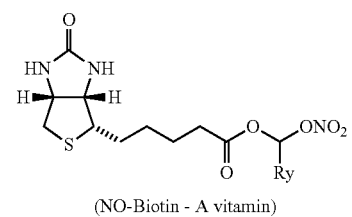
(NO-Biotin - A vitamin)

I-D53-Ry
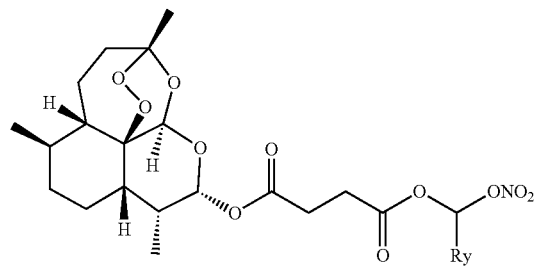
(NO-Artesunate - An anti-malarial agent)

I-D54-Ry
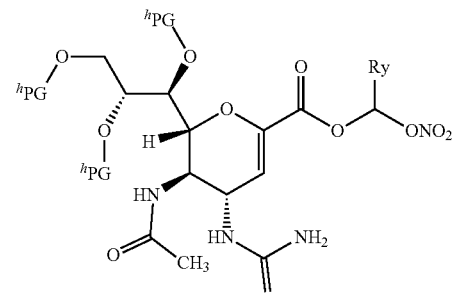
(NO-Zanamivir - An anti-viral agent)

I-D55-Ry
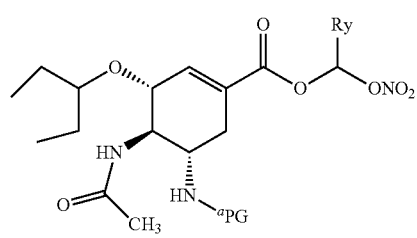
(NO-Oseltamivir (Tamiflu) carboxylate - An anti-influenza drug)

I-D56-Ry
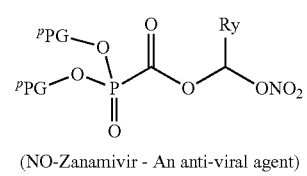
(NO-Zanamivir - An anti-viral agent)

I-D57-Ry
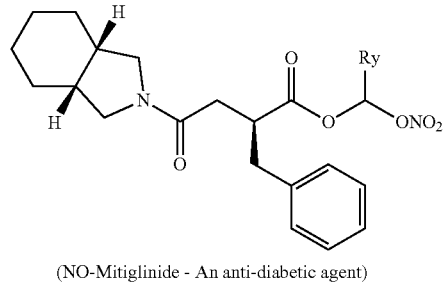
(NO-Mitiglinide - An anti-diabetic agent)

I-D58-Ry
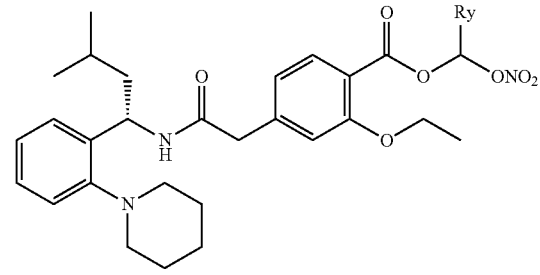
(NO-Repaglinide - An anti-diabetic agent)

I-D59-Ry
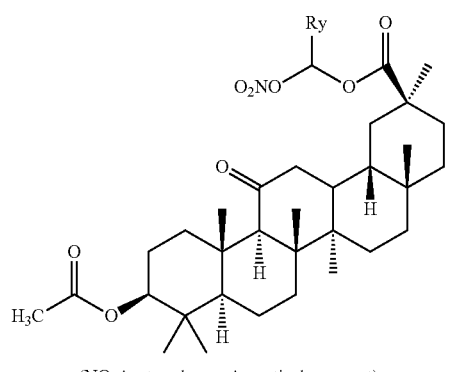
(NO-Acetoxolone - An anti-ulcer agent)

I-D60-Ry
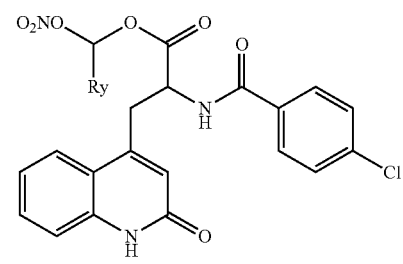
(NO-Rebamipide - An anti-ulcer agent)

-continued

I-D61-Ry

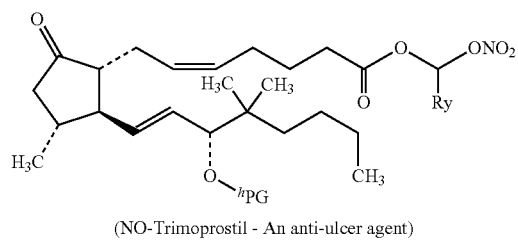
(NO-Trimoprostil - An anti-ulcer agent)

I-D62-Ry

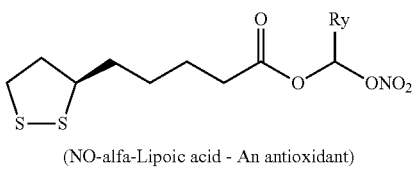
(NO-alfa-Lipoic acid - An antioxidant)

I-D63-Ry

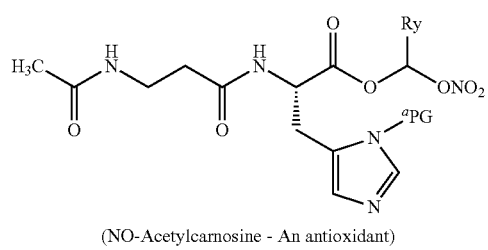
(NO-Acetylcarnosine - An antioxidant)

I-D64-Ry

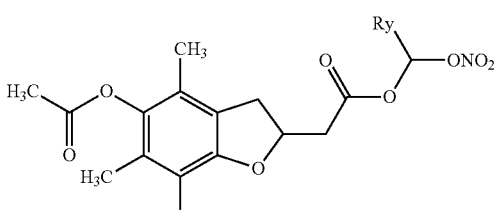
(NO-Raxofelast - An antioxidant)

I-D65-Ry

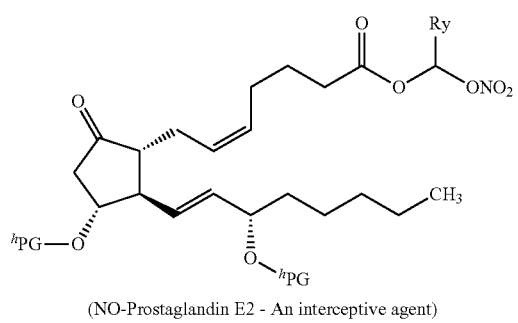
(NO-Prostaglandin E2 - An interceptive agent)

I-D66-Ry

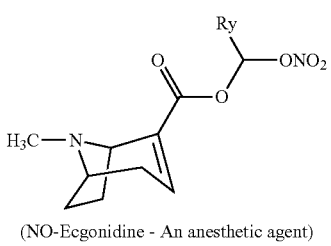
(NO-Ecgonidine - An anesthetic agent)

I-D67-Ry

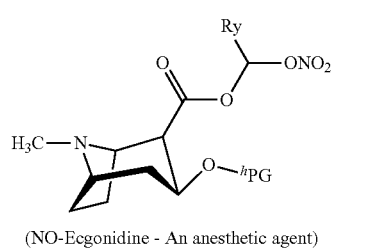
(NO-Ecgonidine - An anesthetic agent)

I-D68a-Ry

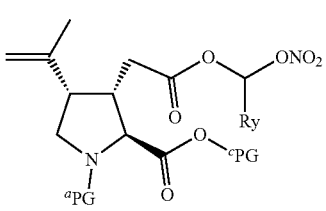
(NO-Kainic acid - An anthelmintic agent)    and/or

I-D68b-Ry

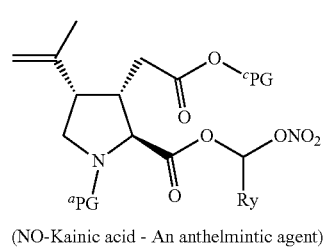
(NO-Kainic acid - An anthelmintic agent)

I-D69-Ry

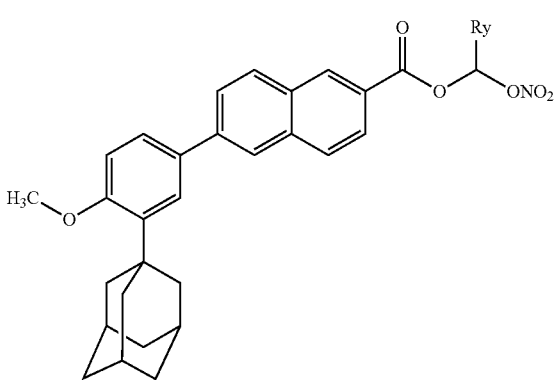
(NO-Adapalene - An anti-acne agent)

-continued

I-D70-Ry

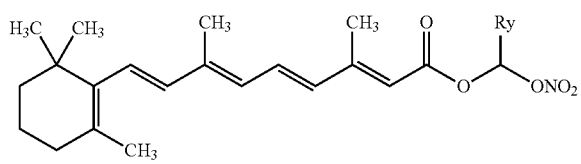

(NO-All-trans-retinoic acid - An anti-acne agent)

I-D71-Ry

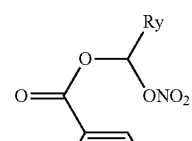

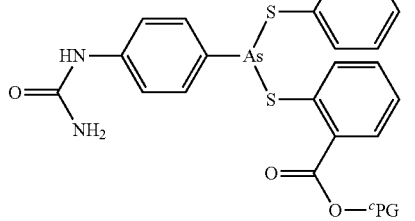

(NO-Thiocarbamizine - An anti-amoebic agent)

I-D72-Ry

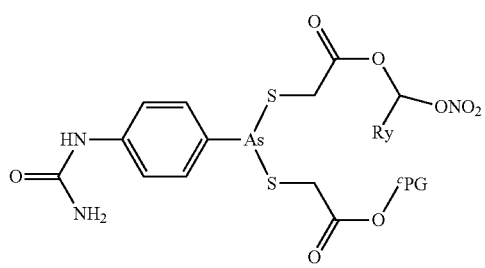

(NO-Thiocarbarsone - An anti-amoebic agent)

I-D73-Ry

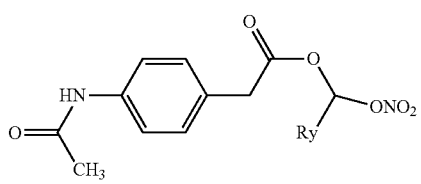

(NO-Actarit - An anti-arthritic agent)

I-D74-Ry

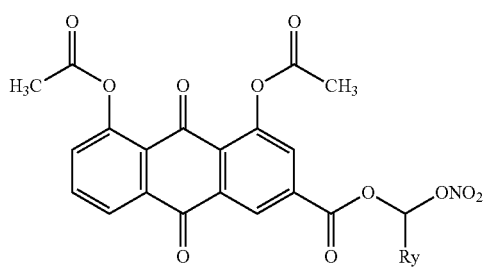

(NO-Diacerein - An anti-arthritic agent)

I-D75-Ry

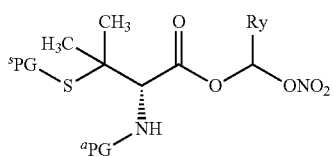

(NO-Penicillamine - An anti-arthritic agent)

I-D76-Ry

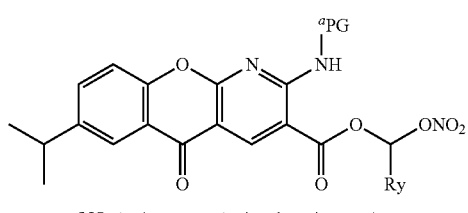

(NO-Amlexanox - Anti-asthmatic agent)

I-D77-Ry

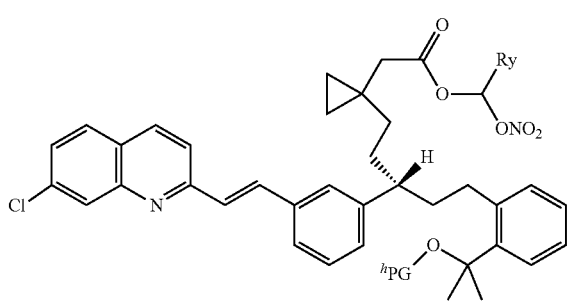

(NO-Montelukast - An anti-asthmatic agent)

-continued

I-D78-Ry
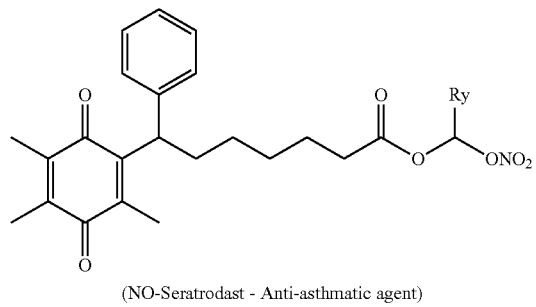
(NO-Seratrodast - Anti-asthmatic agent)

I-D79-Ry
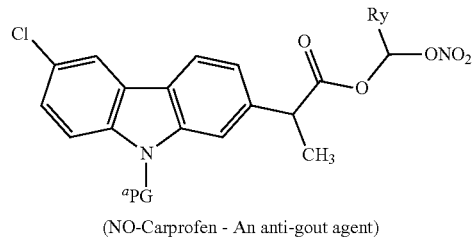
(NO-Carprofen - An anti-gout agent)

I-D80-Ry
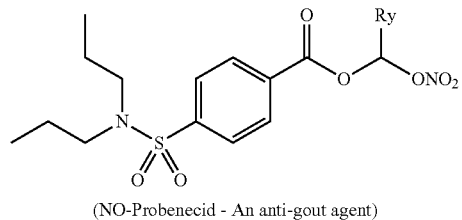
(NO-Probenecid - An anti-gout agent)

I-D81-Ry
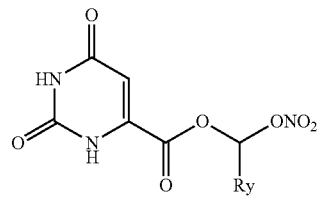
(NO-Orotic acid - An anti-gout agent)

I-D82-Ry
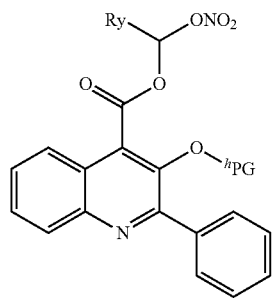
(NO-Oxycinchophen - An anti-diuretic agent)

I-D83-Ry
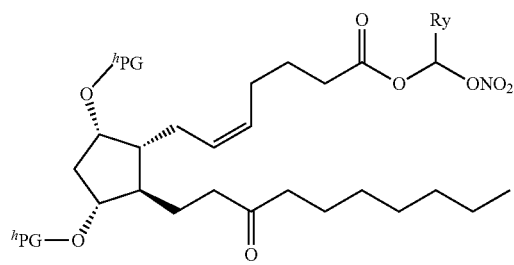
(NO-Unoprostone - An anti-glaucoma agent)

I-D84-Ry
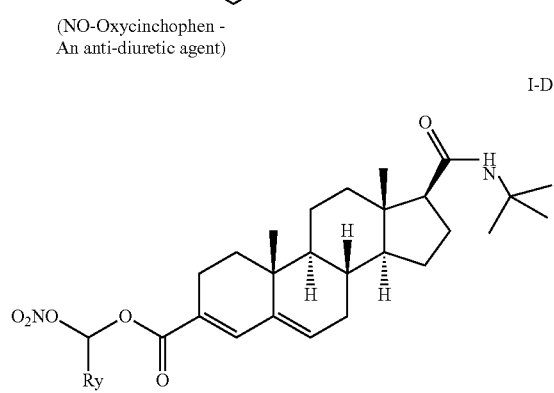
(NO-Epristeride - An anti-prostatic hypertrophy agent)

I-D85-Ry
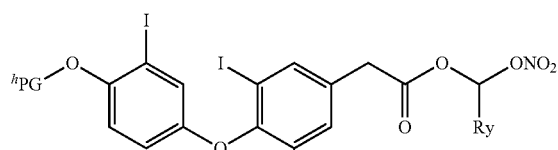
(NO-Tiratricol - An anti-hypothyroid agent)

I-D86-Ry
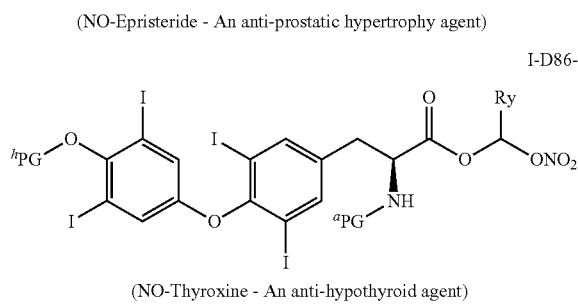
(NO-Thyroxine - An anti-hypothyroid agent)

I-D87-Ry
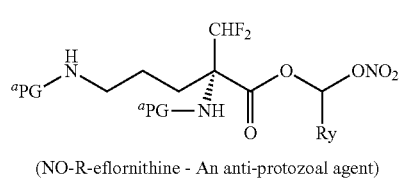
(NO-R-eflornithine - An anti-protozoal agent)   and

-continued
I-D88-Ry
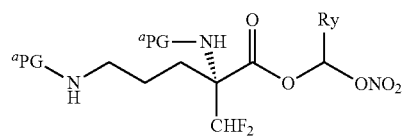
(NO-S-eflornithine - An anti-protozoal agent)
I-D89-Ry
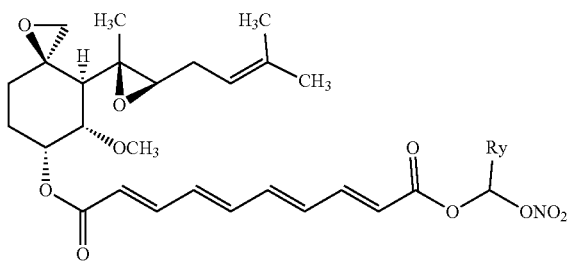
(NO-Fumagillin - An anti-protozoal agent)
I-D90-Ry
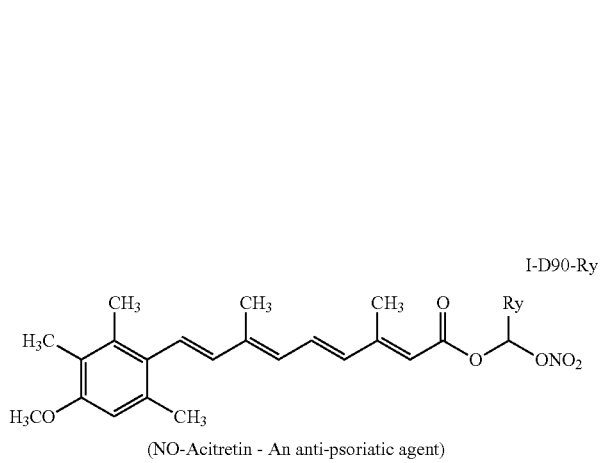
(NO-Acitretin - An anti-psoriatic agent)
I-D91-Ry
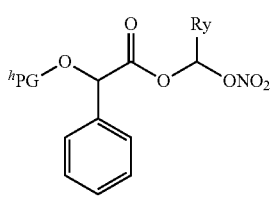
(NO-Mandelic acid - An anti-septic agent)
I-D92-Ry
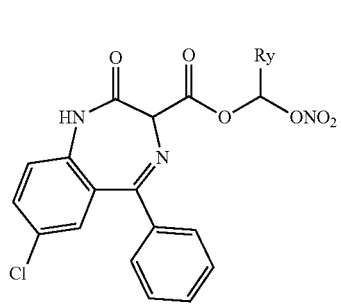
(NO-Clorazepate - An anxiolytic agent)
I-D93a-Ry
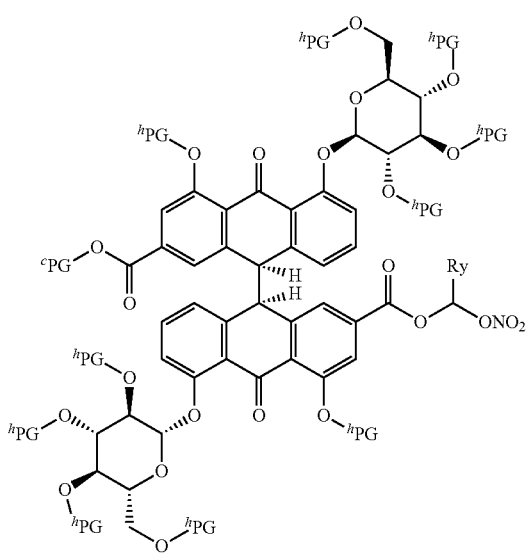
and/or
(NO-Sennoside - A laxative agent)

-continued
I-D93b-Ry
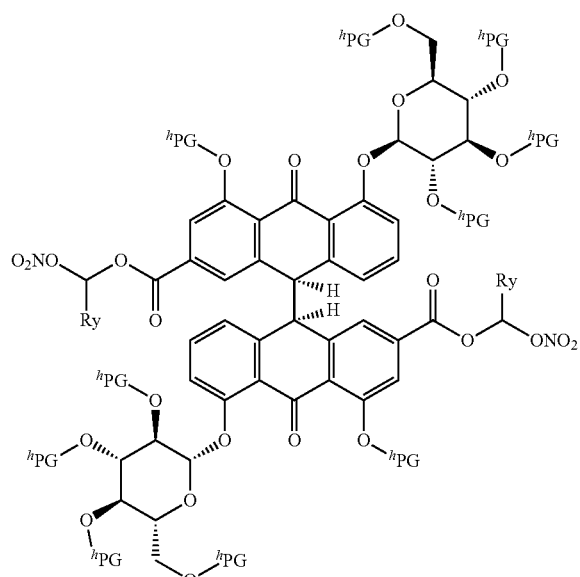
(NO-Sennoside - A laxative agent)
I-D94-Ry
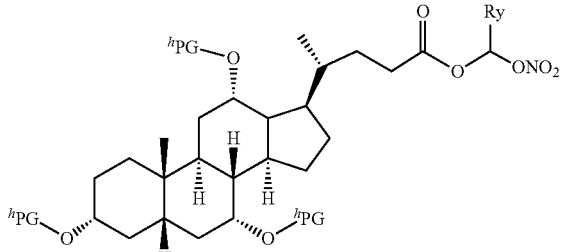
(NO-Cholic acid - A choleretic agent)
I-D95-Ry
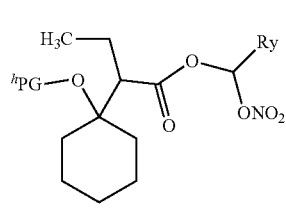
(NO-Cyclobutyrol -
A choleretic agent)
I-D96-Ry
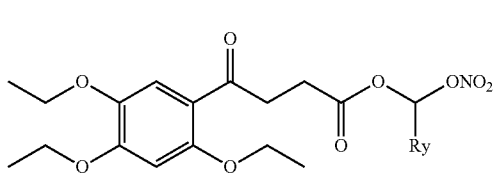
(NO-Trepibutone - A choleretic agent)
I-D97-Ry
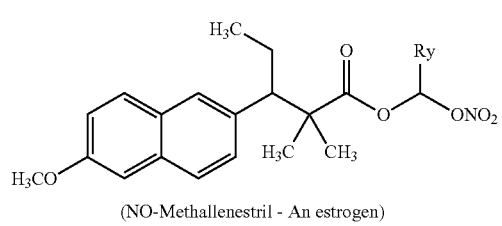
(NO-Methallenestril - An estrogen)
I-D98-Ry
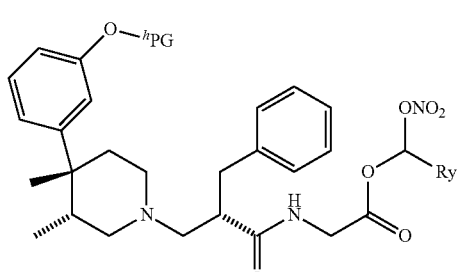
(NO-Alvimopan - A gastroprokinetic agent)
I-D99-Ry
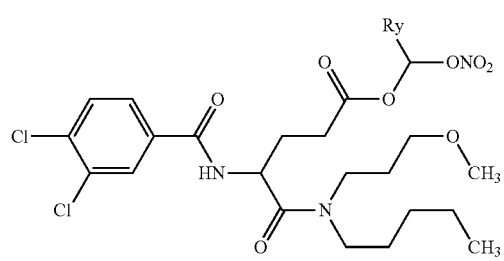
(NO-Loxiglumide - A gastroprokinetic agent)
I-D100-Ry
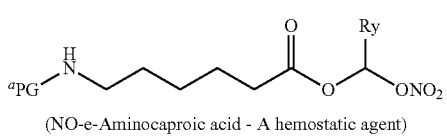
(NO-e-Aminocaproic acid - A hemostatic agent)

-continued

I-D101-Ry
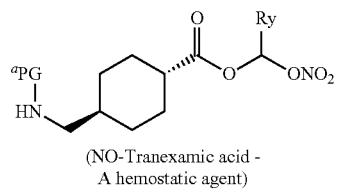
(NO-Tranexamic acid - A hemostatic agent)

I-D102-Ry
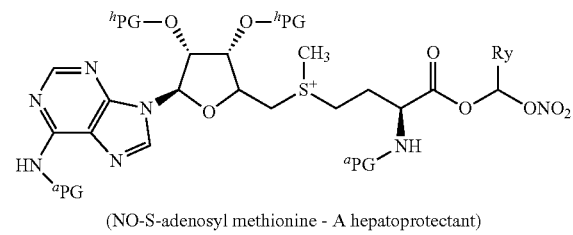
(NO-S-adenosyl methionine - A hepatoprotectant)

I-D103-Ry
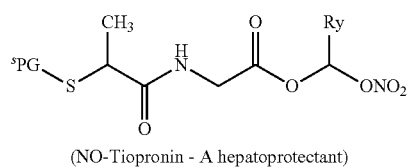
(NO-Tiopronin - A hepatoprotectant)

I-D104-Ry
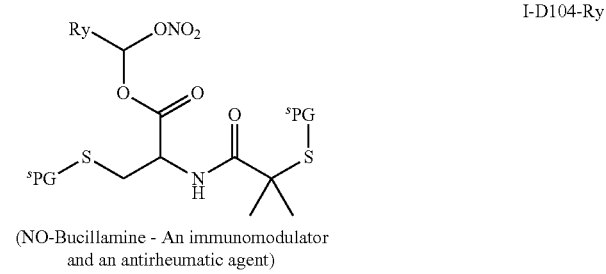
(NO-Bucillamine - An immunomodulator and an antirheumatic agent)

I-D105-Ry
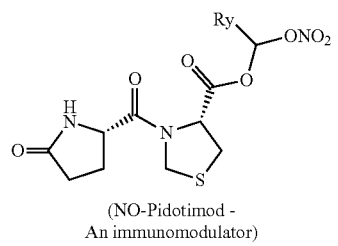
(NO-Pidotimod - An immunomodulator)

I-D106-Ry
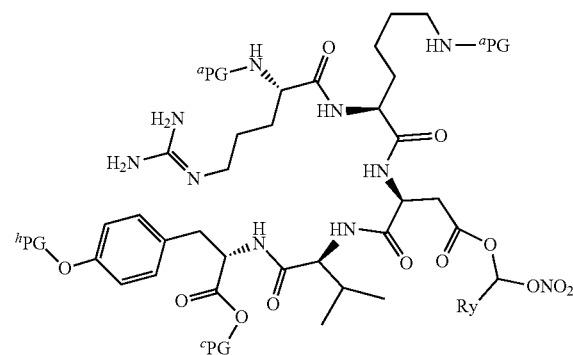
(NO-Thymopentin - An immunostimulator)

I-D107-Ry
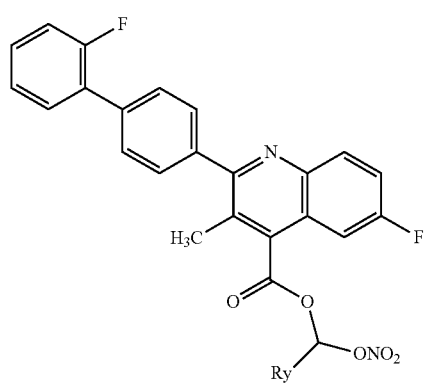
(NO-Brequinar - An immunosuppressant)

I-D108-Ry
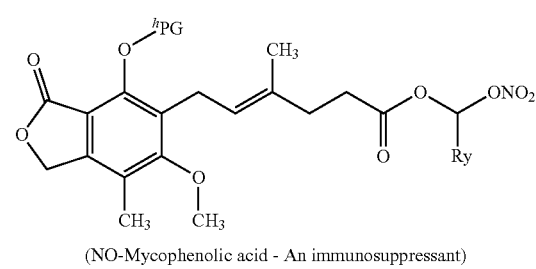
(NO-Mycophenolic acid - An immunosuppressant)

I-D109-Ry
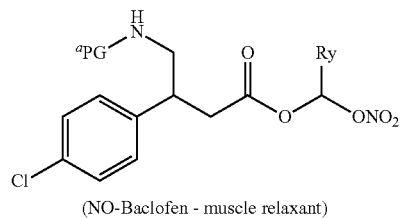
(NO-Baclofen - muscle relaxant)

I-D110-Ry
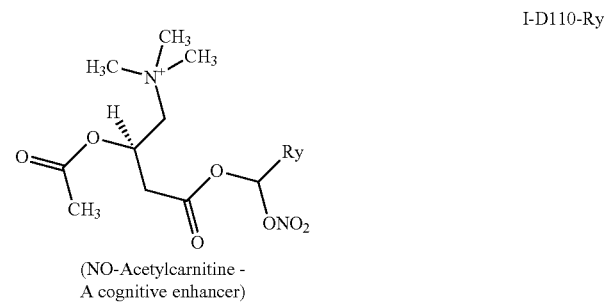
(NO-Acetylcarnitine - A cognitive enhancer)

-continued

I-D111a-Ry

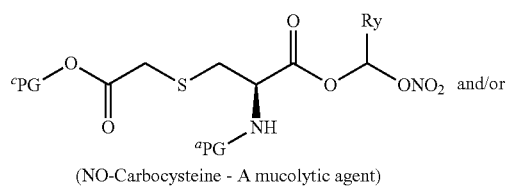

(NO-Carbocysteine - A mucolytic agent)

and/or

I-D111b-Ry

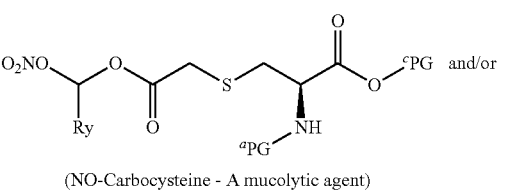

(NO-Carbocysteine - A mucolytic agent)

and/or

I-D111c-Ry

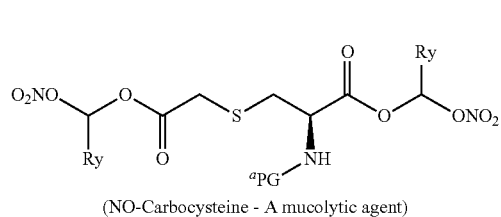

(NO-Carbocysteine - A mucolytic agent)

I-D112-Ry

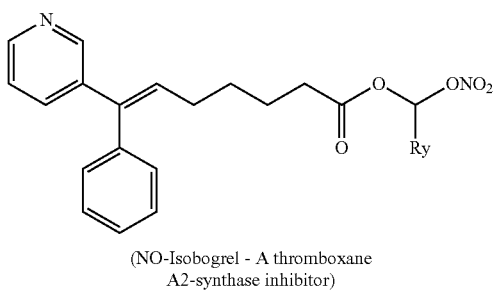

(NO-Isobogrel - A thromboxane A2-synthase inhibitor)

I-D113-Ry

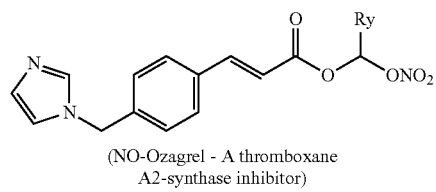

(NO-Ozagrel - A thromboxane A2-synthase inhibitor)

I-D114-Ry

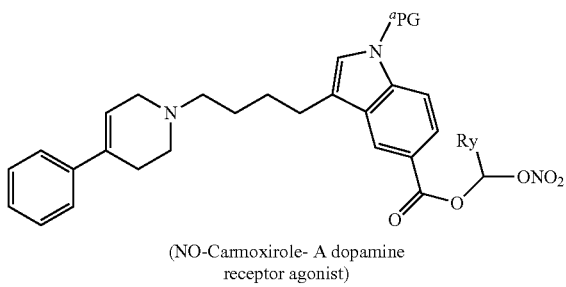

(NO-Carmoxirole- A dopamine receptor agonist)

I-D115-Ry

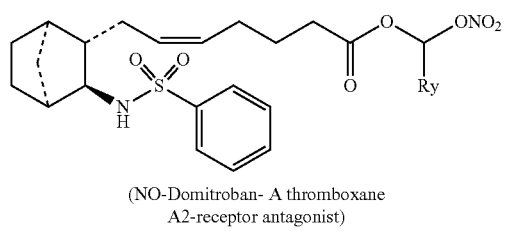

(NO-Domitroban- A thromboxane A2-receptor antagonist)

I-D116-Ry

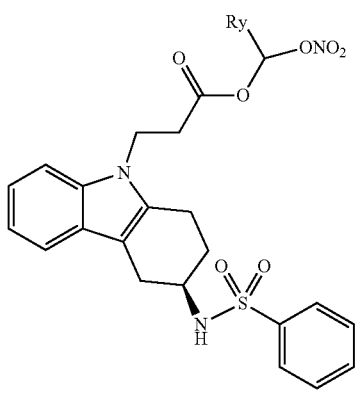

(NO-Ramatroban- A thromboxane A2-receptor antagonist)

and all their geometrical and stereoisomeric forms and also pharmaceutically acceptable salts thereof;

In a specific embodiment, the invention encompasses a compound of formula (I) selected from the list comprising of:

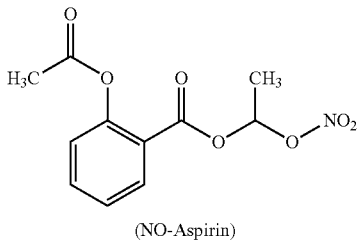
(NO-Aspirin) I-D1-R1

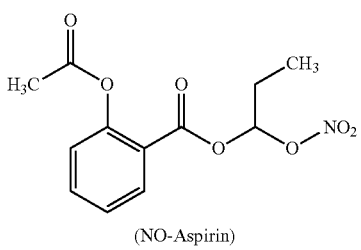
(NO-Aspirin) I-D1-R2

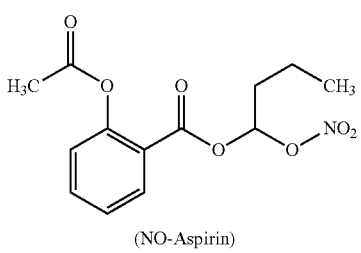
(NO-Aspirin) I-D1-R3

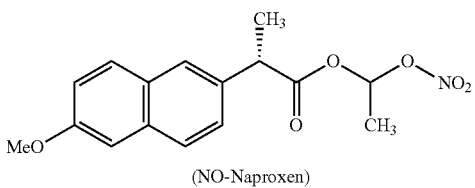
(NO-Naproxen) I-D2-R1

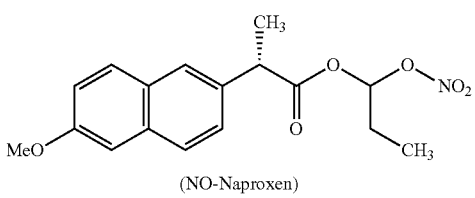
(NO-Naproxen) I-D2-R2

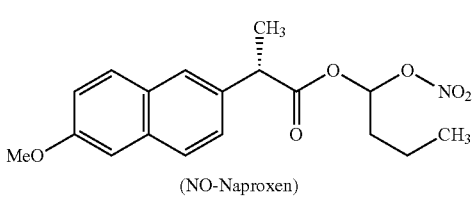
(NO-Naproxen) I-D2-R3

-continued

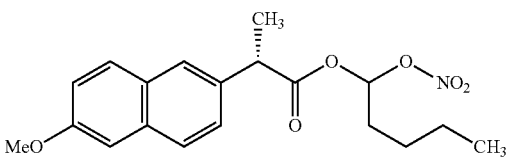
(NO-Naproxen) I-D2-R4

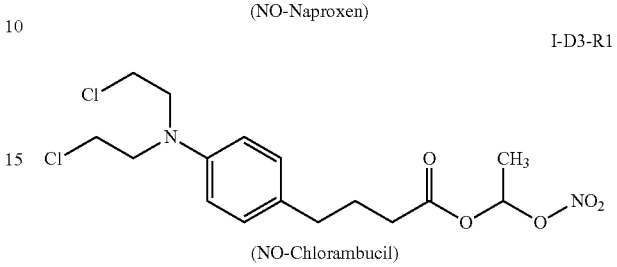
(NO-Chlorambucil) I-D3-R1 and their geometrical and stereoisomeric forms and also pharmaceutically acceptable salts thereof;

The compounds of formula (I) may contain a double bond, an asymmetric or a chiral center either in the linker in the drug molecule, and therefore can exist in different geometrical and stereoisomeric forms. In the structures shown herein, where the stereochemistry of any particular chiral atom is not specified, then all stereoisomers are contemplated and included as the compounds of the invention. The term "chiral" refers to molecules which have the property of non-superimposability of the mirror image cohort, while the term "achiral" refers to molecules which are superimposable on their mirror image partner. It is intended that all stereoisomeric forms of the compounds of formula (I) of the invention, including but not limited to, diastereomers (when a parent drug, like in naproxen, contains a chiral centre) and enantiomers, as well as mixtures thereof such as racemic mixtures, form part of the present invention. Thus, compound of formula (I) according to the present invention can exist as enantiomers, can be present in enantiomerically pure form, both as levorotatory and as dextrorotatory antipodes, in the form of racemates and in the form of mixtures of the two enantiomers in all ratios. In the case of cis/trans isomerism the compound of formula (I) includes cis or trans forms or mixtures of these forms in all ratios; preferably exists either in cis form or trans form. The preparation of individual enantiomer or diastereomer from the racemates of the compounds of the present invention represented by the formula (I) can be carried out, if desired, by separation methods known in the art. For instance, the racemic forms can be resolved by physical methods, such as fractional crystallisation or separation by chiral column chromatography. The individual optical isomers can be synthesized in the optically pure form by the use of enzymes or through asymmetric syntheses. If, for instance, a particular enantiomer of the compound of formula (I) of the present invention is desired, it may be prepared by derivatisation with a chiral auxiliary whereby the resulting diastereomeric mixture is separated and the auxiliary group cleaved to provide the pure desired enantiomer. In case, the compound of formula (I) contains additional basic functional group such as amino or an acidic functional group such as carboxyl, diastereomeric salts are formed with an appropriate optically active acid or base, respectively. Consequently, compounds of formula (I) can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic techniques or fractional crystallization.

Unless it is specifically desired, the racemic or diastereomeric mixture of compounds of the invention represented by the formula (I) can be used without resolving as the chirality resides in the linker portion and the linker would be cleaved off either chemically or enzymatically, or by both means, to liberate the parent drug in its original form in vivo.

One aspect of the invention includes a pharmaceutical composition comprising a therapeutically effective amount of the compound of formula (I), or a pharmaceutically acceptable salt thereof and one or more of pharmaceutically acceptable carriers, vehicles or diluents.

Another aspect of the invention includes a method of treating a disease or disorder in a human or mammal where a chronic, sustained and selective release of the constituent drug or therapeutic agent and/or nitric oxide from a compound of formula (I) is beneficial; comprising administering to a mammal or a human in need of the treatment a therapeutically effective amount of the compound of formula (I).

Yet another aspect of the invention includes a method of treating a disease or disorder in a human or mammal where a chronic, sustained and selective release of the constituent drug or therapeutic agent or nitric oxide is beneficial; comprising administering to said mammal a therapeutically effective amount of the pharmaceutical composition containing a compound of the formula (I).

In one aspect of the invention, the compounds of formula (I) as mentioned in any one of the preceding embodiments for use in the treatment of a disease or disorder where a chronic, sustained and selective release of the constituent drug or therapeutic agent and nitric oxide contained in the compounds of formula (I) is beneficial.

In another aspect of the invention, the pharmaceutical composition according to the relevant preceding embodiments for use in the treatment of a disease or disorder where a chronic, sustained and selective release of the constituent drug or therapeutic agent and nitric oxide contained in the compounds of formula (I) is beneficial.

Another aspect of the invention includes use of the compounds of formula (I) as mentioned in any one of the preceding embodiments for the treatment of a disease or disorder where a chronic, sustained and selective release of the constituent drug or therapeutic agent and nitric oxide contained in the compounds of formula (I) is beneficial.

Yet another aspect of the invention includes use of the pharmaceutical composition as mentioned in relevant preceding embodiments for the treatment of a disease or disorder where a chronic, sustained and selective release of the constituent drug or therapeutic agent and nitric oxide contained in the compounds of formula (I) is beneficial.

Yet another aspect of the invention includes use of the compounds of formula (I) as mentioned in any one of the preceding embodiments for the manufacture of medicaments for the treatment of a disease or disorder where a chronic, sustained and selective release of the constituent drug or therapeutic agent and nitric oxide contained in the compounds of formula (I) is beneficial.

Yet another aspect of the invention includes use of the pharmaceutical composition as mentioned in preceding embodiments for the manufacture of medicaments for the treatment of a disease or disorder where a chronic, sustained and selective release of the constituent drug or therapeutic agent and nitric oxide contained in the compounds of formula (I) is beneficial.

According to a further aspect of the invention, there is provided a process for producing a compound of formula (I) or a pharmaceutically acceptable salt thereof.

The compound of formula (I) may be prepared by the method shown in Scheme 1, wherein, the drug or therapeutic agent contains just one carboxylic acid functional group and no other derivatizable functional groups.

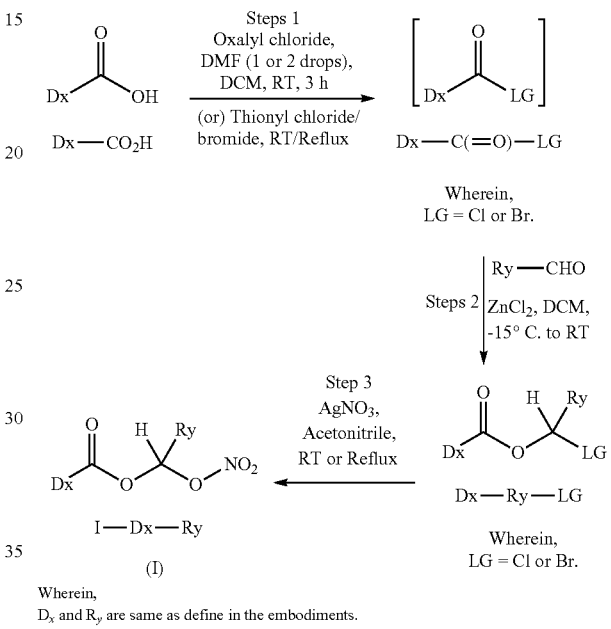

Scheme 1

Step 1

In this step, the drug or therapeutic agent containing carboxylic acid group (Dx-CO$_2$H) is treated with carbonyl chloride, for example oxalyl chloride, and DMF (catalytic amount), or thionyl chloride, in the presence of an organic solvent, for example, dichloromethane to form a reactive carbonyl derivative such as the acid chloride of formula Dx-C(=O)-LG (wherein LG=Cl).

Step 2

The reactive acid chloride Dx-C(=O)-LG is then coupled with the aldehyde Ry-CHO in the presence of a catalyst such as zinc chloride and a solvent such as dichloromethane to form a compound intermediate Dx-Ry-LG.

Step 3

The compound intermediate Dx-Ry-LG is subjected to nitration using silver nitrate in the presence of an organic solvent, for example, acetonitrile to form the compound I-Dx-Ry of formula (I), and if desired, the compound of formula (I) is converted to its pharmaceutically acceptable salt.

In Scheme 1, the variables Dx and Ry are as defined in any of the embodiments of the present invention with reference to the compounds of formula (I) wherein Dx is a part of drug/therapeutic agent containing at least one carboxylic acid group.

As mentioned above, in the synthesis of compounds of invention of formula (I), wherein, the drug or therapeutic agent contains, in addition to the required one carboxylic acid functional group, other reactive functional groups such as an amino, a hydroxyl (including phenolic and hydroxyl group of oxime derivative of a carbonyl group of an aldehyde or keto group), a sulfhydryl, a phosphate, additional carboxyl group(s) or a mixture of one or more types of these functional groups, such reactive functional groups should be masked with appropriate bio-cleavable protecting groups. The methods for the formation along with their relevant references for all the known examples of bio-cleavable amino protecting groups, hydroxyl protecting groups, sulfhydryl protecting groups, carboxyl protecting groups and phosphate protecting groups are listed in T. W. Greene, "Protective Groups in Organic Synthesis", Third Edition, 1999, John Wiley and Sons, New York, and incorporated herein as a reference.

A general method for the synthesis of compounds of invention represented by the formula (I), wherein, the drug or therapeutic agent contains, in addition to the required one carboxylic acid functional group, one or more other reactive functional groups is depicted in Scheme 2.

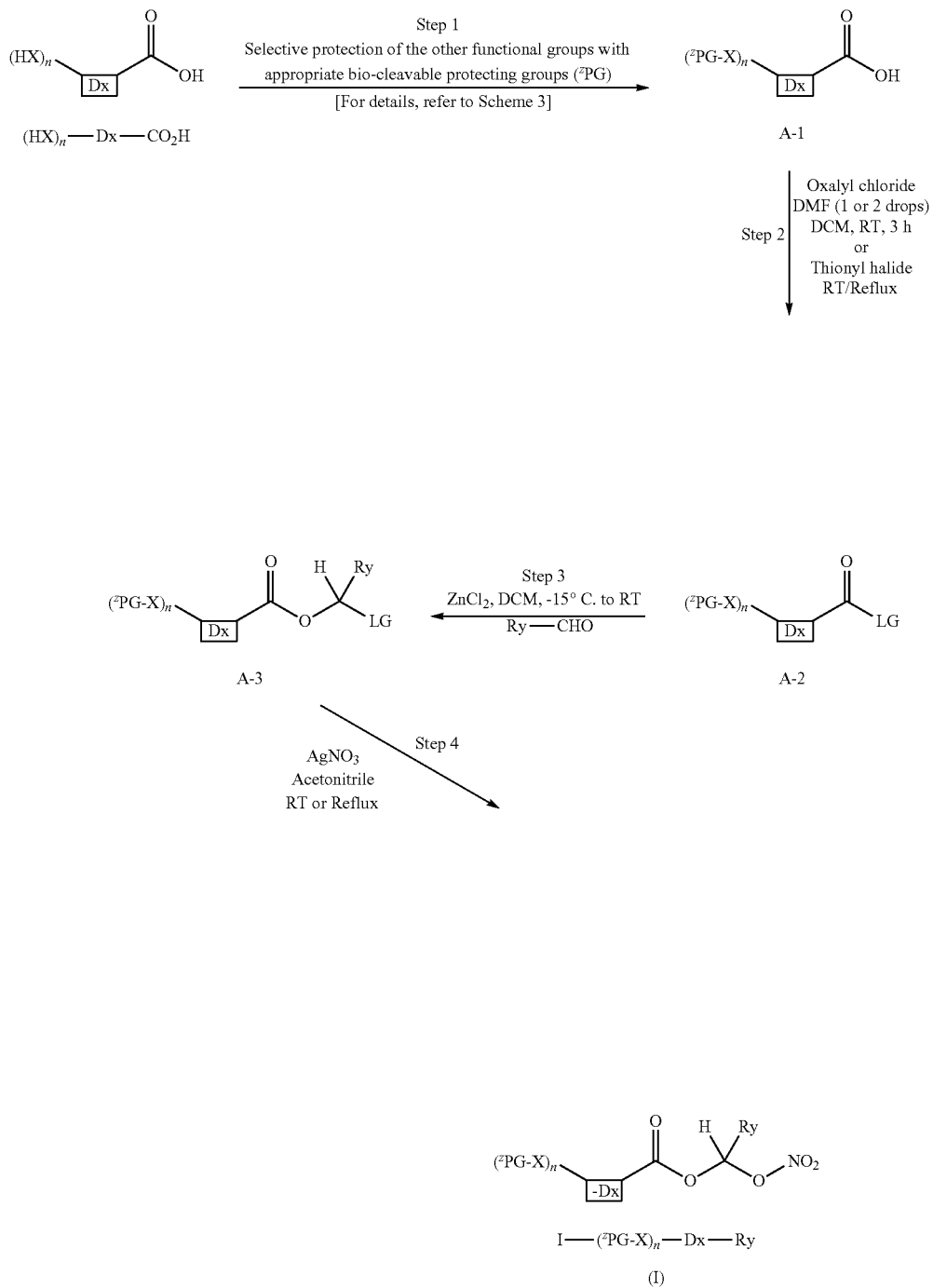

Wherein, the variables Dx and Ry are as defined in the embodiments. X=O, S, NH' (i.e., represents a primary amino group), N (i.e., represents a secondary amino group) or C(=O)O;

n represents 0 (zero) or 1-20, preferably 1-10, yet preferably 1-5, yet most preferably 1-2;

$^z$PG=a bio-cleavable protecting group of a hydroxyl ($^h$PG) or sulfhydryl ($^s$PG) or carboxyl ($^c$PG) or amino ($^a$PG) or phosphate ($^p$PG) group;

LG=Cl or Br;

Step 1

In this step, one or more reactive functional group(s) denoted by (HX)$_n$ of the drug or therapeutic agent [i.e., (HX)$_n$-Dx-CO$_2$H or simply 'Dx'] is/are selectively protected by a potential bio-cleavable protecting group such as, for example, the ethoxycarbonyl group for amino protection, the ethyl ester for carboxyl protection, the acetyl group for hydroxyl or sulfhydryl protection, the 2-(S-acetylthio)ethyl (SATE) group for phosphate protection, to obtain the corresponding protected compound of formula ($^z$PG-X)$_n$-Dx-CO$_2$H (A-1).

Step 2

The protected compound of formula (PG$^z$-X)n-Dx-CO$_2$H (A-1) (which still contains a free carboxylic acid group) is treated with carbonyl chloride, for example oxalyl chloride, and DMF (catalytic amount), or thionyl chloride, in the presence of an organic solvent, for example, dichloromethane to yield a reactive carbonyl derivative such as the acid halide of formula (PG$^z$-X)n-Dx-C(=O)-LG (A-2).

Step 3

The reactive acid halide (PG$^z$-X)n-Dx-C(=O)-LG (A-2) is then coupled with the aldehyde Ry-CHO in the presence of a catalyst such as zinc chloride and a solvent such as dichloromethane to form an intermediate compound A-3.

Step 4

The intermediate compound A-3 is subjected to nitration using silver nitrate in the presence of an organic solvent, for example, acetonitrile to form the compound of formula (I) and if desired, the compound of formula (I) is converted to its pharmaceutically acceptable salt.

The organic base used in the processes for the preparation of the compound of formula (I) as depicted in the aforementioned schemes, may be selected from but not limited to triethylamine, diisopropylethylamine, 4-(dimethylamino) pyridine (DMAP), pyridine or mixtures thereof.

The organic solvent used in the processes for the preparation of the compound of formula (I) may be selected from but not limited to dichloromethane (DCM), chloroform, dimethylformamide (DMF), tetrahydrofuran (THF), acetonitrile, ethyl acetate, diethyl ether or mixtures thereof.

Additional examples of bio-cleavable protecting groups, particularly, bio-cleavable amino protecting groups, along with their method of synthesis, are shown in Scheme 3.

Scheme 3

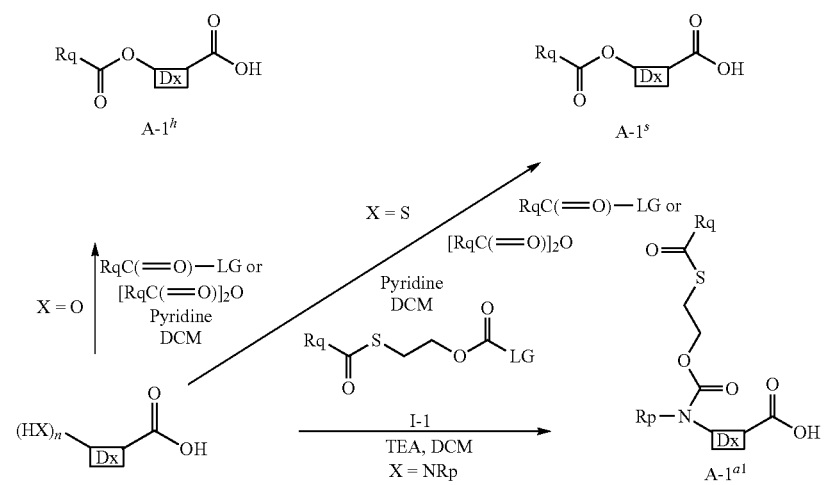

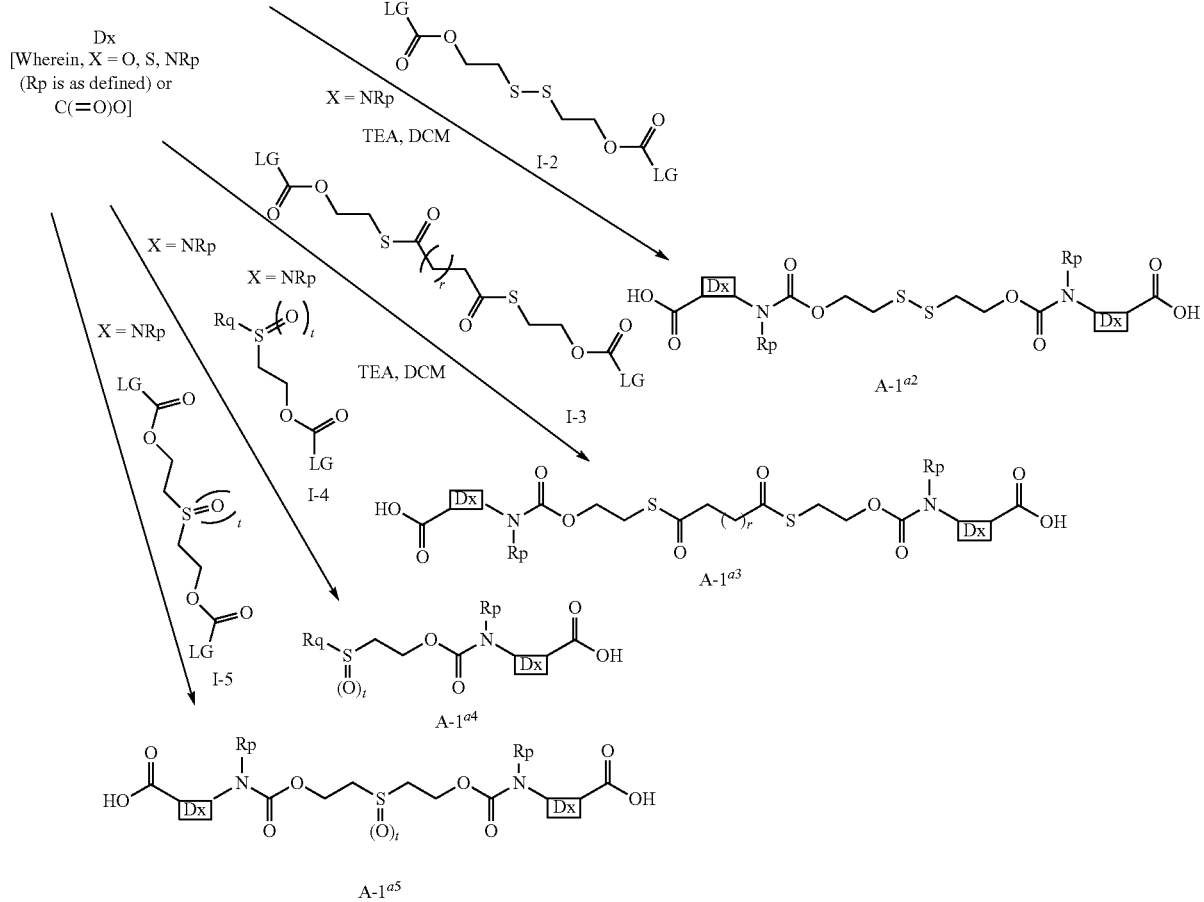

Wherein,
Rp is as defined above;
Rq=alkyl $C_{1-6}$ or $C_6H_5$;
r=1-4;
t=0-2;
LG=as defined Synthesis of intermediate A-1$^h$: The intermediate A-1$^h$ can be synthesized by treating the therapeutic agent Dx with either alkanoic acid halide (i.e., RqC(=O)-LG) or anhydride [i.e., [RqC(=O)]$_2$O] in the presence of a suitable base such as pyridine in a suitable solvent such as DCM.

One of the best examples in this category of drugs is aspirin which is O-acetylated salicylic acid.

Synthesis of intermediate A-1$^s$: The intermediate A-1$^s$ can be synthesized by treating the therapeutic agent Dx with either alkanoic acid halide (i.e., RqC(=O)-LG) or anhydride [i.e., [RqC(=O)]$_2$O] in the presence of a suitable base such as pyridine in a suitable solvent such as DCM.

Synthesis of intermediate A-1$^{a1}$: The intermediate A-1$^{a1}$ can be synthesized by treating the therapeutic agent Dx with the reactive intermediate I-1 (which can be freshly prepared in two steps by reacting 2-mercaptoethanol (HSCH$_2$CH$_2$OH) with either alkanoic acid halide (i.e., RqC(=O)-LG) or anhydride [i.e., [RqC(=O)]$_2$O] in the presence of a suitable base such as pyridine in a suitable solvent such as DCM to afford the S-acylated intermediate RqC(=O)SCH$_2$CH$_2$OH and further treating the S-acylated intermediate with phosgene or its equivalent in the presence of a suitable base such as pyridine in a suitable solvent such as DCM) in the presence of a suitable base such as triethylamine in a suitable solvent such as DCM.

Synthesis of Intermediate A-1$^{a2}$:
The intermediate A-1$^{a2}$ can be synthesized by treating the therapeutic agent Dx with the reactive intermediate I-2 (which can be synthesized by reacting bis-(2-hydroxyethyl) disulphide with phosgene or its equivalent in the presence of a suitable base such as pyridine in a suitable solvent such as DCM) in the presence of a suitable base such as triethylamine in a suitable solvent such as DCM.

Synthesis of Intermediate A-1$^{a3}$:
The intermediate A-1$^{a3}$ can be synthesized by treating the therapeutic agent Dx with the reactive intermediate I-3 (which can be synthesized by reacting dialkanoic acid halide with 2-mercaptoethanol followed by reaction with phosgene or its equivalent in the presence of a suitable base such as pyridine in a suitable solvent such as DCM) in the presence of a suitable base such as triethylamine in a suitable solvent such as DCM.

Synthesis of Intermediate A-1$^{a4}$:
The intermediate A-1$^{a4}$ can be synthesized by treating the therapeutic agent Dx with the reactive sulfone intermediate I-4 (t=2) (which can be synthesized by reacting 2-(alkylthio)ethanol or 2-(phenylthio)ethanol with phosgene or its equivalent in the presence of a suitable base such as pyridine in a suitable solvent such as DCM to get the sulfide intermediate I-4 (t=0) and further oxidation with a suitable oxidizing agent such as m-chloroperbenzoic acid in a suitable solvent such as DCM) in the presence of a suitable base such as triethylamine in a suitable solvent such as DCM.

Alternatively, the compound can be made by first treating the drug Dx with the reactive sulfide intermediate I-4 (t=0) to get the sulfide compound A-1$^{a4}$ (t=0) and its further oxidation with a suitable oxidizing agent such as m-chloroperbenzoic acid in a suitable solvent such as DCM.

Synthesis of Intermediate A-1$^{a5}$:

The intermediate A-1$^{a5}$ can be synthesized by treating the therapeutic agent Dx with the reactive intermediate I-5 (t=2) (which can be synthesized by reacting 2,2'-thiodiethanol with phosgene or its equivalent in the presence of a suitable base such as pyridine in a suitable solvent such as DCM and further oxidation with a suitable oxidizing agent such as m-chloroperbenzoic acid in a suitable solvent such as DCM) in the presence of a suitable base such as triethylamine in a suitable solvent such as DCM. Alternatively, the compound can be made by first treating the drug Dx with the reactive sulfide intermediate I-5 (t=0) to get the sulfide compound A-1$^{a5}$ (t=0) and its further oxidation with a suitable oxidizing agent such as m-chloroperbenzoic acid in a suitable solvent such as DCM.

Potential examples of compounds of formula (I) containing the above mentioned bio-cleavable amino-protecting groups (PG$^a$) and the plausible mechanisms of their cleavage in vivo are shown in Chart 2.

Chart 2

A)

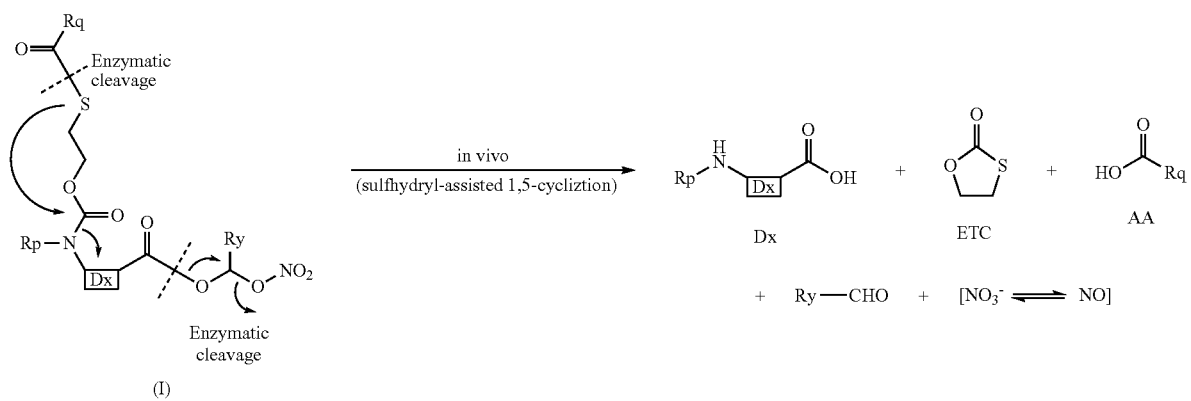

(I)
(Use of alkanoylthioethoxycarbonyl group as potential bio-cleavabe amino protecting group)

B)

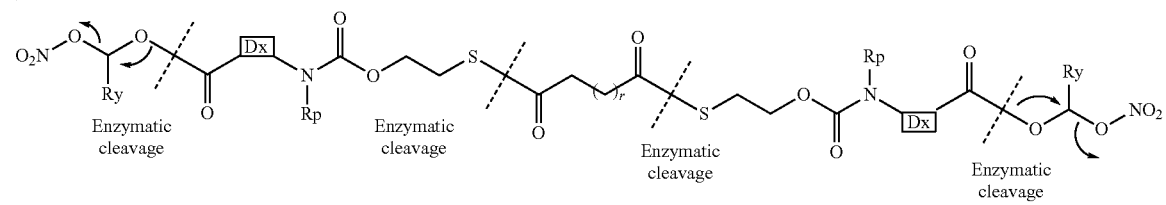

(I)
(Use of S,S-bis(2(carbonyloxy)ethyl)butanebis(thioate) group as potential bio-cleavabe amino protecting group)

in vivo
(sulfhydryl-assisted 1,5-cycliztion)

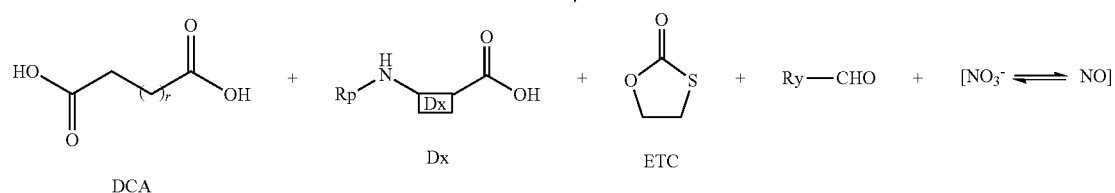

C)

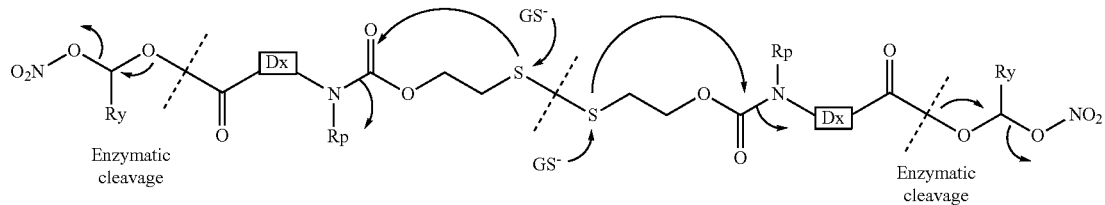

(I)
(Use of bis(2(carbonyloxyethyldisulfide group as potential bio-cleavabe amino protecting group)

in vivo
(sulfhydryl-assisted 1,5-cycliztion)

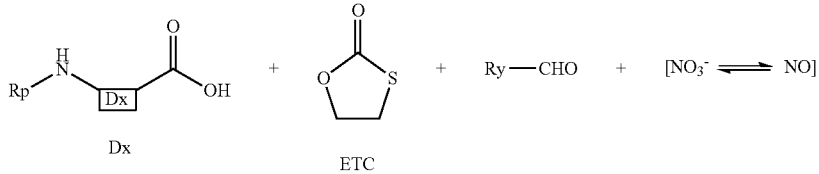

D) or E)

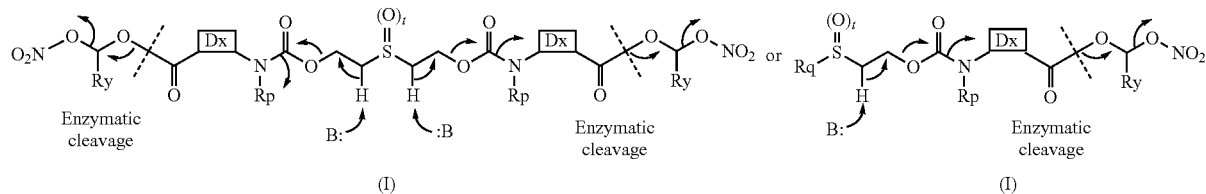

(Use of bis(2(carbonyloxyethyldisulfide or 2-carbonloxyethylalkyl/phenylsulfone groups as potential bio-cleavabe amino protecting groups)

in vivo
(Base-assisted β-elimination)

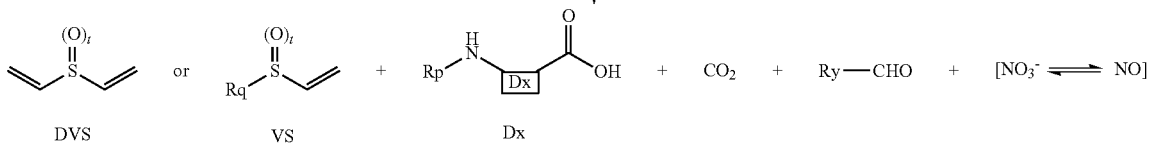

Wherein,

AA=Released alkanoic acid such as acetic acid, propionic acid, butanoic acid, pentanoic acid (valeric acid), hexanoic acid (capric acid) or heptanoic acid (enanthic acid) or benzoic acid (i.e., Rq=alkyl $C_{1-6}$ or $C_6H_5$);

ETC=Released ethylene thiocarbonate;

DCA=Released dicarboxylic acid such as succinic acid, glutamic acid, adipic acid or pimelic acid (i.e., r=1-4);

GSH=Glutathione (reduced form);

DVS=Divinyl sulfone (I.e., t=2);

VS=Vinyl sulfone (i.e., t=2, Rq=as defined above);

The present invention also relates to the process of resolution of the racemic mixture of the compound of formula (I) or a pharmaceutically acceptable salt thereof:

The process of resolution of the racemic mixture comprises reacting the racemic compound of formula (I) with a chiral auxiliary in the presence of a solvent, crystallising out the desired diastereoisomeric salt and subsequently treating it with a base to obtain the desired enantiomer of the compound of formula (I).

The present invention furthermore relates to a pharmaceutical composition containing a therapeutically effective amount of the compound of formula (I) which is a nitric oxide releasing prodrug of a known drug or a therapeutic agent or its physiologically tolerable salts, with/without a therapeutically effective amount of an anti-ulcer agent such as a proton-pump inhibitor (PPI) or a H2 receptor antagonist, and a pharmaceutically acceptable carrier, and to a process for the production of the pharmaceutical composition, which comprises converting the compound of formula (I) into a suitable administration form using an appropriate pharmaceutically acceptable and physiologically tolerable excipient, and if appropriate, using further suitable active compounds, additives or auxiliaries.

The compound of formula (I), which are the nitric oxide releasing prodrugs of known drugs or therapeutic agents, can be administered to a subject in need thereof in a variety of routes such as oral, for example in the form of pills, tablets, coated tablets, capsules, granules or elixirs. Administration, however, can also be carried out rectally, for example in the form of suppositories, or parentally, for example, intravenously, intramuscularly or subcutaneously, in the form of injectable sterile solutions or suspensions, or topically, for example in the form of solutions or transdermal patches, or in other ways, for example in the form of aerosols or nasal sprays.

The pharmaceutical composition according to the invention is prepared in a manner known per se, and by utilizing methods well-known to one skilled in the art. Pharmaceutically acceptable inert inorganic and/or organic carriers and/or additives can be used in addition to the prodrug compound of formula (I) and/or its pharmacologically acceptable salts. For the production of pills, tablets, coated tablets and hard gelatin capsules it is possible to use, for example, lactose, corn starch or derivatives thereof, gum arabic, magnesia or glucose, etc. Carriers for soft gelatin capsules and suppositories are, for example, fats, wax, natural or hardened oils, etc. Suitable carriers for the production of solutions, for example, injection solutions, or of emulsions or syrups are, for example, water, physiological sodium chloride solution or alcohols, for example, ethanol, propanol, or glycerol, sugar solutions, such as glucose solutions or mannitol solutions, or a mixture of the various solvents which have been mentioned.

The pharmaceutical composition of the invention also contain additives such as, for example, antioxidants, emulsifiers, preservatives, colouring agents and flavouring agents. The pharmaceutical composition also may also contain two or more prodrug compounds of formula (I) and/or their physiologically tolerable salts. Furthermore, in addition to at least one prodrug compound of formula (I) and/or its physiologically tolerable salts, the pharmaceutical composition can also contain one or more other therapeutically or prophylactically active ingredients.

It would be understood by persons skilled in the art that the amount of the compound of formula (I) (prodrugs of known drugs or therapeutic agents) that is contained in the pharmaceutical composition will depend upon the equimolar amount of the parent drug molecule included therein. Generally, the amount of the prodrug used in the treatment methods is that amount which effectively achieves the desired therapeutic effect in subjects being treated for a particular disease. Naturally, the dosages of the various prodrugs encompassed in the compounds of formula (I) will vary somewhat depending upon the parent drug molecule, rate of in vivo drug hydrolysis, etc.

The pharmaceutical composition contains about 1 to 99, preferably about 1 to 80% and most preferably from about 10 to 70% by weight of the prodrug compound of formula (I) and/or the physiologically tolerable salts of prodrug compound of formula (I). The effective amount of the active ingredient of prodrug compound of formula (I) and/or its physiologically tolerable salts in the pharmaceutical composition in order to obtain a desired therapeutic effect varies from 1 to 5000 mg. The desirable dosage of the pharmaceutical composition to be administered can vary over a wide range. The selected dosage level can be readily determined by a skilled medical practitioner in the light of the relevant circumstances, including the condition (diseases or disorder) to be treated, the chosen route of administration depending on a number of factors, such as age, weight and physical health and response of the individual patient, pharmacokinetics, severity of the disease and the like, factors known in the medical art. However, in order to obtain desirable effects, it would be recommended to administer the pharmaceutical composition in the form of oral tablets (tablets, capsules) daily/weekly/monthly and in a dosage ranging from 1 mg to 5000 mg, preferably 1 mg to 2000 mg, in a single dosage form or a multi-dosage form.

The range set forth above is illustrative and those skilled in the art will be able to determine the optimal dosing of the compounds of formula (I) of the present invention selected, based on clinical experience and the medical indication or disease to be treated in a subject in need of the treatment.

Another aspect of the present invention is to provide methods for the treatment of various medical conditions or diseases or disorders in a subject comprising administering to a subject in need thereof a therapeutically effective amount of a compound of formula (I). It has already been indicated herein above that the compounds of formula (I) of the present invention are prodrugs of known drugs or therapeutic agents containing at least one carboxylic acid group. The specific class of therapeutic agents encompassed within the scope of the invention are described herein above. According to the present invention, the diseases or disorders or the medical conditions for the treatment of which the compounds of formula (I) of the present invention are used are those for which the parent drug molecule (represented by the variable Dx which encompasses specific therapeutic agents) is conventionally used by a medical practitioner.

Moreover, the compounds of formula (I), which are the prodrugs of known drugs or therapeutic agents, in all likelihood are advantageous over the parent drug molecules or prodrugs of the parent molecule known hitherto in the prior art in terms of comparable or potentially superior oral bioavailability, reduced adverse effect, for instance, gastric irritability caused by NSAIDS, etc.

It is understood that modifications that do not substantially affect the activity of the various embodiments of this invention are included within the scope of the invention disclosed herein. Accordingly, the following examples are intended to illustrate but not to limit the scope of the present invention.

EXPERIMENTAL

The abbreviations and terms that are used herein:
(COCl)$_2$: Oxalyl chloride
DMF: N,N-Dimethylformamide
DCM: Dichloromethane
CBr$_4$: Carbon tetrabromide
TPP: Triphenylphosphine
EtOAc or EA: Ethyl acetate
PE: Petroleum ether
RT: Room Temperature
ACN: Acetonitrile
ZnCl$_2$: Zinc Chloride
AgNO$_3$: Silver Nitrate
TFA: Trifluoroacetic acid
HPLC: High Performance Liquid Chromatography
TLC: Thin Layer Chromatography Example 1

1-(nitrooxy)ethyl 2-acetoxybenzoate I-D1-R1

The title compound was synthesized in 3 steps as shown in Scheme 1 and the experimental procedure is described below.

Steps 1 and 2: Synthesis of 1-chloroethyl 2-acetoxybenzoate D1-R1-Cl

To a stirred suspension of aspirin (40.00 g, 222.22 mmol) in dry DCM (250 mL) were added oxalyl chloride (22.80 mL, 266.56 mmol) and a catalytic amount of DMF (4-5 drops) at RT under nitrogen. The resulting mixture was stirred at RT for 3 hours and concentrated to afford aspirin acid chloride (quantitative) as pale yellow oil. To a stirred solution of the acid chloride (11.00 g, 55.55 mmol) in dry DCM (100 mL) was added a catalytic amount of zinc chloride (0.15 g, 1.11 mmol) followed by drop wise addition of acetaldehyde (3.10 mL, 55.55 mmol) at −15° C. under nitrogen. The reaction mixture was stirred at RT for 16 hours and concentrated. The residue was dissolved in ethyl acetate (100 mL), washed successively with water (3×100 mL), saturated sodium bicarbonate solution (3×100 mL) and brine (2×100 mL), dried over sodium sulfate and concentrated. The crude compound was purified by silica gel (200-400 mesh) column chromatography using a gradient of 5 to 15% ethyl acetate in petroleum ether as eluent to afford the desired compound D1-R1-Cl (3.00 g, 23.0%) as colorless oil. $^1$H NMR (CDCl$_3$, 300 MHz): δ 1.91 (d, J=5.7 Hz, 3H), 2.39 (s, 3H), 6.75 (q, J=5.7, 11.7 Hz, 1H), 7.36 (t, J=7.8 Hz, 1H), 7.60-7.64 (m, 1H), 8.00 (dd, J=1.2, 7.8 Hz, 1H)

Step 3: Synthesis of 1-(nitrooxy)ethyl 2-acetoxybenzoate I-D1-R1

To a stirred solution of 1-chloroethyl 2-acetoxybenzoate D1-R1-Cl (3.00 g, 12.29 mmol) in dry acetonitrile (30 mL) was added silver nitrate (3.10 g, 18.44 mmol) at RT. The reaction mixture was refluxed at 80-90° C. for 1 hour, filtered over celite and concentrated. The residue was re-dissolved in DCM (70 mL); the precipitated silver salt was filtered over celite and the filtrate was concentrated (this process was repeated twice). The crude compound was purified by silica gel (200-400 mesh) column chromatography using a gradient of 5 to 15% ethyl acetate in petroleum ether as eluent to afford I-D1-R1 (2.70 g, 81.0%) as pale yellow oil. $^1$H NMR (CDCl$_3$, 300 MHz): δ 1.66 (d, J=5.7 Hz, 3H), 2.37 (s, 3H), 7.14 (d, J=8.1 Hz, 1H), 7.27 (q, J=5.4, 11.4 Hz, 1H), 7.33-7.36 (m, 1H), 7.60-7.64 (m, 1H), 8.0 (dd, J=1.5, 8.1 Hz, 1H); MS (ES$^-$) m/z: 268.1 [M−H]$^-$ The compounds of Examples 2-8 were synthesized as shown in Scheme 1 by following the experimental procedure for the compound exemplified in Example 1. The characterization data for the compounds of Examples 2-8 is described below:

Example 2

1-(nitrooxy)propyl 2-acetoxybenzoate I-D1-R2

Steps 1 and 2: Synthesis of 1-chloropropyl 2-acetoxybenzoate D1-R2-Cl

The title compound was synthesized using aspirin (5.00 g, 27.78 mmol) and oxalyl chloride (3.00 mL, 33.34 mmol) to give aspirin acid chloride which was reacted with propionaldehyde (1.46 g, 25.23 mmol) in the presence of catalytic amounts of ZnCl$_2$ (0.068 g, 0.50 mmol) to give the corresponding chloro intermediate D1-R2-Cl (1.96 g, 30.0%) as yellow oil. $^1$H NMR (CDCl$_3$, 300 MHz): δ 1.13 (t, J=7.5 Hz, 3H), 2.09-2.20 (m, 2H), 2.39 (s, 3H), 6.60 (t, J=3.0 Hz, 3H), 7.15 (d, J=8.1 Hz, 1H), 7.35 (t, J=7.2 Hz, 1H), 7.60-7.63 (m, 1H), 8.06 (dd, J=1.5, 7.8 Hz, 1H); $^{13}$C NMR (CDCl$_3$, 75.47 MHz): δ 9.2, 21.0, 31.6, 76.6, 77.0, 77.4, 85.6, 122.2, 124.1, 126.1, 131.9, 134.7, 151.1, 162.1, 169.6; MS (ES$^+$) m/z 256.3 [M+H]$^+$ Step 3: Synthesis of 1-(nitrooxy)propyl 2-acetoxybenzoate I-D1-R2

Nitration of the chloro intermediate D1-R2-Cl (1.93 g, 7.52 mmol) with AgNO$_3$ (1.53 g, 9.02 mmol) afforded the desired nitro compound I-D1-R2 (1.38 g, 65.0%) as light green oil. $^1$H NMR (CDCl$_3$, 300 MHz): δ 1.09 (t, J=9.0 Hz, 3H), 1.94-2.04 (m, 2H), 2.36 (s, 3H), 7.13-7.16 (m, 2H), 7.35 (t, J=7.2 Hz, 1H), 7.60-7.63 (m, 1H), 8.04 (dd, J=1.5, 7.8 Hz, 1H); $^{13}$C NMR (CDCl$_3$, 75.47 MHz): δ 7.7, 20.9, 24.9, 96.9, 121.7, 124.1, 126.2, 132.0, 134.8, 151.0, 162.2, 169.5; MS (ES$^+$) m/z 358.2 [M+H]$^+$ Example 3

1-(nitrooxy)butyl 2-acetoxybenzoate I-D1-R3

Steps 1 and 2: Synthesis of 1-chlorobutyl 2-acetoxybenzoate D1-R3-Cl

The title compound was synthesized using aspirin (5.00 g, 27.78 mmol) and oxalyl chloride (3.00 mL, 33.34 mmol) to give aspirin acid chloride. The aspirin acid chloride was reacted with butyraldehyde (1.81 g, 25.18 mmol) in the presence of catalytic amounts of ZnCl$_2$ (0.068 g, 0.50 mmol) to give the corresponding chloro intermediate D1-R3-Cl (2.93 g, 43.0%) as yellow oil. $^1$H NMR (CDCl$_3$, 300 MHz): δ 1.00 (t, J=7.5 Hz, 3H), 1.54-1.62 (m, 2H), 2.00-2.15 (m, 2H), 2.39 (s, 3H), 6.65 (t, J=6.0 Hz, 1H), 7.15 (d, J=7.8 Hz, 1H), 7.36 (t, J=7.5 Hz, 1H), 7.63 (td, J=7.5, 7.8 Hz, 1H), 8.05 (dd, J=1.5, 7.8 Hz, 1H); $^{13}$C NMR (CDCl$_3$, 75.47 MHz): δ 13.4, 18.2, 21.1, 40.2, 124.1, 126.1, 131.9, 151.1, 162.1, 169.5; MS (ES$^+$) m/z 293.0 [M+Na]$^+$ Step 3: Synthesis of 1-(nitrooxy)butyl 2-acetoxybenzoate I-D1LR3

Nitration of the chloro intermediate D1-R3-Cl (2.90 g, 10.71 mmol) with AgNO$_3$ (2.18 g, 12.85 mmol) afforded the desired nitro compound I-D1-R3 (1.50 g, 47.0%) as light green oil. $^1$H NMR (CDCl$_3$, 300 MHz): δ 1.04 (t, J=6.0 Hz, 3H), 1.50-1.60 (m, 2H), 1.89-1.97 (m, 2H), 2.36 (s, 3H), 7.20 (t, J=5.7 Hz, 1H), 7.35 (t, J=7.8 Hz, 1H), 7.60-7.63 (m, 1H), 8.05 (dd, J=1.5, 8.1 Hz, 1H); $^{13}$C NMR (CDCl$_3$, 75.47 MHz): δ 13.6, 16.8, 20.9, 33.3, 96.0, 121.8, 124.1, 126.2, 132.0, 134.8, 151.0, 162.2, 169.5; MS (ES$^+$) m/z 320.0 [M+Na]$^+$, 336.0 [M+K]$^+$ Example 4

(2S)-1-(nitrooxy)ethyl 2-(6-methoxynaphthalen-2-yl)propanoate I-D2-R1

Steps 1 and 2: Synthesis of (2S)-1-chloroethyl 2-(6-methoxynaphthalen-2-yl)propanoate D2-R1-Cl The title compound was synthesized using naproxen (5.00 g, 21.71 mmol) and oxalyl chloride (5.51 mL, 65.14 mmol) to give naproxen acid chloride which was reacted with acetaldehyde (1.22 mL, 21.71 mmol) in the presence of catalytic amounts of ZnCl$_2$ (0.060 g, 0.43 mmol) to give the corresponding chloro intermediate D2-R1-Cl (5.10 g, 80.0%) as yellow oil. $^1$H NMR (CDCl$_3$, 300 MHz): δ 1.60 (d, J=3.0 Hz, 1.5H), 1.62 (d, J=3.6 Hz, 1.5 Hz), 1.70 (d, J=5.7 Hz, 1.5H), 1.77 (d, J=5.7 Hz, 1.5H), 3.89 (q, J=7.2 Hz, 1H), 3.93 (s, 3H), 6.50-6.61 (m, 1H), 7.14-7.18 (m, 2H), 7.37-7.42 (m, 1H), 7.68-7.74 (m, 3H); MS (ES$^+$) m/z 293.1 [M+H]$^+$

Step 3: Synthesis of (2S)-1-(nitrooxy)ethyl 2-(6-methoxynaphthalen-2-yl)propanoate I-D2-R1

Nitration of the chloro intermediate D2-R1-Cl (4.00 g, 13.66 mmol) with AgNO$_3$ (4.64 g, 27.32 mmol) afforded the desired nitro compound I-D2-R1 (3.22 g, 74.0%) as yellow solid. mp 69-71° C.; $^1$H NMR (CDCl$_3$, 300 MHz): δ 1.43 (d, J=1.5 Hz, 1.5H), 1.54 (d, J=1.5 Hz, 1.5H), 1.58-1.59 (m, 3H), 3.88 (q, J=7.2 Hz, 1H), 3.94 (s, 3H), 7.02-7.09 (m, 1H), 7.14-7.19 (m, 2H), 7.36 (t, J=8.9 Hz, 1H), 7.65 (d, J=7.8 Hz, 1H), 7.70-7.73 (m, 2H); $^{13}$C NMR (CDCl$_3$, 100 MHz): δ 17.6, 18.7, 45.7, 55.7, 81.3, 94.2, 119.5, 126.3, 126.4, 127.7, 129.3, 129.6, 134.2, 134.9, 158.2, 172.8; MS (ES$^-$) m/z 318.1 (M−H)$^-$, MS (ES$^+$) m/z 320.1 (M+H)$^+$

Example 5

(2S)-1-(nitrooxy)propyl 2-(6-methoxynaphthalen-2-yl)propanoate I-D2-R2

Steps 1 and 2: Synthesis of (2S)-1-chloropropyl 2-(6-methoxynaphthalen-2-yl)propanoate D2-R2-Cl The title compound was synthesized using naproxen (5.00 g, 21.73 mmol) and oxalyl chloride (2.20 mL, 26.08 mmol) to give naproxen acid chloride which was reacted with propionaldehyde (0.74 mL, 10.08 mmol) in the presence of catalytic amounts of ZnCl$_2$ (0.082 g, 0.60 mmol) to give the corresponding chloro intermediate D2-R2-Cl (0.90 g, 30.0%) as dark yellow oil. $^1$H NMR (CDCl$_3$, 300 MHz): δ 0.88-1.00 (m, 3H), 1.61 (d, J=6.0 Hz, 3H), 1.99-2.09 (m, 2H), 3.89-3.98 (m, 1H), 3.99 (s, 3H), 6.35-6.43 (m, 1H), 7.14 (dd, J=2.1, 2.4 Hz, 2H), 7.41 (dd, J=1.5 Hz each, 1H), 7.71 (t, J=8.3 Hz, 3H); MS (ES$^+$) m/z: 307 (M+H)$^+$

Step 3: Synthesis of (2S)-1-(nitrooxy)propyl 2-(6-methoxynaphthalen-2-yl)propanoate I-D2-R2

Nitration of the chloro intermediate D2-R2-Cl (0.90 g, 2.94 mmol) with AgNO$_3$ (0:59 g, 3.52 mmol) afforded the desired nitro compound I-D2-R2 (0.30 g, 30.7%) as yellow oil. $^1$H NMR (CDCl$_3$, 300 MHz): δ 0.83 (t, J=7.5 Hz, 3H), 1.61-1.62 (m, 3H), 1.80-1.90 (m, 2H), 3.86-3.91 (m, 1H), 3.93 (s, 3H), 6.90-6.94 (m, 1H), 7.13-7.18 (m, 2H), 7.34-7.36 (m, 1H), 7.65 (d, J=7.2 Hz, 1H), 7.72 (d, J=8.7 Hz, 2H); $^{13}$C NMR (CDCl$_3$, 75.47 MHz): δ 7.8, 8.0, 18.5, 25.0, 45.7, 55.7, 97.1, 106.1, 119.5, 126.2, 126.4, 127.7, 129.26, 129.6, 134.2, 134.7, 158.1; MS (ES$^+$) m/z: 356.1 (M+Na)$^+$

Example 6

(2S)-1-(nitrooxy)butyl 2-(6-methoxynaphthalen-2-yl)propanoate I-D2-R3

Steps 1 and 2: Synthesis of (2S)-1-chlorobutyl 2-(6-methoxynaphthalen-2-yl)propanoate D2-R3-Cl The title compound was synthesized using naproxen (5.00 g, 21.71 mmol) and oxalyl chloride (5.51 mL, 65.14 mmol) to give naproxen acid chloride which was reacted with butyraldehyde (1.94 mL, 21.71 mmol) in the presence of catalytic amounts of ZnCl$_2$ (0.06 g, 0.43 mmol) to give the corresponding chloro intermediate D2-R3-Cl as yellow oil (4.50 g, 65.0%); $^1$H NMR (CDCl$_3$, 300 MHz): δ 0.82 (t, J=7.3 Hz, 1.5H), 0.94 (t, J=7.3 Hz, 1.5H), 1.26-1.33 (m, 1H), 1.42-1.50 (m, 1H), 1.59-1.63 (m, 3H), 1.88-1.98 (m, 2H), 3.89 (q, J=7.1 Hz, 1H), 3.93 (s, 3H), 6.40-6.49 (m, 1H), 7.14-7.18 (m, 2H), 7.38-7.41 (m, 1H), 7.68-7.74 (m, 3H).

Step 3: Synthesis of (2S)-1-(nitrooxy)butyl 2-(6-methoxynaphthalen-2-yl)propanoate I-D2-R3

Nitration of the chloro intermediate D2-R3-Cl (2.00 g, 6.23 mmol) with AgNO$_3$ (2.11 g, 12.46 mmol) afforded the desired nitro compound I-D2-R3 as light yellow oil. Yield: 57.0%; $^1$H NMR (CDCl$_3$, 300 MHz): δ 0.84 (t, J=7.3 Hz, 1.5H), 0.96 (t, J=7.3 Hz, 1.5H), 1.24-1.47 (m, 2H), 1.59 (d, J=3.0 Hz, 3H), 1.65-1.83 (m, 2H), 3.89 (q, J=7.2 Hz, 1H), 3.94 (s, 3H), 6.96-7.00 (m, 1H), 7.14-7.19 (m, 2H), 7.36 (t, J=8.6 Hz, 1H), 7.65 (d, J=7.8 Hz, 1H), 7.70-7.73 (m, 2H); $^{13}$C NMR (CDCl$_3$, 100 MHz): δ 13.8, 13.9, 16.9, 17.2, 18.5, 18.6, 33.4, 33.5, 45.6, 45.7, 55.7, 134.2, 134.7, 134.9, 158.1, 173.0; MS (ES$^+$) m/z 360.3 (M+Na)$^+$

Example 7

(2S)-1-(nitrooxy)pentyl 2-(6-methoxynaphthalen-2-yl)propanoate I-D2-R4

Steps 1 and 2: Synthesis of (2S)-1-chloropentyl 2-(6-methoxynaphthalen-2-yl)propanoate D2-R4-Cl The title compound was synthesized using naproxen (5.00 g, 21.73 mmol) and oxalyl chloride (2.20 mL, 26.08 mmol) to give naproxen acid chloride which was reacted with pentanal (0.87 g, 10.05 mmol) in the presence of catalytic amounts of ZnCl$_2$ (0.082 g, 0.50 mmol) to give the corresponding chloro intermediate D2-R4-Cl (0.80 g, 23.0%) as dark yellow oil. $^1$H NMR (CDCl$_3$, 300 MHz): δ 0.72-0.94 (m, 3H), 1.18-1.19 (m, 2H), 1.25-1.41 (m, 2H), 1.61 (d, J=7.2 Hz, 3H), 1.89-2.05 (m, 2H), 3.87-3.97 (m, 4H), 6.38-6.47 (m, 1H), 7.14-7.18 (m, 2H), 7.38-7.41 (m, 1H), 7.67-7.74 (m, 3H); MS (ES$^+$) m/z: 335.2 (M+H)$^+$

Step 3: Synthesis of (2S)-1-(nitrooxy)pentyl 2-(6-methoxynaphthalen-2-yl)propanoate I-D2-R4

Nitration of the chloro intermediate D2-R4-Cl (0.80 g, 2.39 mmol) with AgNO$_3$ (0.81 g, 4.70 mmol) afforded the desired nitro compound I-D2-R4 (0.30 g, 34.8%) as yellow oil. $^1$H NMR (CDCl$_3$, 300 MHz): δ 0.72-0.77 (m, 1H), 0.87-0.98 (m, 2H), 1.19-1.21 (m, 1H), 1.34-1.43 (m, 2H), 1.60-1.61 (m, 3H), 1.66-1.82 (m, 2H), 3.85-3.93 (m, 4H), 6.94-6.99 (m, 1H), 7.13-7.19 (m, 2H), 7.34-7.40 (m, 1H), 7.64-7.73 (m, 3H); $^{13}$C NMR (CDCl$_3$, 75.47 MHz): δ 13.7, 18.2, 22.0, 25.1, 30.8, 45.4, 55.3, 96.1, 105.6, 119.1, 125.9, 126.1, 127.3, 129.3, 133.8, 134.6, 133.8, 157.8, 172.6; MS (ES$^+$) m/z: 384.1 [M+Na]$^+$

Example 8

1-(nitrooxy)ethyl 4-(4-(bis(2-chloroethyl)amino)phenyl)butanoate I-D3-R1

Steps 1 and 2: Synthesis of 1-chloroethyl 4-(4-(bis (2-chloroethyl)amino)phenyl)butanoate D3-R1-Cl The title compound was synthesized using chlorambucil (1.00 g, 3.29 mmol) and oxalyl chloride (0.35 mL, 3.95 mmol) to give chlorambucil acid chloride which was reacted with acetaldehyde (1.50 mL, 26.32 mmol) in the presence of catalytic amounts of ZnCl$_2$ (0.04 g, 0.33 mmol) to give the corresponding chloro intermediate D3-R1-Cl (0.31 g, 31.0%) as dark brown oil. $^1$H NMR (CDCl$_3$, 300 MHz): δ 1.79 (d, J=5.7 Hz, 3H), 1.92-1.99 (m, 2H), 2.38 (t, J=7.5 Hz, 2H), 2.59 (t, J=7.2 Hz, 2H), 3.62-3.74 (m, 8H), 6.56 (q, J=5.7, 1H), 6.64 (d, J=8.4 Hz, 2H), 7.10 (d, J=8.4 Hz, 2H)

Step 3: Synthesis of (1-(nitrooxy)ethyl 4-(4-(bis(2-chloroethyl)amino)phenyl)butanoate I-D3-R1

Nitration of the chloro intermediate D3-R1-Cl (0.10 g, 0.26 mmol) with AgNO$_3$ (0.050 g, 0.31 mmol) afforded the desired nitro compound I-D3-R1 (0.07 g, 70.0%) as brown oil. $^1$H NMR (CDCl$_3$, 300 MHz): δ 1.55 (d, J=5.7 Hz, 3H), 1.90-1.97 (m, 2H), 2.37 (t, J=7.2 Hz, 2H), 2.57 (t, J=7.2 Hz, 2H), 3.62-3.74 (m, 8H), 6.65 (d, J=8.7 Hz, 2H), 7.03-7.09 (m, 3H); MS (ES$^+$) m/z: 393 [M+H]$^+$ Experimental Data—Biological:
Biological Evaluation The NO-aspirin prodrugs I-D1-R1, I-D1-R2, I-D1-R3 and NO-naproxen prodrugs I-D2-R1, I-D2-R2, I-D2-R3, I-D2-R4 were evaluated in vivo to establish their bioavailability and/or anti-inflammatory efficacy. A few prodrugs with promising bioavailability were selected and evaluated further for their nitric oxide release capabilities and their gastric ulcer sparing/inducing effects in comparison to their respective parent drugs.

The most promising NO-aspirin prodrug I-D1-R1 was further evaluated for its ability to inhibit thromboxane B2 (TXB2) and its efficacy was compared with that of aspirin at equimolar dose. The prodrugs I-D1-R1 (NO-aspirin) and I-D2-R1 (NO-naproxen) were also tested for their stability at different temperatures (RT and 50° C.) and in aqueous media (vehicles) such as aqueous solution of carboxymethyl cellulose (CMC) and polyethylene glycol (PEG) over a pH range of 1 to 9.

The promising NO-aspirin prodrug I-D1-R1 was further tested for its stability in Simulated Gastric Fluid (SGF), Simulated Intestinal Fluid (SIF) and 100% human plasma and its unique capability to release aspirin in these media thereby acting as a true prodrug of aspirin was determined. It is well known to the people skilled in the art that it has been a very difficult task to design a true ester prodrug of aspirin due to the presence of a very labile acetyl group which undergoes preferential hydrolysis by plasma esterases. Consequently, a vast majority of ester prodrugs of aspirin turn out be prodrugs of salicylic acid.

Pharmacokinetics (PK) of the Compounds of Invention in Rats:

The bioavailability (AUC) data presented for NO-naproxen prodrugs correspond to the plasma concentration of the released parent drug, naproxen. However, as mentioned above, the bioavailability data for aspirin or the NO-aspirin prodrugs correspond to the plasma concentration of the released salicylic acid rather than that of aspirin due to the fact that both aspirin and NO-aspirin prodrugs preferentially undergo de-acetylation in vivo by plasma esterases to give salicylic acid.

Among the NO-aspirin series, as shown in FIG. 1 and Table 7, prodrug I-D1-R1 showed nearly comparable bioavailability to that of aspirin (AUCs: 91.13±12.20 μg*hr/mL versus 89.78±10.20 μg*hr/mL) and the remaining two prodrugs not only showed less bioavailability to that of aspirin but also exhibited a decreasing trend in bioavailability with increasing length of the alkyl chain.

In order to assess the species-specific differences in oral bioavailability of the prodrugs of this invention, we have carried out PK studies on the promising prodrug I-D1-R1 (NO-aspirin) and aspirin in Wistar rats and the results are presented in FIG. 2 and Table 7.

Interestingly, both aspirin and its prodrug I-D1-R1 have shown comparable bioavailability (AUCs: 436.8±26.2 μg*hr/mL versus 397.6±28.0 μg*hr/mL) in Wistar rats also. However, both aspirin and its prodrugs have shown strikingly improved oral absorption in Wistar rats as compared to that in Sprague-Dawley (SD) rats (AUCs for Aspirin: 436.8±26.2 versus 91.13±12.20 at 30 mg/kg equimolar dose; AUCs for prodrug I-D1-R1: 397.6±28.0 μg*hr/mL versus 89.78±10.20 μg*hr/mL at 44.83 mg/kg, which is equimolar to 30 mg/kg dose of aspirin).

Among the NO-naproxen series also, as shown in FIG. 3 and Table 7, the prodrug I-D2-R1 exhibited superior and statistically significant increase in bioavailability (AUC: 272.60±8.50 μg*hr/mL, **p<0.01) over that of naproxen (AUC: 207.80±18.20 μg*hr/mL) in SD rats. It is interesting to note their important PK parameters. i.e., while Tmax for naproxen was shown to be <15 min with a Cmax of about 55 μg/mL, the prodrug I-D2-R1 showed a Tmax around 1 h with Cmax of about 50 μg/mL. It is also interesting to note that the plasma drug concentration in prodrug treated animals was found to be between 30 and 35 μg/mL during the period from 0.5 h to 6.0 h (between 40 and 55 μg/mL during the period between 1 h and 4 h). However, the plasma drug concentration in naproxen treated animals, although showed a Cmax of above 55 μg/mL at 15 min, quickly reached to just above 30 μg/ml in 2 h and to just above 20 μg/mL in a period of 4 hours and it further dropped to below 15 μg/ml in a period of 8 h. So, the prodrug I-D1-R1 has exhibited controlled release of higher amounts of naproxen over a longer period of time (over 30 μg/mL up to 6 h) when compared to naproxen at equimolar doses. This prodrug is therefore expected to offer pain relief for a longer period of time than the parent drug naproxen although the parent drug is expected to offer quicker relief from pain than its prodrug due to its faster absorption within 15 min of administration of the drug.

The remaining prodrugs in the naproxen series (i.e., I-D2-R2, I-D2-R3 and I-D2-R4) exhibited either comparable (I-D2-R2 with an AUC value of 182.70±8.10 μg*hr/mL) or slightly less (i.e., I-D2-R3 and I-D2-R4 with AUC values of 178.60±8.10 μg*hr/mL and 177.40±4.10 μg*hr/mL, respectively) bioavailability when compared to that of naproxen with an AUC value of 207.80±18.20 μg*hr/mL and also showed some decreasing trend, although not significant, in bioavailability with increasing chain length of "Ry" group.

TABLE 7

Pharmacokinetic study data of compounds of invention:

| Compound[1] | Plasma Aspirin/Naproxen AUC[2, 3, 4] (μg*hr/mL) |
|---|---|
| Aspirin | 91.13 ± 12.20 (436.80 ± 26.20)[5] |
| I-D1-R1 | 89.78 ± 4.90 (397.60 ± 28.00)[5] |
| I-D1-R2 | 73.54 ± 4.90 |
| I-D1-R3 | 53.56 ± 15.60 |
| Naproxen | 207.80 ± 18.20 |
| I-D2-R1 | 272.60 ± 8.50** |
| I-D2-R2 | 182.70 ± 8.10 |

TABLE 7-continued

Pharmacokinetic study data of compounds of invention:

| Compound[1] | Plasma Aspirin/Naproxen AUC[2, 3, 4] (μg*hr/mL) |
|---|---|
| I-D2-R3 | 178.6 ± 8.1 |
| I-D2-R4 | 177.40 ± 4.1 |

[1]All the compounds were administered per oral either at 30 mg/kg equivalent dose of aspirin or 10 mg/kg equivalent dose of naproxen.
[2]Average of pooled samples (n = 3).
[3]Used SD Rats.
[4]AUC of aspirin corresponds to the released plasma salicylate.
[5]Used Wistar Rats.
**p < 0.01 versus Naproxen.

Anti-Inflammatory Efficacy of Representative Compounds of the Invention:

It is reported that the anti-inflammatory activity of an NSAID is directly proportional to the plasma concentration of the drug (Nemmani, K. V. S., et al., Bioorganic and Medicinal Chemistry Letters, 2009, 19, 5297-5301 and Pathan, A. R., et al., Inflammopharmacology, 2010, 18, 157-168). The anti-inflammatory activity of compounds of formula (I) was estimated based on their respective oral bioavailability data. Moreover, the anti-inflammatory activity of the compounds of this invention represented by the formula (I) can be readily assessed in carrageenan-induced rat paw edema model according to the reported procedure (Al-Swayeh, O. A., el al., Br. J. Pharmacol. 2000, 129, 343-350).

Based on its better bioavailability, we expect the prodrug I-D2-R1 (NO-naproxen) to show superior or at least comparable anti-inflammatory activity to that of naproxen in the carrageenan-induced rat paw edema model.

Similarly, based on its nearly comparable bioavailability to aspirin, it is expected that the prodrug I-D1-R1 (NO-aspirin) would show comparable anti-inflammatory activity to that of the parent drug aspirin.

Estimation of Nitric Oxide Release from the Compounds of the Invention:

Nitric oxide is reported to act as a mediator of gastrointestinal (GI) mucosal defense by indirectly suppressing various deleterious events resulting from NSAID-induced inhibition of COX-1 such as suppression of prostanoid synthesis, reduction in mucosal blood flow and over-expression of inflammatory mediators such as plasma tumor necrosis factor alfa (TNF-α), etc. (Lanas, A. Arthritis Res. Ther. 2008, 10 (Suppl. 2), S4). People with diabetes are believed to be associated with deficiency of nitric oxide (according to a research report from Florida University, which can be accessed at www.news.health.ufl.edu) and may benefit from the nitric-oxide releasing compounds of this invention. For example, depleted levels of nitric oxide have been implicated in diseases such as heart failure, pulmonary hypertension and sexual dysfunction. We therefore evaluated the nitric oxide releasing capability of the compounds of present invention in rats by taking the two prodrugs I-D1-R1 (NO-aspirin) and I-D2-R1 (NO-naproxen) as representative examples. The nitrate/nitrite release profile in the blood plasma which is an indirect measure of the nitric oxide released in the blood plasma was measured using Griess method by employing colorimetric nitrate/nitrite assay kit from Fluka and the data obtained from the experiment is presented in FIG. 4 and Table 8.

TABLE 8

Estimation of nitrate/nitrite release from the compounds of the invention

| Compound[1] | Plasma Nitrate/Nitrite AUC (μM*h) |
|---|---|
| Vehicle | 371.10 |
| I-D1-R1[2] | 1481.00 |
| I-D2-R1[3] | 686.80 |

[1]All the compounds were administered orally;
[2]NO-aspirin at a dose equimolar to 10 mg/kg dose of aspirin;
[3]NO-naproxen at a dose equimolar to 30 mg/kg dose of naproxen.

It was observed that significant amounts of nitric oxide (in the form of nitrite/nitrate) were released from these promising compounds of this invention represented by formula (I).

Gastric Ulcer-Sparing Properties of Compounds of the Invention:

The gastric ulcer-sparing potential of prodrugs I-D1-R1 (NO-aspirin at 298.85 mg/kg, which is equimolar to 200 mg/kg dose of aspirin) and I-D2-R1 (NO-naproxen at 138.67 mg/kg, which is equimolar to 100 mg/kg dose of naproxen) was assessed and compared with gastric ulcer-causing potential of their respective parent drugs, aspirin and naproxen (at doses of 100 mg/kg) in rats. The results (stomach images) from these experiments are presented in FIGS. 5A and 6A, respectively. The results clearly establish that none of the animals treated with prodrugs I-D1-R1 (NO-aspirin) and I-D2-R1 (NO-naproxen) showed any significant development of gastric ulcers or lesions. However, severe hemorrhagic lesions and ulcers were seen to develop in rats administered with parent drugs, aspirin (100 mg/kg) and naproxen (100 mg/kg). For clarity, the gastric lesion and ulcer area (in mm$^2$) for aspirin and its prodrug I-D1-R1 (NO-aspirin) is shown in FIG. 5B. Similarly, the gastric lesion and ulcer area (in mm$^2$) for naproxen and its prodrug I-D2-R1 (NO-naproxen) is shown in FIG. 6B.

Inhibition of Serum Thromboxane B2 (TXB2) Formation by Aspirin and its Prodrug I-D1-R1:

Aspirin is used as an antiplatelet agent for the treatment of cardiovascular complications. Aspirin shows its antiplatelet activity by inhibition of platelet cyclooxygenase (COX) (COX is responsible for generation of a potent platelet activator thromboxane A2 (TXA2)), thus indirectly inhibiting the formation of serum TXB2 (which is a stable metabolite of TXA2) (Cox, D., et al., Stroke 2006, 37, 2153-2158). It is therefore possible to achieve complete suppression of platelet. TXA2 (and also TXB2) formation via chronic administration of aspirin at a dose of 30 mg/daily (Patrignani, P., et al. J. Clin. Invest. 1982, 69, 1366-1372). The antiplatelet activity of aspirin (30 mg/kg) and its prodrug I-D1-R1 (at a dose equimolar to 30 mg/kg dose of aspirin) was evaluated in Sprague-Dawley (SD) rats through estimation of serum TXB2 levels (Esser, R. et al., Br. J. Pharmacol. 2006, 144, 538-550) and the experimental results are presented in FIG. 7. It was observed that aspirin (30 mg/kg, p.o., o.d., 7 days) and its prodrug I-D1-R1 (44.82 mg/kg, equivalent to 30 mg/kg of aspirin, p.o., o.d., 7 days) exhibited nearly comparable inhibition of TXB2 formation (75.97% versus 72.59%) at equimolar doses. The result unequivocally establishes that I-D1-R1, which exhibits significant antiplatelet activity (unique to the wonder drug aspirin), is indeed a true prodrug of aspirin (FIG. 7).

Stability of Prodrugs I-D1-R1 (NO-Aspirin) and I-D2-R1 (NO-Naproxen) at RT and at 50° C.:

Stability of prodrugs I-D1-R1 (NO-aspirin) and I-D2-R1 at RT and at 50° C. was tested and the results from the experiments are presented in Table 9.

TABLE 9

Stability of prodrugs I-D1-R1 and I-D2-R1 at RT and at 50° C.[a]

| | I-D1-R1 | | | | | | I-D2-R1 | | | |
|---|---|---|---|---|---|---|---|---|---|---|
| | RT | | | 50° C. | | | RT | | 50° C. | |
| Time | I-D1-R1 | Asp | SA | I-D1-R1 | Asp | SA | I-D2-R1 | Nap | I-D2-R1 | Nap |
| 0 h | 99.14% | NIL | NIL | 99.14% | NIL | NIL | 99.12% | NIL | 99.12% | NIL |
| 2 d | — | — | — | 98.84% | NIL | 0.1% | — | — | — | — |
| 3 d | 98.89% | NIL | NIL | — | — | — | — | — | — | — |
| 5 d | — | — | — | 98.18% | 0.3% | 0.14% | — | — | — | — |
| 18 d | 98.95% | NIL | NIL | — | — | — | — | — | — | — |
| 25 d | — | — | — | — | — | — | 98.87% | 0.2% | 99.00% | 0.33% |
| 1 m | 98.56% | 0.13% | NIL | 88.34% | 2.8% | 0.6% | — | — | — | — |

[a]Samples were kept in capped vials.
RT = Room Temperature.
Asp = Aspirin.
SA = Salicylic acid.
Nap = Naproxen.
d = days.
— = not done.
m = month.

Thus, the aspirin prodrug I-D1-R1 was found to be very stable at RT up to 1 month. However, when it was incubated at 50° C., it degraded slightly (~1%) after 5 days and about 11% after 1 month. After 1 month of incubation at 50° C., about 2.8% of aspirin and 0.6% of salicylic acid were generated. In the case of naproxen prodrug I-D2-R1, the prodrug remained stable both at RT and at 50° C. for up to 25 days (period of study) and released only negligible amounts (~0.20% at RT and ~0.33% at 50° C.) of naproxen after 25 days.

In-vitro Metabolic Stability Studies on Aspirin Prodrug I-D1-R1 in Biologically Relevant Fluids such as Simulated Gastric Fluid (SGF), Simulated Intestinal Fluid (SIF) and Human Plasma:

In order to confirm that the compound I-D1-R1 (NO-aspirin) is indeed acting as a true prodrug of aspirin, it was incubated in biologically relevant fluids such as Simulated Gastric Fluid (SGF), Simulated Intestinal Fluid (SIF) and human plasma and the corresponding results are presented in FIGS. 8-11. The prodrug was evaluated at a concentration of either 100 µM or 1 mM and has shown dose dependent decrease/increase in the amount of aspirin released. As shown in the figures, aspirin was co-evaluated as a positive control under the same experimental conditions, at equimolar doses, for a meaningful comparison of the results.

In SGF, as shown in FIG. 8, the prodrug I-D1-R1 released significant amounts (AUC: 10406 µM*h) of aspirin, which is only about 15% less than that of aspirin (AUC: 12348 µM*h) at equimolar doses.

In SIF also, as shown in FIG. 9, the prodrug I-D1-R1 released significant amount of aspirin at 1 mM concentration. However, although the aspirin-release increased in a dose-dependent manner, it was significantly less (~30%) than that of aspirin standard (AUCs: 136861 mM*h versus 94862 mM*h) at equimolar doses. In SIF, with its pH in the range of ~6-7, a certain percentage of the prodrug preferentially underwent de-acetylation to give salicylic acid derivative which further degraded to salicylic acid. This aspect of preferential de-acetylation was much more pronounced when the prodrug I-D1-R1 was incubated in human plasma as shown in FIG. 10.

Thus, in human plasma, the prodrug I-D1-R1 released negligible amount (~5%) of aspirin (AUC: 352 µM*h versus 6803 µM*h for equimolar amount of aspirin) (FIG. 10). However, as expected, a large and proportional amount of salicylic acid was released, as shown in FIG. 11. In this case, plasma esterases preferentially hydrolyzed O-acetyl group of the prodrug to give salicylic acid as the major metabolite.

Although the above examples (prodrugs) were made from NSAIDs, the technology is not limited but can be extended to other therapeutic agents containing at least one carboxylic acid group. Thus, we have made one such example using an anti-cancer drug, chlorambucil, which is represented by I-D3-R1 (structure shown below).

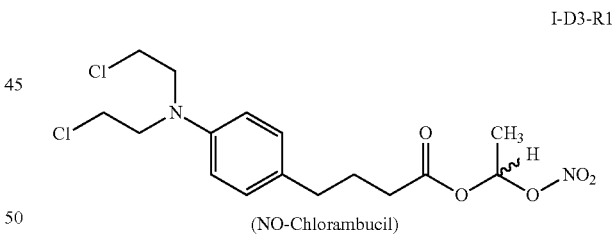

(NO-Chlorambucil)

As anticipated, on incubation in SGF, the prodrug I-D3-R1 also showed quantitative release of the parent drug, chlorambucil (See FIG. 12).

The chlorambucil prodrug I-D3-R1, which is the lowest carbon homologue in the series, decomposed in SGF to give 100% of the parent drug chlorambucil with a half-life of less than 5 minutes.

Example 9

Pharmacokinetic Data for the Compounds of the Invention

Representative compounds of formula (I) of the present invention that are the nitric oxide releasing prodrugs of known drugs or therapeutic agents containing at least one carboxylic acid group, were subjected to pharmacokinetic study and the method and results of the study are presented herein below:

Animals:

Male Sprague-Dawley (SD) rats weighing 150-220 g were used in the study (Exception: Wistar rats were used for one study). The rats were fed normal standard laboratory chow and maintained under standard environmental conditions (room temperature of 22±2° C.; 50±10% relative humidity; 12 hrs light-dark cycle). All experimental procedures mentioned below were approved by the institutional animal ethics committee and were performed in accordance with standard guidelines of Committee for the purpose of control and supervision of experiments on animals (CPCSEA); Govt. of India for the experiment on animals.

General Procedures:

The oral pharmacokinetic profile of the compounds of the invention was studied in male Sprague-Dawley (SD) rats. However, for one study, Wistar rats were used. For the purpose of these studies, the nitric oxide releasing prodrugs of drugs containing a carboxylic acid functional group, e.g. naproxen and aspirin, which are encompassed in the compounds of formula (I), were selected as representative examples. The release profiles of parent drugs, naproxen and aspirin from their nitric oxide releasing prodrugs were analyzed by a HPLC system.

HPLC Sample Preparation and Standard Curve:

HPLC: Waters Alliance analytical HPLC equipped with 2996 PDA detector and Empower software were used to analyze the samples.

HPLC Column: Waters X-Terra RP-18 reversed phase column, 150×3.9 mm, 5 μm

HPLC Method: Flow: 1 mL/min, detector set at 210 nm and at Maxplot (210-400 nm range);

Solvent A: Acetonitrile;
Solvent B: 0.1% TFA in water.
Injection volume: 20 μl

Elution Method: A Linear Gradient as Specified Below

| Time in min | 0-2 | 2-10 | 10-13 | 13-14 | 14-18 |
|---|---|---|---|---|---|
| % A | 20 | 20-100 | 100 | 100-20 | 20 |

Blood samples were collected from the rats and the plasma was separated by centrifugation at 1000×g for 5 min at 4° C. A stock solution of the parent drug was prepared by dissolving it in acetonitrile and working solutions of various concentrations (0.625, 1.25, 2.5, 5, 10, 20 μg/mL) were prepared by spiking the blood plasma with the naproxen stock solution. Each plasma sample (50 μl) was then transferred to a micro centrifuge tube containing acetonitrile (200 μl), mixed by vortex and centrifuged for 5 min (1000×g) at 4° C. The supernatant layer (150 μl) obtained after centrifugation was then transferred to HPLC vials. The sample solution (25 μl) was then injected in to HPLC for analysis. A linear calibration curve between the naproxen concentration in plasma (0.625, 1.25, 2.5, 5, 10, 20 μg/mL) and the peak area ratio was obtained. The rats were divided into groups and three rats were placed in each group. Parent NSAID (i.e., aspirin at a dose of 30 mg/kg or naproxen at a dose of 10 mg/kg) was administered orally to one group of rats and the representative compounds of formula (I), i.e., the nitric oxide releasing prodrugs of aspirin (i.e., I-D1-R1, I-D1-R2 and I-D1-R3, at a dose equivalent to 30 mg/kg of aspirin) and naproxen (i.e., I-D2-R1, I-D2-R2, I-D2-R3 and I-D2-R4, at a dose equivalent to 10 mg/kg of naproxen) were administered orally to the remaining groups. Blood was collected from orbital plexus of the rats according to a specific schedule (0.25, 0.5, 1, 2, 4, 6 and 8 h after dosing) and the plasma was separated from each sample by centrifugation for 5 min (1000×g) at 4° C. Each collected plasma sample (50 μl) corresponding to respective parent drug (i.e., aspirin or naproxen) and the aforementioned nitric oxide releasing prodrugs of aspirin or naproxen was then transferred to a micro centrifuge tube containing acetonitrile (200 μl), mixed by vortex and centrifuged for 5 min (1000× g) at 4° C. The supernatant layer (150 μl) obtained after centrifugation was then transferred to HPLC vials. A (25 μl) volume of each sample solution was injected into HPLC for analysis. The plasma concentration of salicylic acid or naproxen in rats after oral administration of the respective parent drugs (i.e., aspirin or naproxen) and their respective nitric oxide releasing prodrugs versus time intervals was plotted and the area under the curve was determined by trapezoidal rule (Gibaldi, M. and Perrier, D., Pharmacokinetics, Second edition, 15:445-447) for each of the samples corresponding to parent drug (aspirin or naproxen) and their respective nitric oxide releasing prodrugs. The AUC values for the nitric oxide releasing prodrugs of aspirin and naproxen were determined.

Example 10

Estimation of Nitrate/Nitrite Release from the Compounds of the Invention In-Vivo Male Sprague-Dawley (SD) rats (180-220 g) were acclimatized for a week and fasted 12-14 hours prior to the commencement of the experiment. The representative compounds of formula (I), i.e., the nitric oxide releasing prodrugs of aspirin (i.e., I-D1-R1) at a dose equivalent to 30 mg/kg dose of aspirin and naproxen (I-D2-R1) at a dose equivalent to 10 mg/kg dose of naproxen were administered orally to the rats. The blood sample was collected from the rats administered with each of the aforementioned nitric oxide releasing prodrugs of aspirin and naproxen according to a specific schedule (0.5, 1, 2, 4, 6 and 8 hours) and the plasma was separated by centrifugation (1000×g) for 5 min at 4° C. The release profile of the nitrate/nitrite in the blood plasma which is an indirect measure of the nitric oxide released in the blood plasma was measured using Griess method by employing colorimetric nitrate/nitrite assay kit from Fluka.

The blood plasma samples were filtered using Millipore ultra-filtration 96-well plate to remove the plasma proteins having particle size of >10 kDa. The assay was performed in a 96-well plate according to standard procedure described in the kit. The method comprised adding to the well, standard (sodium nitrate) (80 μl) of various concentrations (0, 20, 40, 60, 80 and 100 μM) followed by the reagents, nitrate reductase (10 μl) and enzyme co-factor (10 μl). The plasma sample (80 μl) obtained from the blood sample collected at various time intervals from the rats (0.5, 1, 2, 4, 6 and 8 hours) were added to separate wells, followed by the reagents, nitrate reductase (10 μl) and enzyme co-factor (10 μl). The plate was incubated for 2 h at room temperature on orbital shaker (350-400 rpm). Griess reagent A (50 μl) was added to each well followed by incubation for 5 min and subsequently, Griess reagent B (50 μl) was added to each well followed by incubation for 10 min. The absorbance of assay plate was measured by using a 96-well plate reader (Bio-Tek instruments) at 540 nm. This procedure was carried out for each of the aforementioned nitric oxide releasing prodrugs of aspirin and naproxen individually. A standard curve between the sodium nitrate concentration (µM) (0, 20, 40, 60, 80 and 100 µM) on X-axis versus absorbance values on Y-axis was plotted. The absorbance values of each of the plasma samples collected at different time intervals corresponding to the aforementioned nitric oxide releasing prodrugs of aspirin and naproxen from the rats was compared with the standard curve to determine the plasma nitrate concentration in mice after oral administration of the aforementioned nitric oxide releasing prodrugs of aspirin and naproxen. The plasma nitrate concentration in rats after oral administration of the aforementioned nitric oxide releasing prodrugs of aspirin and naproxen versus time intervals was plotted and the area under the curve was determined for each of the samples corresponding to the aforementioned nitric oxide releasing prodrugs of aspirin and naproxen (FIG. 4).

Example 11

Determination of the Anti-Inflammatory Activity of the Compounds of the Invention With an intention to save resources and experimental animals, anti-inflammatory activity of the compounds of this invention was not determined experimentally. The decision was based on the observation that the anti-inflammatory activity of a drug is generally shown to be directly proportional to the amount of drug present in the blood plasma. Since the AUC values (i.e., bioavailability) of some representative compounds of this invention are comparable [in case of aspirin prodrug I-D1-R1 (NO-aspirin)] or superior [in case of naproxen prodrug I-D2-R1 (NO-naproxen)] to those of their respective parent drugs aspirin or naproxen, we have intentionally not tested anti-inflammatory activity of these promising NO-NSAIDs. However, the anti-inflammatory activity of NO-aspirin (i.e., I-D1-R1) and NO-naproxen (i.e., I-D2-R1) and their respective parent drugs aspirin and naproxen can be assessed in carrageenan-induced rat paw edema model according to the reported procedure (O. A. Al-Swayeh, O. A., et al., Br. J. Pharmacol. 2000, 129, 343-350). Thus, Male Sprague-Dawley (SD) rats are to be divided into three groups consisting of ten rats in each group. Parent drugs aspirin (30 mg/kg) or naproxen (10 mg/kg) and NO-aspirin (I-D1-R1, at a dose equivalent to 30 mg/kg dose of aspirin) and NO-naproxen (I-D2-R1, at a dose equivalent to 10 mg/kg dose of naproxen) are to be dissolved in PEG 400 and administered orally to overnight fasted rats of different groups. One hour later, carrageenan (100 µl, 1% w/v) is to be injected in to their paws. The control group is to be given PEG 400 (1 mL/kg). The paw volume of the groups of rats administered with parent drugs and those administered with prodrugs are to be measured before carrageenan injection and also at a time period of 3 and 5 hours after the injection of carrageenan. The (%) inhibition of paw edema in rats administered with parent drugs (aspirin and naproxen) and NO-NSAIDS (I-D1-R1 and I-D2-R1) after 3 and 5 hours, respectively, are to be calculated and compared with that of the control group.

Example 12

Acute Gastric Ulcerogenesis Activity Study

The ulcerogenic potential of NO-aspirin (i.e., I-D1-R1) and NO-naproxen (i.e., I-D2-R1) was assessed in rats. Thus, aspirin (100 mg/kg) and naproxen (100 mg/kg) and their respective nitric oxide releasing prodrugs I-D1-R1 and I-D2-R1 (at doses equivalent to 100 mg/kg of aspirin and naproxen, respectively) were administered to overnight fasted rats of different groups. The animals were sacrificed after 5 h of drug administration. The stomachs of the treated animals were separated, perfused with 2% formalin (10 mL), and a large curvature was excised. The severity of the mucosal damage was assessed on the basis of the size of the observed ulcer lesions in the images captured using a stereomicroscope attached to a digital camera (Stemi 2000, Zeiss, Germany). The Image Pro Plus software (version 5.1) was used to quantify the hemorrhagic/ulcer lesions in pixels and to convert them into mm$^2$. The total area of lesions was calculated for each treatment group and the measure of gastric ulcers (Mean±SEM) (mm$^2$) was estimated (FIGS. 5 and 6).

Example 13

Estimation of Serum $TXB_2$ Levels

In vivo $TXB_2$ inhibition potential of aspirin and NO-aspirin prodrugs was assessed in Sprague-Dawley (SD) rats; the serum $TXB_2$ levels were estimated according to the reported procedure (R. Esser, R., et al., Br. J. Pharmacol. 2006, 144, 538-550). Thus, vehicle, aspirin (30 mg/kg) or aspirin prodrug I-D1-R1 (44.82 mg/kg which is equivalent to 30 mg/kg dose of aspirin) were administered orally to the overnight fasted SD rats. After six hours of drug administration, the blood samples were obtained from the rats by retro-orbital plexus puncture under light isoflurane anesthesia. The whole blood samples were immediately transferred into glass tubes and allowed to clot at 37° C. for 60 min; the serum was separated by centrifugation (10 min at 2000 rpm) and kept at −20° C. until assayed for $TXB_2$. The serum $TXB_2$ concentrations were determined by enzyme immunoassay (EIA) using commercially available $TXB_2$ estimation kit (Cayman Chemicals, USA), according to the method described in kit information booklet.

Example 14

In-Vitro Metabolic Stability Studies in Biological Fluids

Preparation of Biological Fluids
Simulated Gastric Fluid (SGF):
SGF was prepared according to the procedure described in Test Solution—USP. Thus, 0.2 g of sodium chloride and 0.32 g of purified pepsin (Sigma, derived from porcine stomach mucosa with an activity of 800 to 2500 units per mg of protein) were dissolved in 0.7 mL of hydrochloric acid and sufficient water to make 100 mL. This test solution has a pH of about 1.2 and was utilized for in-vitro studies.
Simulated Intestinal Fluid (SIF):
SIF was prepared according to the procedure described in Test Solution—USP. Thus, 0.68 g of monobasic potassium phosphate was dissolved in 25 mL of water followed by addition of 0.2N NaOH (7.7 mL) and water (50 mL). To this solution was added pancreatin (1 g) and mixed; the pH of the resulting solution was adjusted to about 6.8 with 0.2N HCl/0.2N NaOH and the solution, was diluted with water to 100 mL. The solution was utilized for in-vitro studies.
Human Plasma:
Human Plasma was similarly obtained by processing the blood taken from healthy human male volunteers (age group 25-35 years) who had not consumed any NSAIDS one week prior to the collection of blood. This plasma was utilized for the in-vitro experiments.

In-Vitro Metabolic Stability of Aspirin, Naproxen and their Respective Prodrugs I-D1-R1 (NO-Aspirin) and I-D2-R1 (NO-Naproxen) in Simulated Gastric Fluid (SGF), Simulated Intestinal Fluid (SIF) and Human Plasma:

The solution of the test compound in acetonitrile (10 µL of 100 µM solution) was dissolved in 990 µL of biological fluid (SGF/SIF/Human Plasma). The resulting reaction mixtures were incubated at 37° C. At specified time intervals, aliquots (60 µL) were withdrawn and added to acetonitrile (200 µL) and mixed well by vortexing for 2 minutes. The mixture was centrifuged at 13000 rpm for 15 min at 4° C., and the supernatant analyzed by HPLC. The amounts (area percentages) of the remaining intact prodrug (if any) and the released metabolite(s) were estimated by HPLC.

Statistical Analysis

Statistical analyses of data consisting of three or more groups were performed using one-way analysis of variance (one-way ANOVA) followed by post-hoc Dunnett's multiple comparison test, and values of $p<0.05$ were considered as significant. For data consisting of two groups, analyses were performed using student's t test and values of $p<0.05$ were considered as significant. All analyses were carried out using GraphPad Prism version 4.00 for Windows (GraphPad Software, San Diego, Calif., USA). For data consisting of only pooled/mean values, the statistical analysis could not be performed.

HPLC Analysis

This was performed by using HPLC instrument (Waters alliance), pump 2695, and PDA detector 2996 with the following chromatographic parameters: Wavelength –210 nm; Column-Waters X-Terra RP-18, 150×3.9 mm, 5 µm; Injection volume, 25 µL; Run time, 13 min. Mode of operation was linear gradient with mobile phase A: Acetonitrile and B: 0.1% TFA in water (filtered and degassed). Flow rate was 1.0 mL/min at 25° C.

The invention claimed is:

1. A derivative of a therapeutic agent comprising aspirin, naproxen, or chlorambucil, selected from the group consisting of:

I-D1-R1

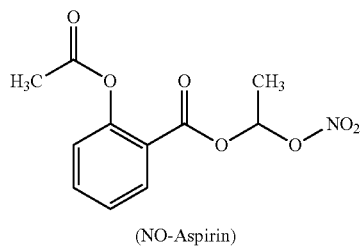

(NO-Aspirin)

I-D1-R2

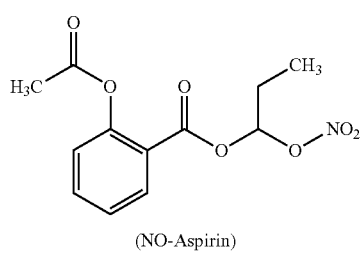

(NO-Aspirin)

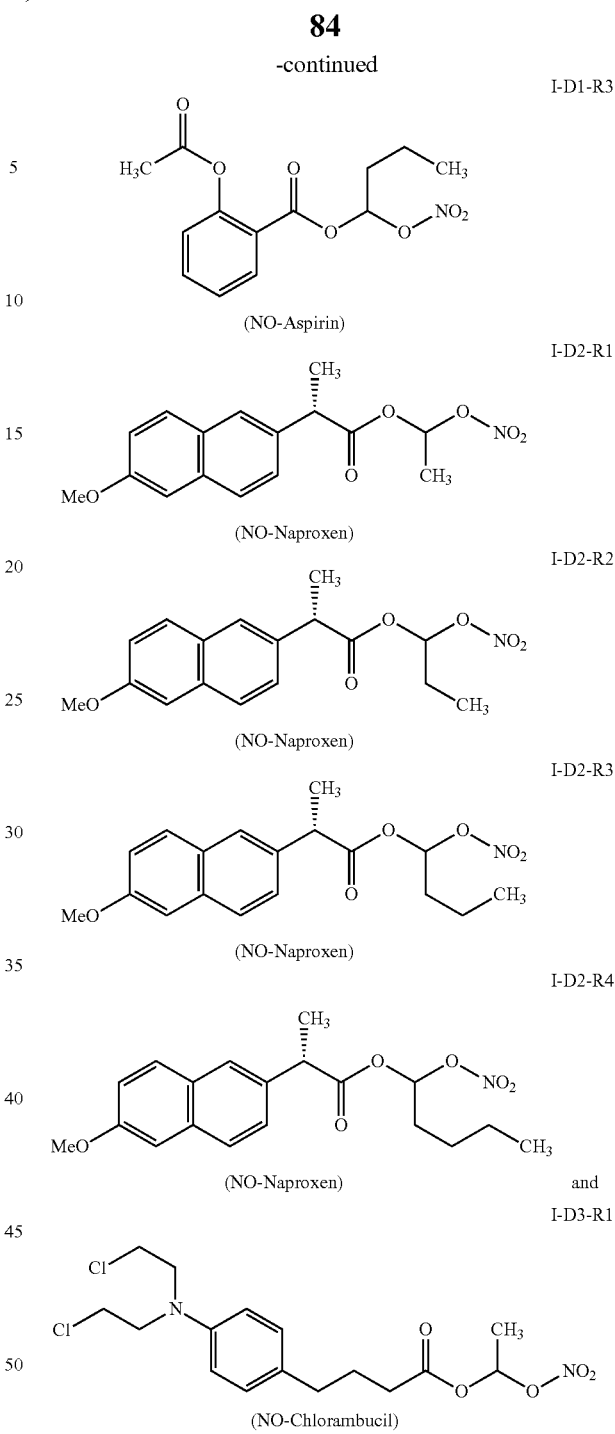

or geometrical, stereo-isomers, or pharmaceutical compositions thereof.

2. A pharmaceutical composition comprising a therapeutically effective amount of the compound of claim 1, or a pharmaceutically acceptable salt thereof and one or more of pharmaceutically acceptable carriers, vehicles or diluents.

3. A method of treating a disease or disorder in a human or mammal where a chronic, sustained and selective release of the constituent drug or therapeutic agent and/or nitric oxide is beneficial, wherein the disease or disorder is selected from the group consisting of soft tissue inflammation, pain, arthritis, or a thrombotic cardiovascular event, comprising administering to the mammal or human in need of the treatment a therapeutically effective amount of the compound of claim 1.

4. A method of treating a disease or disorder in a human or mammal where a chronic, sustained and selective release of the constituent drug or therapeutic agent or nitric oxide is beneficial, wherein the disease or disorder is selected from the group consisting of soft tissue inflammation, pain, arthritis, or a thrombotic cardiovascular event, comprising administering to said mammal a therapeutically effective amount of the pharmaceutical composition as claimed in claim 2.

5. A process for the preparation of the derivative of a therapeutic agent of claim 1 or a pharmaceutically acceptable salt thereof, wherein the process comprises the steps of:
   a) reacting the therapeutic agent with oxalyl chloride or thionyl chloride to form a reactive acid chloride;
   b) coupling the reactive acid chloride obtained in step a with an aldehyde in the presence of a catalyst zinc chloride and dichloromethane to form intermediate compound; and
   c) nitration of the intermediate compound obtained in step b with silver nitrate in the presence of acetonitrile to form the derivative of claim 1 and optionally conversion of the compound to its pharmaceutically acceptable salt.

6. A process for the preparation of the derivative of a therapeutic agent of claim 1 or a pharmaceutically acceptable salt thereof, wherein the process comprises the steps of:
   a) selectively protecting a functional group of the therapeutic agent;
   b) treating the compound obtained in step a, with oxalyl chloride or thionyl chloride in the presence of dichloromethane to yield a reactive acid chloride intermediate;
   c) reaction of the intermediate obtained in step b with an aldehyde in the presence of zinc chloride and dichloromethane to form an intermediate compound; and
   d) nitration of the intermediate compound obtained in step c with silver nitrate in the presence of a acetonitrile to form the derivative of claim 1 or its pharmaceutically acceptable salt.

\* \* \* \* \*